(12) United States Patent
Arnold et al.

(10) Patent No.: US 10,093,653 B2
(45) Date of Patent: *Oct. 9, 2018

(54) VITAMIN D RECEPTOR-COREGULATOR INHIBITORS

(71) Applicants: UWM Research Foundation, Inc., Milwaukee, WI (US); Women and Infants Hospital of Rhode Island, Providence, RI (US)

(72) Inventors: Alexander E. Arnold, Milwaukee, WI (US); Preetpal Singh Sidhu, Milwaukee, WI (US); Premchendar Nandhikonda, Milwaukee, WI (US); Rakesh K. Singh, Barrington, RI (US)

(73) Assignees: UWM Research Foundation, Inc., Milwaukee, WI (US); Women and Infants Hospital of Rhode Island, Providence, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/238,305

(22) Filed: Aug. 16, 2016

(65) Prior Publication Data

US 2017/0174655 A1    Jun. 22, 2017

Related U.S. Application Data

(63) Continuation of application No. 14/240,828, filed as application No. PCT/US2012/052416 on Aug. 26, 2012, now Pat. No. 9,416,104.

(60) Provisional application No. 61/527,780, filed on Aug. 26, 2011.

(51) Int. Cl.
| | |
|---|---|
| C07D 401/12 | (2006.01) |
| A61K 45/06 | (2006.01) |
| A61K 31/404 | (2006.01) |
| C07D 407/12 | (2006.01) |
| C07D 209/16 | (2006.01) |
| C07D 209/10 | (2006.01) |
| C07D 209/14 | (2006.01) |

(52) U.S. Cl.
CPC .......... *C07D 401/12* (2013.01); *A61K 31/404* (2013.01); *A61K 45/06* (2013.01); *C07D 209/10* (2013.01); *C07D 209/14* (2013.01); *C07D 209/16* (2013.01); *C07D 407/12* (2013.01)

(58) Field of Classification Search
CPC .................................................. C07D 401/12
See application file for complete search history.

(56) References Cited

U.S. PATENT DOCUMENTS

| | | |
|---|---|---|
| 5,342,547 A | 8/1994 | Konya et al. |
| 9,416,104 B2 | 8/2016 | Arnold et al. |
| 2003/0060497 A1 | 3/2003 | Gerlach et al. |
| 2009/0163545 A1 | 6/2009 | Goldfarb |

FOREIGN PATENT DOCUMENTS

WO    WO 2011094708    8/2011

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Rees, et al. Document No. 62:36803, retrieved from STN; Entered in STN on Apr. 22, 2001.*
Anderson, M.G. et al. "Expression of VDR and CYP24A1 mRNA in human tumors," (2006). Cancer, Chemotherapy and Pharmacology, 57(2): 234-240.
Andreichikov, Y.S. "Oxalyl derivatives of methyl ketones. XLIV. Synthesis of 4-aroyltetrahydro-1,5-diphenyl-2,3-pyrrolediones and their reaction with amines and hydrazine," (1986). Zh Obshch Khim, 22: 1749-1756.
Arnold, L.A. et al. "Discovery of small molecule inhibitors of the interaction of the thyroid hormone receptor with transcriptional coregulators," (2005). The Journal of Biological Chemistry, 280(5): 43048-43055.
Arnold, L.A. et al. "Inhibitors of the interaction of a thyroid hormone receptor and coactivators: preliminary structure-activity relationships," (2007). The Journal of Medicinal Chemistry, 50: 5269-5280.
Arnold, L.A.et al. "Synthesis and Characterization of BODIPY-labeled Colchicine," (2008). Bioorganic & Medicinal Chemistry Letters, 18(22): 5867-5870.
Banerji, et al. Document No. 99:5477, retrieved from CAPLUS.
Beer, T.M. et al. "Weekly high-dose calcitriol and docetaxel in advanced prostate cancer," (2001). Seminars in Oncology, 28: 49-55.
Berge, M. et al. "Pharmaceutically Acceptable Salts," (1977). Journal of Pharmaceutical Sciences and Research, 66: 1-19.
Bikle, D.D. et al. "Differential regulation of epidermal function by VDR coactivators," (2010). The Journal of Steroid Biochemistry and Molecular Biology, 121: 308-313.

(Continued)

*Primary Examiner* — Shawquia Jackson
(74) *Attorney, Agent, or Firm* — Michael Best & Friedrich

(57) ABSTRACT

Described herein are compounds, pharmaceutical compositions and methods for inhibiting the expression of a vitamin D receptor target gene, inhibiting interactions between the vitamin D receptor and at least one vitamin D receptor coactivator, for treating cancer in a subject, and for inhibiting angiogenesis in a subject.

14 Claims, 10 Drawing Sheets

Specification includes a Sequence Listing.

(56) References Cited

OTHER PUBLICATIONS

Blutt, S. et al. "Calcitriol-induced apoptosis in LNCaP cells is blocked by overexpression of Bcl-2," (2000). Endocrinology 141(1): 10-17.

Boehm, M. et al. "Novel Nonsecosteroidal Vitamin D Mimics Exert VDR-modulating Activities with Less Calcium Mobilization than 1,25-Dihydroxyvitamin D3," (1999). Chemistry and Biology, 6(5): 265-275.

Bosch, X. et al. "Hypercalcemia due to endogenous overproduction of 1,25-dihydroxyvitamin D in Crohn's disease," (1998). Gastroenterology, 114(5): 1061-1065.

Brumbaugh, P. et al. "1 Alpha, 25-dihydroxycholecalciferol receptors in intestine," (1974). The Journal of Biological Chemistry, 249(4): 1251-1257.

Brumbaugh, P. et al. "1 Alpha, 25-dihydroxycholecalciferol receptors in intestine. II. Temperature-dependent transfer of the hormone to chromatin via a specific cytosol receptor," (1974). The Journal of Biological Chemistry, 249(4): 1258-1262.

Campbell, M.J. et al, "Vitamin D3 analogs and their 24-oxo metabolites equally inhibit clonal proliferation of a variety of cancer cells but have differing molecular effects," (1997). Journal of Cellular Biochemistry, 66: 413-425.

Chemical Abstract Compounds, New STN BETA ver datasheet retrieved from the internet; <URL: http://www.stn.org/stn> (2012).

Chen, K.S., et al. "Cloning of the human 1 alpha,25-dihydroxyvitamin D-3 24-hydroxylase gene promoter and identification of two vitamin D-responsive elements," (1995). Biochimica et Biophysica Acta, 1263(1): 1-9.

Chen, H. et al. "Nuclear receptor coactivator ACTR is a novel histone acetyltransferase and forms a multimeric activation complex with P/CAF and CBP/p300," (1997). Cell, 90: 569-580.

Chen, et al. Document No. 155:211592, retrieved from STN; entered in STN on Jul. 7, 2011.

Chou, T.C. "Theoretical basis, experimental design, and computerized simulation of synergism and antagonism in drug combination studies," (2006). Pharmacological Reviews, 58: 621-681.

Chouvet, C. et al. "1,25-Dihydroxyvitamin D3 inhibitory effect on the growth of two human breast cancer cell lines (MCF-7, BT-20)," (1986). The Journal of Steroid Biochemistry, 24: 373-376.

Cross, H.S. et al. "Antiproliferative effect of 1,25-dihydroxyvitamin D3 and its analogs on human colon adenocarcinoma cells (CaCo-2): influence of extracellular calcium," (1991). Biochemical and Biophysical Research Communications, 179: 57-62.

Dai, Z. et al. "Mitochondrial comparative proteomics of human ovarian cancer cells and their platinum-resistant sublines," (2010). Proteomics, 10(21): 3789-99.

Deeb, A. et al. "Heterocyclic Synthesis with 3-Cyano-2(1h) Pyridinethione: Synthesis of 3-Oxo-2,3-dihydroisothiazolo[5,4-b]pyridine and Related-Compounds," (1990). Monatshefte fur Chemie / Chemical Monthly, 121(4): 281-287.

Drivdahl, R.H. et al. "IGF-binding proteins in human prostate tumor cells: expression and regulation by 1,25-dihydroxyvitamin D3," (1995). Prostate, 26: 72-79.

Estebanez-Perpina, E. et al. "The molecular mechanisms of coactivator utilization in ligand-dependent transactivation by the androgen receptor," (2005). The Journal of Biological Chemistry, 280(9): 8060-8068.

Esvelt, R.P. et al. "Isolation and Characterization of 1 a-Hydroxy-23-carboxytetranorvitamin D: A Major Metabolite of 1,25-Dihydroxyvitamin D3," (1979). Biochemistry, 18(18): 3977-3983.

Eyduran, F. et al. "4,6-Dimethyl-2-thioxo-1,2-dihydropyridine3-carbonitrile," (2007). Acta Crystallographica Section, E 63: 02415-02417.

Feau, C., et al. "Novel flufenamic acid analogues as inhibitors of androgen receptor mediated transcription,"(2009), ACS Chemical Biology, 4(10): 834-843.

Glass, A.R. et al. "Ketoconazole-Induced Reduction in Serum 1,25-Dihydroxyvitamin D," (1986). The Journal of Clinical Endocrinology & Metabolism, 63: 766-769.

Greene, T.W. et al. "Protective Groups in Organic Synthesis," (1999). 3rd Edition, John Wiley and Sons, New York.

Gross, C. et al. "Treatment of Early Recurrent Prostate Cancer With 1, 25-Dihydroxyvitamin D3 (Calcitriol)," (1998). The Journal of Urology, 159(6): 2035-2040.

Gulliford, T. et al. "A phase I study of the vitamin D analogue EB 1089 in patients with advanced breast and colorectal cancer," (1998). British Journal of Cancer,78(1): 6-13.

Guenther, M.G. et al. "A core SMRT corepressor complex containing HDAC3 and TBL1, a WD40-repeat protein linked to deafness," (2000). Genes and Development, 14: 1048-1057.

Heery, D.M. et al. "A signature motif in transcriptional co-activators mediates binding to nuclear receptors," (1997). Nature, 387: 733-736.

Herdick, M. et al. "Antagonistic action of a 25-carboxylic ester analogue of 1α,25-dihydroxyvitamin D3 is mediated by a lack of ligand-induced vitamin D receptor interaction with coactivators," (2000). The Journal of Biological Chemistry, (22): 16506-16512.

Higuchi, T. Ed. et al. "Pro-drugs as Novel Delivery Systems," (1975). American Chemical Society Symposium Series, 14.

Hoenderop, J. G. et al. "Molecular identification of the apical Ca2+ channel in 1, 25-dihydroxyvitamin D3-responsive epithelia," (1.999). The Journal of Biological Chemistry, 274: 8375-8378.

Holick, M.F., et al. "1,24,25-Trihydroxyvitamin D3 : A metabolite of vitamin D3 effective on intestine," (1973). The Journal of Biological Chemistry, 248: 6691-6696.

Hong, H. et al. "GRIP1, a transcriptional coactivator for the AF-2 transactivation domain of steroid, thyroid, tetinoid, and vitamin D receptors," (1997). Molecular and Cellular Biology, 17(5): 2735-2744.

Horst, R.L. et al. "24-Hydroxylation of 1,25-dihydroxyergocalciferol. An unambiguous deactivation process," (1986). The Journal of Biological Chemistry, 261(20): 9250-9256.

Hsieh, J.C. et al. "Physical and functional interaction between the vitamin D receptor and hairless corepressor, two proteins required for hair cycling," (2003).The Journal of Biological Chemistry, 278(40): 38665-38674.

Huang, E.Y. et al. "Nuclear receptor corepressors partner with class II histone deacetylases in a Sin3-independent repression pathway," (2000). Genes and Development, 14: 45-54.

Huth, J.R., et al. "Toxicological evaluation of thiol-reactive compounds identified using a La Assay to detect reactive molecules by nuclear magnetic resonance," (2007). Chemical Research in Toxicology, 20: 1752-1759.

Hwang, J. Y. et al. "Improvement of pharmacological properties of irreversible thyroid receptor coactivator binding inhibitors," (2009). Journal of Medicinal Chemistry, 52(13): 3892-3901.

Hwang, J.Y. et al. "Methylsulfonylnitrobenzoates, a new class of irreversible inhibitors of the interaction of the thyroid hormone receptor and its obligate coactivators that functionally antagonizes thyroid hormone," (2011). The Journal of Biological Chemistry, 286: 11895-11908.

Ikezoe, T. et al. "CCAAT/enhancer-binding protein delta: a molecular target of 1,25-dihydroxyvitamin D3 in androgen-responsive prostate cancer LNCaP cells," (2005). Cancer Research, 65(11): 4762-4768.

Ishizuka, S. et al. "Vitamin D antagonist, TEI-9647, inhibits osteoclast formation induced by 1α,25-dihydroxyvitamin D3 from pagetic bone marrow cells," (2004). The Journal of Steroid Biochemistry and Molecular Biology, 89-90: 331-334.

Jarde, T. et al. "In vivo and in vitro models for the therapeutic targeting of Wnt signaling using a Tet-0DeltaN89Beta-catenin system," (2012). Oncogene,1-11.

Johnson, C.S. et al. "Vitamin d receptor: a potential target for intervention," (2002). Urology, 60(3): 123-131.

Jurutka, P.W. et al. "Molecular nature of the vitamin D receptor and its role in regulation of gene expression," (2001). Reviews in Endocrine & Metabolic Disorders, 2(2): 203-216.

Kim, J. Y. et al. "Involvement of SMRT corepressor in transcriptional repression by the vitamin D Receptor," (2009). Molecular Endocrinology, 23(2):251-264.

(56) References Cited

OTHER PUBLICATIONS

Kim, K.K. et al. "Anti-angiogenic activity of cranberry proanthocyanidins and cytotoxic properties in ovarian cancer cells," (2012). International Journal of Oncology, 40(1): 227-235.
Kriebitzsch, C., et al. "The impact of 1,25(OH)2D3 and its structural analogs on gene expression in cancer cells—a microarray approach," (2009). Anticancer Research, 29(9): 3471-3483.
Krishnan, a.V. et al. "Activation of Protein Kinase-C Inhibits Vitamin D Receptor Gene Expression," (1991). Molecular Endocrinology, 5: 605-612.
Krishnan, A.V. et al. "Analysis of vitamin D-regulated gene expression in LNCaP human prostate cancer cells using cDNA microarrays," (2004). Prostate, 59(3): 243-251.
Laudet, V. et al. "A unified nomenclature system for the nuclear receptor superfamily," (1999). Cell, 97(2): 161-163.
Le Douarin, B. et al. "A possible involvement of TIFIa and TIF1, in the epigenetic control of transcription by nuclear receptors," (1996). The EMBO Journal, 15(23): 6701-6715.
Li, B.Y. et al. "InCl3-catalyzed asymmetric aza-Friedel-Crafts reaction of indoles with imines generated from O-pivaloylated Beta-D-galactosylamine," (2010). Carboydrate Research, 345(12): 1708-1712.
Li, H., et al. "RAC3, a steroid/nuclear receptor-associated coactivator that is related to SRC-1 and TIF2." (1997). Proceedings of the National Academy of Sciences, of the United States of America, 94: 8479-8484.
Liao, L. et al. "Steroid receptor coactivator 3 maintains circulating insulin-like growth factor I (IGF-I) by controlling IGF-binding protein 3 expression," (2008). Molecular Cellular Biology, 28(7): 2460-2469.
Ly, L.H. et al. "Liarozole Acts Synergistically with 1a,25-Dihydroxyvitamin D3 to Inhibit Growth of DU 145 Human Prostate Cancer Cells by Blocking 24-Hydroxylase Activity," (1999). Endocrinology, 140: 2071-2076.
MacDonald, P.N. et al. "Baculovirus-mediated expression of the human vitamin D receptor. Functional characterization, vitamin D response element interactions, and evidence for a receptor auxiliary factor," (1991). The Journal of Biological Chemistry, 266: 18808-18813.
Masuyama, H. et al. "Evidence for ligand-dependent intramolecular folding of the AF-2 domain in vitamin D receptor-activated transcription and coactivator interaction," (1997). Molecular Endocrinology, 11(10): 1507-1517.
Mathiasen, I. S. et al. "EB 1089, a novel vitamin D analogue, has strong antiproliferative and differentiation inducing effects on cancer cells," (1993). The Journal Steroid Biochemistry and Molecular Biology, 46(3): 365-371.
McGovern, S.L. et al. "A common mechanism underlying promiscuous inhibitors from virtual and high-throughput screening," (2002). Journal of Medicinal Chemistry, 45(8): 1712-1722.
Mellon, W.S. et al. "An equilibrium and kinetic study of 1,25-dihydroxyvitamin D3 binding to chicken intestinal cytosol employing high specific activity 1,25-dihydroxy [3H-26, 27]vitamin D3," (1979). Archives of Biochemistry and Biophysics, 197(1): 90-95.
Meyer, M.B. et al. "Characterizing Early Events Associated with the Activation of Target Genes by 1,25-Dihydroxyvitamin D3 in Mouse Kidney and Intestine in Vivo," (2007). The Journal of Biological Chemistry, 282(31): 22344-22352.
Meyer, M.B. et al. "The human transient receptor potential vanilloid type 6 distal promoter contains multiple vitamin D receptor binding sites that mediate activation by 1,25-dihydroxyvitamin D3 in intestinal cells," (2006). Molecular Endocrinology, 20(6): 1447-1461.
Miller, G.J. et al. "Vitamin D receptor expression, 24-hydroxylase activity, and inhibition of growth by 1alpha,25-dihydroxyvitamin D3 in seven human prostatic carcinoma cell lines," (1995). Clinical Cancer Research, 1: 997-1003.
Mita, Y. et al. "LXXLL peptide mimetics as inhibitors of the Interaction of vitamin D receptor with coactivators," (2010). Bioorganic & Medicinal Chemistry Letters, 20(5): 1712-1717.
Moore, J.M.R. et al. "Quantitative proteomics of the thyroid hormone receptor-coregulator interactions," (2004). The Journal of Biological Chemistry, 279(26): 27584-27590.
Moore, R. et al. "Efficacy of a non-hypercalcemic vitamin-D2 derived anti-cancer agent (MT19c) and inhibition of fatty acid synthesis in an ovarian cancer xenograft model," (2012). PLoS ONE, 7(4): e34443.
Moore, T. W. et al. "Inhibitors of nuclear hormone receptor/coactivator interaction," Annual Reports in Medicinal Chemistry, (2009). 44: 443-457.
Nandhikonda et al., "Discovery of the First Irreversible Small Molecule Inhibitors of the Interactin Between the Vitamin D Receptor and Coactivators," Journal of Medicinal Chemistry (2012) 55, 4640-4651.
Neri, A. "Nuove reazioni con l'isocianato di fenite. III. Benzilidenaminoindoli," (1934).Gazzetta Chimica Italiana, 64: 420-428.
Nijenhuis, T. et al. "Localization and regulation of the epithelial Ca2 channel TRPV6 in the kidney," (2003). Journal of the American Society of Nephrology, 14(11): 2731-2740.
Passerini, M. et al. "Reazione fra indoli e basi di Schiff," (1933). Gazzetta Chimica Italiana, 64: 138-144.
Posner, G.H. et al. "Potent, low-calcemic, selective inhibitors of CYP24 hydroxylase: 24-sulfone analogs of the hormone 1alpha,25-dihydroxyvitamin D3," (2004). The Journal of Steroid Biochemistry and Molecular Biology, 89-90: 5-12.
Potter, G.B. et al. "The hairless gene mutated in congenital hair loss disorders encodes a novel nuclear receptor corepressor," (2001). Genes and Development, 15: 2687-2701.
Prajapati, D. et al. "The facile and efficient three-component One-Pot Mannich-Type Reaction of Indoles Catalyzed by in (Otf)3 Under Microwave Irradiations," (2008). Letter in Organic Chemistry, 5: 365-369.
Rachez, C.et al. "A novel protein complex that interacts with the vitamin D3 receptor in a ligand-dependent manner and enhances VDR transactivation in a cell-free system," (1998).Genes and Development, 12: 1787-1800.
Rachez, C. et al. "Ligand-dependent transcription activation by nuclear receptors requires the DRIP complex," (1999). Nature, 398: 824-828.
Rachez, C. et al. "Mechanisms of gene regulation by vitamin D3 receptor: a network of coactivator interactions," (2000). Gene, 246(1-2): 9-21.
Reddy, G.S. et al. "Calcitroic Acid, End Product of Renal Metabolism of 1,25-Dihydroxyvitamin D3 through C-24 Oxidation Pathway," (1989). Biochemistry, 28: 1763-1769.
Rees, C.W. et al. "The Condensation of Phthalaldehydic Acid and Related Compounds with Various Heterocyclic Systems," (1965). Journal of the Chemical Society, 687-691.
Rochel, N. et al. "The crystal structure of the nuclear receptor for vitamin D bound to its natural ligand," (2000). Molecular Cell, 5: 173-179.
Rodriguez, A.L. "Design, synthesis, and in vitro biological evaluation of small molecule inhibitors of estrogen receptor alpha coactivator binding," (2004). Journal of Medicinal Chemistry, 47(3): 600-611.
Sadana, P. et al. "Similarities and differences between two modes of antagonism of the thyroid hormone receptor," (2011). ACS Chemical Biology, 6(10): 1096-1106.
Shah, S. et al. "The Molecular Basis of Vitamin D Receptor and b-Catenin Crossregulation," (2006). Molecular Cell, 21: 799-809.
Shaper, W. et al. "Eterocyclic syntheses with monothiomalonamides. Synthesis of 2,3-dihydro-3-oxoisothia7olo[5,4-b]pyridines and [5,4-d]pyrimidines," (1985). Synthesis-Stuttgart, 9: 861-867.
Shuster, I. el al. "Selective inhibitors of CYP24: mechanistic tools to explore vitamin D metabolism in human keratinocytes," (2001). Steroids, 66(3-5): 451-462.
Skowronski, R.J. et al, "Vitamin D and prostate cancer: 1,25 dihydroxyvitamin D3 receptors and actions in human prostate cancer cell lines," (1993). Endocrinology, 132: 1952-1960.
Sone, T. et al, "A 55-kilodalton accessory factor facilitates vitamin D receptor DNA binding," (1991). Molecular Endocrinology, 5(11): 1578-1586.

(56) References Cited

OTHER PUBLICATIONS

Spencer, T.E. et al. "Steroid receptor coactivator-1 is a histone acetyltransferase," (1997). Nature, 389(6647): 194-198.

Stern, P.H. et al. "Evidence for Abnormal Regulation of Circulating 1a,25-Dihydroxyvitamin D in Patients with Sarcoidosis and Normal Calcium Metabolism," (1980). The Journal of Clinical Investigation, 66: 852-855.

Swami, S. et al. "Vitamin D growth inhibition of breast cancer cells: gene expression patterns assessed by cDNA microarray," (2003). Breast Cancer Research and Treatment, 80(1): 49-62.

Tagami, T. et al. "The interaction of the vitamin D receptor with nuclear receptor corepressors and coactivators," (1998). Biochemical and Biophysical Research Communications, 253(2): 358-363.

Teichert, A., et al. "Quantification of the Vitamin D Receptor-Coregulator Interaction," (2009). Biochemistry, 48: 1454-1461.

Toell, A. et al. "All natural DR3-type vitamin D response elements show a similar functionality in vitro," (2000). Biochemical Journal, 352: 301-309.

Towsend, K. et al. "Identification of VDR-responsive gene signatures in breast cancer cells," (2006). Oncology,71(1/2): 111-123.

Vom Baur, E. et al. "Differential ligand-dependent interactions between the AF-2 activating domain of nuclear receptors and the putative transcriptional intermediary factors mSUG1 and TIF1," (1996). The Embo Journal, 15(1): 110-124.

Wei, L. et al. "Receptor-interacting Protein 140 Directly Recruits Histone Deacetylases for Gene Silencing," (2000). The Journal of Biological Chemistry, 275(52): 40782-40787.

Wissenbach, U. et al. "TRPV6 and prostate cancer: cancer growth beyond the prostate correlates with increased TRPV6 Ca2+ channel expression," (2004). Biochemical and Biophysical Research Communications, 322(4): 1359-1363.

Wood, R.J. et al. "DNA microarray analysis of vitamin D-induced gene expression in a human colon carcinoma cell line," (2004). Physiological Genomics, 17: 122-129.

Xie, W. et al. "Lanthanide triflates catalyzed reactions of imines with indole in protic media," (1999). Synlett, 4: 498-500.

Xu, H. E. et al. "Structural basis for antagonist mediated recruitment of nuclear co-repressors by PPARa," (2002). Nature, 45: 813-817.

Yamada, S. et al. "Structure-Function Relationships of Vitamin D Including Ligand Recognition by the Vitamin D Receptor," (2003). Medicinal Research Reviews, 23(1), 89-115.

Yu, et al. Document No. 151:402890, retrieved from STN; entered in STN on Apr. 15, 2009.

Zawisza, T. et al. "Synthesis and properties of some derivatives of 2H-4,6-dimethylpyrido[3,2-d]isothiazolin-3-one-1,1-dioxide," (1986). Farmaco Sci, 41: 676-683.

Zou, A. et al. "Retinoid X receptor (RXR) ligands activate the human 25-hydroxyvitamin D3-24-hydroxylase promoter via RXR heterodimer binding to two vitamin D-responsive elements and elicit additive effects with 1,25-dihydroxyvitamin D3," (1997). The Journal of Biological Chemistry, 272: 19027-19034.

PCT/US2012/052416 International Search Report and Written Opinion dated Jun. 26, 2013 (8 pages).

PCT/US2012/052416 International Preliminary Report on Patentability and Written Opinion of the International Searching Authority dated Mar. 13, 2014 (31pages).

\* cited by examiner

A.

| VDR | | | | | | |
|---|---|---|---|---|---|---|
| SRC2 bead | + | + | + | + | + | - |
| 1,25(OH)2D3 | + | + | + | + | - | + |
| 31b (µM) | 100 | 50 | 1 | - | - | - |

B.

| VDR | | | |
|---|---|---|---|
| SRC2 bead | + | + | + |
| 1,25(OH)2D3 | + | + | + |
| 31b (µM)* | 100 | - | - |
| 32a (µM)* | - | 100 | - |

FIGURE 6

SEQUENCE LISTING

<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
accacagtcc atgccatcac                        20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
tccaccaccc tgttgctgta                        20

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
actgtcattg gggctatcat c                      21

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
cagcagaatc gcatcaggtc                        20

VITAMIN D RECEPTOR-COREGULATOR INHIBITORS

CROSS-REFERENCE TO RELATED APPLICATIONS

This application is a continuation of U.S. patent application Ser. No. 14/240,828, filed Feb. 25, 2014, which application is a national stage filing under 35 U.S.C. 371 of International Patent Application No. PCT/US2012/052416, filed Aug. 26, 2012 which application claims priority to U.S. Provisional Patent Application No. 61/527,780, filed on Aug. 26, 2011, the entire contents of which are hereby incorporated by reference.

BACKGROUND

The vitamin D receptor (VDR) is a nuclear hormone receptor that regulates cell proliferation, cell differentiation, and calcium homeostasis. The receptor contains several functional domains, including a DNA binding domain (VDR-DBD) and a ligand-binding domain (VDR-LBD), which mediates ligand-dependent gene regulation. VDR binds DNA as a heterodimer with the retinoid X receptor (RXR). The receptor is activated by vitamin D analogs that induce the disruption of VDR-corepressor binding and promote VDR-coactivator interactions. The interactions between VDR and coregulators are essential for VDR-mediated transcription.

The gene product of TRPV6 (ECaC2 or CaT1) is a membrane $Ca^{2+}$ ion channel, which is highly expressed in advanced prostate cancer and may be directly regulated by VDR in the presence of $1,25\text{-}(OH)_2D_3$.

SUMMARY

In one aspect, the disclosure provides a compound of formula (I):

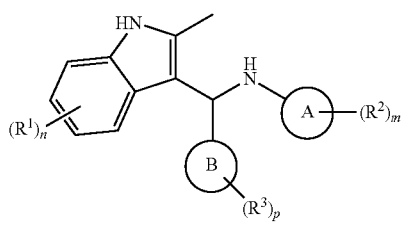

wherein:
m is 0, 1, 2, 3, 4 or 5;
n is 0, 1, 2, 3, or 4;
p is 0, 1, 2, 3, 4 or 5;
each $R^1$, $R^2$ and $R^3$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
A is selected from the group consisting of aryl, heteroaryl and heterocyclyl; and
B is selected from the group consisting of aryl, heteroaryl and heterocyclyl;
wherein the compound is not N-((2-methyl-1H-indol-3-yl)(phenyl)methyl)aniline, N-((2-methyl-1H-indol-3-yl)(2-nitrophenyl)methyl)aniline, N-((4-methoxyphenyl)(2-methyl-1H-indol-3-yl)methyl)-4-methylaniline, 4-methyl-N-((2-methyl-1H-indol-3-yl)(phenyl)methyl)aniline or N-((2-methyl-1H-indol-3-yl)(phenyl)methyl)naphthalen-2-amine;
wherein A is not pyridyl or tetrahydropyranyl;
wherein B is not

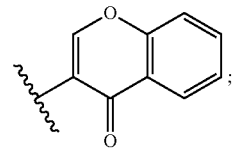 [SMILES: *c1coc2ccccc2c1=O]

and
wherein when B is pyridyl, A is not isoxazolyl or thiazolyl.

In another aspect, the disclosure provides a compound of formula (II):

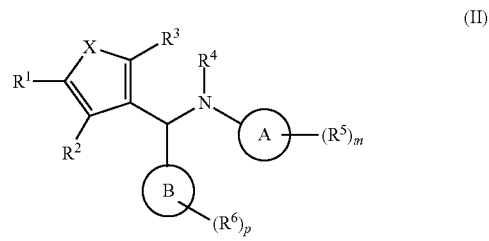

wherein:
m is 0, 1, 2, 3, 4 or 5;
p is 0, 1, 2, 3, 4 or 5;
X is O, S, SO, $SO_2$ or NH;
$R^1$ and $R^2$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido, or $R^1$ and $R^2$ are taken together with the atoms to which they are attached to form an optionally substituted ring;
$R^3$ and $R^4$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
wherein if $R^1$ and $R^2$ are taken together with the atoms to which they are attached to form a phenyl ring, then $R^3$ is not methyl;
each $R^5$ and $R^6$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;

A is selected from the group consisting of aryl, heteroaryl and heterocyclyl; and B is selected from the group consisting of aryl, heteroaryl and heterocyclyl.

In another aspect, the disclosure provides a pharmaceutical composition comprising a compound of formula (III):

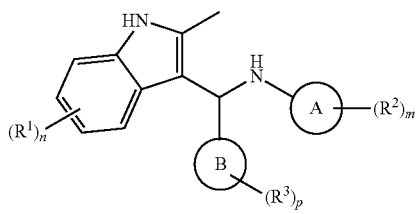

(III)

wherein:
m is 0, 1, 2, 3, 4 or 5;
n is 0, 1, 2, 3, or 4;
p is 0, 1, 2, 3, 4 or 5;
each $R^1$, $R^2$ and $R^3$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;

A is selected from the group consisting of aryl, heteroaryl and heterocyclyl; and B is selected from the group consisting of aryl, heteroaryl and heterocyclyl; wherein A is not pyridyl wherein when B is pyridyl, A is not isoxazolyl or thiazolyl;
and a pharmaceutically acceptable carrier.

In another aspect, the disclosure provides a method of inhibiting the expression of a vitamin D receptor target gene in a sample, comprising contacting the sample with an effective amount of a compound of formula (IV):

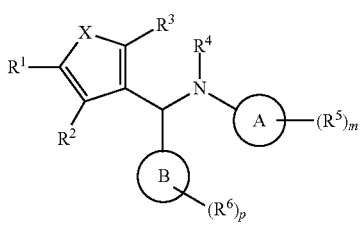

(IV)

wherein:
m is 0, 1, 2, 3, 4 or 5;
p is 0, 1, 2, 3, 4 or 5;
X is O, S, SO, $SO_2$ or NH;
$R^1$ and $R^2$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido, or $R^1$ and $R^2$ are taken together with the atoms to which they are attached to form an optionally substituted ring;

$R^3$ and $R^4$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;

each $R^5$ and $R^6$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;

A is selected from the group consisting of aryl, heteroaryl and heterocyclyl; and B is selected from the group consisting of aryl, heteroaryl and heterocyclyl.

In another aspect, the disclosure provides a method of inhibiting an interaction between a vitamin D receptor and at least one vitamin D receptor coactivator in a sample, comprising contacting the sample with an effective amount of a compound of formula (IV):

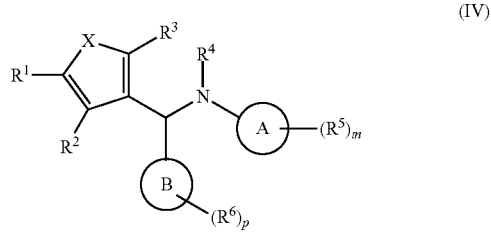

(IV)

wherein:
m is 0, 1, 2, 3, 4 or 5;
p is 0, 1, 2, 3, 4 or 5;
X is O, S, SO, $SO_2$ or NH;
$R^1$ and $R^2$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido, or $R^1$ and $R^2$ are taken together with the atoms to which they are attached to form an optionally substituted ring;

$R^3$ and $R^4$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;

each $R^5$ and $R^6$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;

A is selected from the group consisting of aryl, heteroaryl and heterocyclyl; and B is selected from the group consisting of aryl, heteroaryl and heterocyclyl.

In another aspect, the disclosure provides a method of treating cancer in a subject in need of treatment, comprising administering to the subject a therapeutically effective amount of a compound of formula (IV):

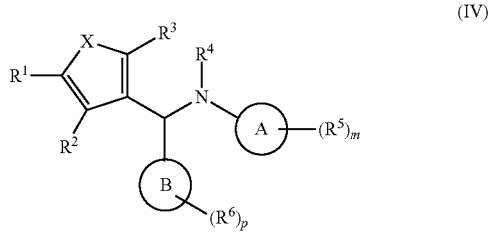

(IV)

wherein:
m is 0, 1, 2, 3, 4 or 5;
p is 0, 1, 2, 3, 4 or 5;
X is O, S, SO, SO$_2$ or NH;
R$^1$ and R$^2$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido, or R$^1$ and R$^2$ are taken together with the atoms to which they are attached to form an optionally substituted ring;
R$^3$ and R$^4$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
each R$^5$ and R$^6$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
A is selected from the group consisting of aryl, heteroaryl and heterocyclyl; and
B is selected from the group consisting of aryl, heteroaryl and heterocyclyl.

In another aspect, the disclosure provides a method of inhibiting angiogenesis in a subject in need thereof, comprising administering to the subject a therapeutically effective amount of a compound of formula (IV):

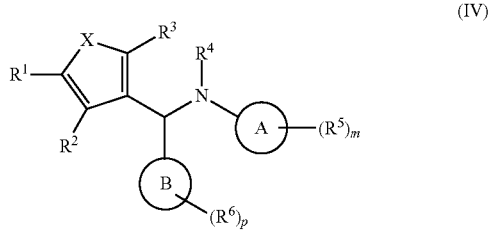

(IV)

wherein:
m is 0, 1, 2, 3, 4 or 5;
p is 0, 1, 2, 3, 4 or 5;
X is O, S, SO, SO$_2$ or NH;

R$^1$ and R$^2$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido, or R$^1$ and R$^2$ are taken together with the atoms to which they are attached to form an optionally substituted ring;
R$^3$ and R$^4$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
each R$^5$ and R$^6$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
A is selected from the group consisting of aryl, heteroaryl and heterocyclyl; and
B is selected from the group consisting of aryl, heteroaryl and heterocyclyl.

In some embodiments, of the methods described herein, the compound of formula (IV) has the following formula (V):

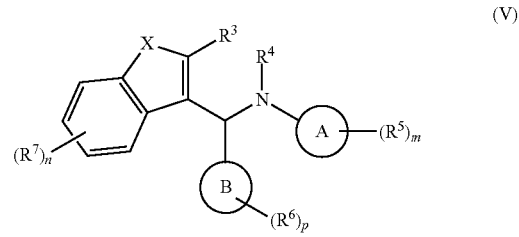

(V)

wherein:
n is 0, 1, 2, 3, or 4; and
each R$^7$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido.

Other aspects and embodiments will become apparent in light of the following description and drawings.

BRIEF DESCRIPTION OF THE DRAWINGS

FIG. 6 shows Western blots showing: A) results of a pull-down assay to determine in vitro binding interactions between SRC2 bearing all three nuclear interaction domains (NIDs) and VDR-LBD in the presence of compound 31b. Lanes 1-3: different concentrations of 31b in the presence of VDR, SRC2 and 1,25(OH)$_2$D$_3$; lane 4 VDR, SRC2 and 1,25(OH)$_2$D$_3$; lane 5 no ligand (1,25(OH)$_2$D$_3$); lane 6 no coregulator (SRC2). B) in vitro binding reactions between SRC2 bearing all three NIDs and compound 31b or 32a. Lane 1 pre-incubation SRC2 with 31b; Lane 2 pre-incubation with 32a; and lane 3 pre-incubation with vehicle only.

DETAILED DESCRIPTION

Figure 1:
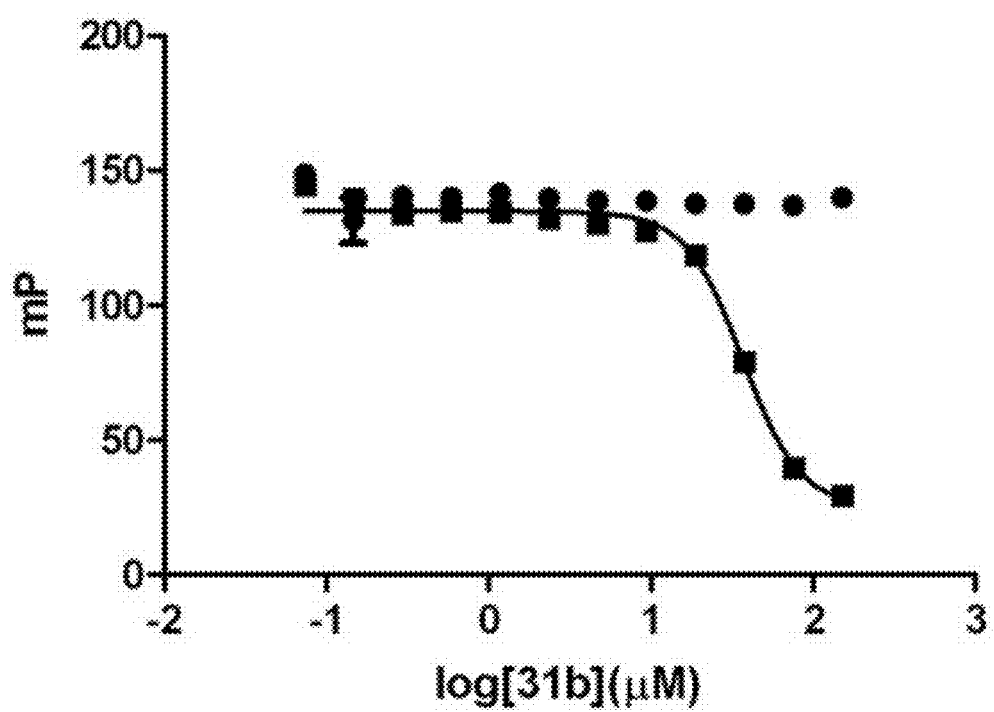
FIG. 1 shows fluorescence polarization binding isotherms following incubation of varying concentrations of compound 31b with either Alexa Fluor-labeled SRC2-3 peptide for 3 hours followed by addition of VDR-LBD and LG190178 (●), or incubation of varying concentrations of compound 31b with VDR-LBD (1 μM) and LG190178 (5 μM) for 3 hours followed by the addition of Alexa Fluor-labeled SRC2-3 peptide (■). Fluorescence polarization was detected after 5 minutes.

Described herein are compounds and pharmaceutical compositions that may irreversibly inhibit interactions between the vitamin D receptor (VDR) and its coactivators. VDR is a ligand-activated transcription factor that belongs to the nuclear receptor (NR) superfamily. VDR binds to its endogenous ligand, 1,25-dihydroxyvitamin D$_3$ (1,25-(OH)$_2$D$_3$), with high affinity, mediating the modulation of genes responsible for cell differentiation, proliferation, and calcium homeostasis.

In the unliganded state, VDR is associated with corepressor proteins, which repress transcription of VDR target genes. In the presence of 1,25-(OH)$_2$D$_3$, the VDR-LBD undergoes a conformational change. This conformational change prevents corepressor binding and permits interactions with coactivator proteins, resulting in the formation of a multi-protein complex that activates VDR-mediated transcription.

Small molecule inhibition of VDR-coregulator binding represents an alternative method to the traditional ligand-based approach in order to modulate the expression of VDR target genes. While some VDR ligand antagonists have been shown to allosterically inhibit interactions between VDR and its coactivators, compounds described herein may irreversibly and selectively inhibit VDR-coactivator interactions. The compounds may thus have the ability to modulate VDR-mediated transcription of target genes such as TRPV6.

1. Definitions

The terminology used herein is for the purpose of describing particular embodiments only and is not intended to be limiting. As used in the specification and the appended claims, the singular forms "a," "and" and "the" include plural references unless the context clearly dictates otherwise.

Section headings as used in this section and the entire disclosure herein are not intended to be limiting.

For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

As used herein, the term "about" is used synonymously with the term "approximately." Illustratively, the use of the term "about" indicates that values slightly outside the cited values, namely, plus or minus 10%. Such values are thus encompassed by the scope of the claims reciting the terms "about" and "approximately."

The terms "administer", "administering", "administered" or "administration" refer to any manner of providing a compound or a pharmaceutical composition (e.g., one described herein), to a subject or patient. Routes of administration can be accomplished through any means known by those skilled in the art. Such means include, but are not limited to, oral, buccal, intravenous, subcutaneous, intramuscular, transdermal, by inhalation and the like.

"Contacting" as used herein, e.g., as in "contacting a sample" refers to contacting a sample directly or indirectly in vitro, ex vivo, or in vivo (i.e. within a subject as defined herein). Contacting a sample may include addition of a compound to a sample, or administration to a subject. Contacting encompasses administration to a solution, cell, tissue, mammal, subject, patient, or human. Further, contacting a cell includes adding an agent to a cell culture.

"Effective amount," as used herein, refers to a dosage or an amount of a compound or a composition effective for eliciting a desired effect. This term as used herein may also refer to an amount effective at bringing about a desired in vivo effect in an animal, e.g., a mammal, e.g., a human. For example, in methods of treating cancer, an effective amount may be an amount sufficient to treat the disorder.

"Inhibit" or "inhibiting," as used herein, e.g., as in "inhibiting an interaction" between two binding partners such as proteins, refers to a process of lowering or reducing the ability of a first protein and a second protein to bind or associate, or disrupting an interaction between a first protein and a second protein. "Inhibiting an interaction" between two proteins may involve disrupting one or more covalent or non-covalent interactions between the first protein and the second protein. Covalent bonding interactions between proteins include, for example, disulfide bonds, ester bonds, amide bonds and the like. Non-covalent bonding interactions between proteins include, for example, hydrophobic interactions, van der Waals interactions, ionic interactions, hydrogen bonding interactions and the like. In the context of inhibiting angiogenesis, the term "inhibiting" means reducing the formation or outgrowth of blood or lymph vessels, or destroying such vessels during sprouting or outgrowth.

"Reduce" or "reducing," as used herein, e.g., as in "reducing the expression" of a target gene, means that the expression of a target gene in a sample that has been contacted with a compound described herein is lower than the expression in a sample that has not been contacted with the compound. For example, if expression of a target gene is reduced in a sample that has been contacted with a compound, the expression may be about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or 100% lower than in a sample that has not been contacted with a compound. Expression of a target gene may be reduced 1-fold, 2-fold, 3-fold, 4-fold, 5-fold, 6-fold, 7-fold, 8-fold, 9-fold, 10-fold or more.

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

As used herein, the term "treat" or "treating" a subject having a disorder refers to administering a compound or a composition described herein to the subject, such that at least one symptom of the disorder is healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder.

Definitions of specific functional groups and chemical terms are described in more detail below. For purposes of this disclosure, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; *Smith and March March's Advanced Organic Chemistry*, $5^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, $3^d$ Edition, Cambridge University Press, Cambridge, 1987; the entire contents of each of which are incorporated herein by reference.

The term "acyl" refers to an alkylcarbonyl, cycloalkylcarbonyl, heterocyclylcarbonyl, arylcarbonyl or heteroarylcarbonyl substituent, any of which may be further substituted (e.g., with one or more substituents).

The term "alkyl" refers to a straight or branched saturated hydrocarbon chain. Alkyl groups may include a specified number of carbon atoms. For example, $C_1$-$C_{12}$ alkyl indicates that the alkyl group may have 1, 2, 3, 4, 5, 6, 7, 8, 9, 10, 11 or 12 carbon atoms. An alkyl group may be, e.g., a $C_1$-$C_{12}$ alkyl group, a $C_1$-$C_{10}$ alkyl group, a $C_1$-$C_8$ alkyl group, a $C_1$-$C_6$ alkyl group or a $C_1$-$C_4$ alkyl group. For example, exemplary $C_1$-$C_4$ alkyl groups include methyl, ethyl, n-propyl, isopropyl, n-butyl, sec-butyl, isobutyl and tert-butyl groups. An alkyl group may be optionally substituted with one or more substituents.

The term "alkenyl" refers to a straight or branched hydrocarbon chain having one or more double bonds. Alkenyl groups may include a specified number of carbon atoms. For example, $C_2$-$C_{12}$ alkenyl indicates that the alkenyl group may have 2, 3, 4, 5, 6, 7, 8, 9, 10, 11 or 12 carbon atoms. An alkenyl group may be, e.g., a $C_2$-$C_{12}$ alkenyl group, a $C_2$-$C_{10}$ alkenyl group, a $C_2$-$C_8$ alkenyl group, a $C_2$-$C_6$ alkenyl group or a $C_2$-$C_4$ alkenyl group. Examples of alkenyl groups include but are not limited to allyl, propenyl, 2-butenyl, 3-hexenyl and 3-octenyl groups. One of the double bond carbons may optionally be the point of attachment of the alkenyl substituent. An alkenyl group may be optionally substituted with one or more substituents.

The term "alkynyl" refers to a straight or branched hydrocarbon chain having one or more triple bonds. Alkynyl groups may include a specified number of carbon atoms. For example, $C_2$-$C_{12}$ alkynyl indicates that the alkynyl group may have 2, 3, 4, 5, 6, 7, 8, 9, 10, 11 or 12 carbon atoms. An alkynyl group may be, e.g., a $C_2$-$C_{12}$ alkynyl group, a $C_2$-$C_{10}$ alkynyl group, a $C_2$-$C_8$ alkynyl group, a $C_2$-$C_6$ alkynyl group or a $C_2$-$C_4$ alkynyl group. Examples of alkynyl groups include but are not limited to ethynyl, propargyl, and 3-hexynyl. One of the triple bond carbons may optionally be the point of attachment of the alkynyl substituent. An alkynyl group may be optionally substituted with one or more substituents.

The term "aryl" refers to an aromatic monocyclic, bicyclic, or tricyclic hydrocarbon ring system, wherein any ring atom capable of substitution can be substituted (e.g., with one or more substituents). Examples of aryl moieties include but are not limited to phenyl, naphthyl, and anthracenyl. Aryl groups may be optionally substituted with one or more substituents.

The term "arylalkyl" refers to an alkyl moiety in which at least one alkyl hydrogen atom is replaced with an aryl group. Arylalkyl includes groups in which more than one hydrogen atom has been replaced with an aryl group. Examples of arylalkyl groups include but are not limited to benzyl, 2-phenylethyl, 3-phenylpropyl, 9-fluorenyl, benzhydryl, and trityl groups. Arylalkyl groups may be optionally substituted with one or more substituents, on either the aryl moiety or the alkyl moiety.

The term "cycloalkyl" as used herein refers to non-aromatic, saturated or partially unsaturated cyclic, bicyclic, tricyclic or polycyclic hydrocarbon groups having 3 to 12 carbons. Any ring atom can be substituted (e.g., with one or more substituents). Cycloalkyl groups can contain fused rings. Fused rings are rings that share one or more common carbon atoms. Examples of cycloalkyl groups include but are not limited to cyclopropyl, cyclobutyl, cyclopentyl, cyclohexyl, cyclohexenyl, cyclohexadienyl, methylcyclohexyl, adamantyl, norbornyl, norbornenyl, tetrahydronaphthalenyl and dihydroindenyl. Cycloalkyl groups may be optionally substituted with one or more substituents.

The term "halo" or "halogen" as used herein refers to any radical of fluorine, chlorine, bromine or iodine.

The term "haloalkyl" as used herein refers to an alkyl group as defined herein, such as a $C_1$-$C_4$ alkyl group, in which one or more hydrogen atoms are replaced with halogen atoms, and includes alkyl moieties in which all hydrogens have been replaced with halogens (e.g., perfluoroalkyl such as $CF_3$).

The term "heteroaryl" as used herein refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms independently selected from O, N, S, P and Si (e.g., carbon atoms and 1-3, 1-6, or 1-9 heteroatoms independently selected from O, N, S, P and Si if monocyclic, bicyclic, or tricyclic, respectively). Any ring atom can be substituted (e.g., with one or more substituents). Heteroaryl groups can contain fused rings, which are rings that share one or more common atoms. Examples of heteroaryl groups include but are not limited to radicals of pyridine, pyrimidine, pyrazine, pyridazine, pyrrole, imidazole, pyrazole, oxazole, isoxazole, furan, thiazole, isothiazole, thiophene, quinoline, isoquinoline, quinoxaline, quinazoline, cinnoline, indole, isoindole, indolizine, indazole, benzimidazole, phthalazine, pteridine, carbazole, carboline, phenanthridine, acridine, phenanthroline, phenazine, naphthyridines and purines. Heteroaryl groups may be optionally substituted with one or more substituents.

The term "heteroatom", as used herein, refers to a non-carbon or hydrogen atom such as a nitrogen, sulfur, oxygen, silicon or phosphorus atom. Groups containing more than one heteroatom may contain different heteroatoms.

The term "heterocyclyl", as used herein, refers to a nonaromatic, saturated or partially unsaturated 3-10 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, S, Si and P (e.g., carbon atoms and 1-3, 1-6, or 1-9 heteroatoms of O, N, S, Si and P if monocyclic, bicyclic, or tricyclic, respectively). Any ring atom can be substituted (e.g., with one or more substituents). Heterocyclyl groups can contain fused rings, which are rings that share one or more common atoms. Examples of heterocyclyl groups include but are not limited to radicals of tetrahydrofuran, tetrahydrothiophene, tetrahydropyran, oxetane, piperidine, piperazine, morpholine, pyrroline, pyrimidine, pyrrolidine, indoline, tetrahydropyridine, dihydropyran, thianthrene, pyran, benzopyran, xanthene, phenoxathiin, phenothiazine, furazan, lactones, lactams such as azetidinones and pyrrolidinones, sultams, sultones, and the like. Heterocyclyl groups may be optionally substituted with one or more substituents.

The term "hydroxy" refers to an —OH radical. The term "alkoxy" refers to an —O-alkyl radical. The term "aryloxy" refers to an —O-aryl radical. The alkyl portion of an alkoxy group or the aryl portion of an aryloxy group may be optionally substituted with one or more substituents. (For example, "alkoxy" encompasses hydroxyalkoxy groups, in which the alkyl portion of the alkoxy group is substituted with a hydroxy group.)

The term "oxo" refers to an oxygen atom, which forms a carbonyl when attached to carbon, an N-oxide when attached to nitrogen, and a sulfoxide or sulfone when attached to sulfur (i.e. =O).

The term "mercapto" or "thiol" refers to an —SH radical. The term "thioalkoxy" or "thioether" refers to an —S-alkyl radical. The term "thioaryloxy" refers to an —S-aryl radical.

The term "substituents" refers to a group "substituted" on an alkyl, alkenyl, alkynyl, cycloalkyl, heterocyclyl, aryl, arylalkyl, heteroaryl or heteroarylalkyl group at any atom of that group. Any atom can be substituted. Suitable substituents include, without limitation: acyl, acylamido, acyloxy, alkoxy, alkyl, alkenyl, alkynyl, amido, amino, carboxy, cyano, ester, halo, haloalkyl, hydroxy, imino, nitro, oxo (e.g., C=O), phosphonate, sulfinyl, sulfonyl, sulfonate, sulfonamino, sulfonamido, thioamido, thiol, thioxo (e.g., C=S), and ureido. In some embodiments, substituents on a group are independently any one single, or any combination of the aforementioned substituents. In some embodiments, a substituent may itself be substituted with any one of the above substituents.

The above substituents may be abbreviated herein. For example, the abbreviations Me, Et, Ph and Bn represent methyl, ethyl, phenyl and benzyl, respectively. A more comprehensive list of standard abbreviations used by organic chemists appears in a table entitled Standard List of Abbreviations of the Journal of Organic Chemistry. The abbreviations contained in said list are hereby incorporated by reference.

For compounds described herein, groups and substituents thereof may be selected in accordance with permitted valence of the atoms and the substituents, and such that the selections and substitutions result in a stable compound, e.g., a compound that does not spontaneously undergo transformation such as by rearrangement, cyclization, elimination, etc.

Where substituent groups are specified by their conventional chemical formulae, written from left to right, they optionally encompass substituents resulting from writing the structure from right to left, e.g., —CH$_2$O— optionally also recites —OCH$_2$—.

In accordance with a convention used in the art, the group:

is used in structural formulae herein to depict the bond that is the point of attachment of the moiety or substituent to the core or backbone structure.

2. Compounds

The disclosure provides compounds of formulae (I), (II), (III), (IV) and (V), which may be used in methods described herein or included in pharmaceutical compositions described herein. A compound may have the following formula (I):

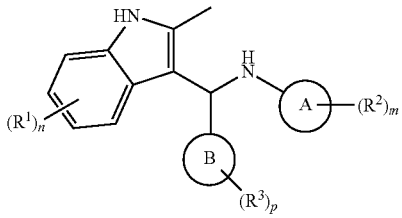

wherein:
m is 0, 1, 2, 3, 4 or 5;
n is 0, 1, 2, 3, or 4;
p is 0, 1, 2, 3, 4 or 5;
each $R^1$, $R^2$ and $R^3$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
A is selected from the group consisting of aryl, heteroaryl and heterocyclyl; and
B is selected from the group consisting of aryl, heteroaryl and heterocyclyl;
wherein the compound is not N-((2-methyl-1H-indol-3-yl)(phenyl)methyl)aniline, N-((2-methyl-1H-indol-3-yl)(2-nitrophenyl)methyl)aniline, N-((4-methoxyphenyl)(2-methyl-1H-indol-3-yl)methyl)-4-methylaniline, 4-methyl-N-((2-methyl-1H-indol-3-yl)(phenyl)methyl)aniline or N-((2-methyl-1H-indol-3-yl)(phenyl)methyl)naphthalen-2-amine;
wherein A is not pyridyl or tetrahydropyranyl;
wherein B is not

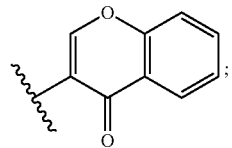 [SMILES: *c1coc2ccccc2c1=O]

and
wherein when B is pyridyl, A is not isoxazolyl or thiazolyl.

In some embodiments, n is 0. In some embodiments, A is phenyl. In some embodiments, m is 0. In some embodiments, m is 1. In some embodiments, $R^2$ is selected from the group consisting of alkyl (e.g., $C_1$-$C_4$ alkyl, such as methyl, ethyl or isopropyl), alkoxy (e.g., $C_1$-$C_4$ alkoxy, such as methoxy, or a substituted $C_1$-$C_4$ alkoxy, such as 3-hydroxypropoxy), amino (e.g., —$NH_2$, alkylamino or dialkylamino, such as dimethylamino), halo (e.g., fluoro, chloro or bromo), haloalkyl (e.g., $C_1$-$C_4$ haloalkyl, such as trifluoromethyl) and nitro. In some embodiments, B is phenyl. In some embodiments, p is 0. In some embodiments, p is 1. In some embodiments, $R^3$ is selected from the group consisting of alkyl (e.g., $C_1$-$C_4$ alkyl, such as methyl, ethyl or isopropyl), alkoxy (e.g., $C_1$-$C_4$ alkoxy, such as methoxy, or a substituted $C_1$-$C_4$ alkoxy, such as 3-hydroxypropoxy), amino (e.g., —$NH_2$, alkylamino or dialkylamino, such as dimethylamino), halo (e.g., fluoro, chloro or bromo), haloalkyl (e.g., $C_1$-$C_4$ haloalkyl, such as trifluoromethyl) and nitro.

A compound may have the following formula (II):

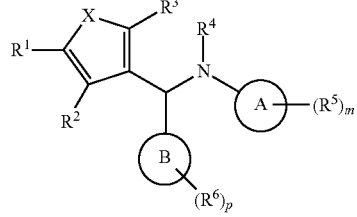

wherein:
m is 0, 1, 2, 3, 4 or 5;
p is 0, 1, 2, 3, 4 or 5;
X is O, S, SO, $SO_2$ or NH;
$R^1$ and $R^2$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido, or $R^1$ and $R^2$ are taken together with the atoms to which they are attached to form an optionally substituted ring;
$R^3$ and $R^4$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
wherein if $R^1$ and $R^2$ are taken together with the atoms to which they are attached to form a phenyl ring, then $R^3$ is not methyl;
each $R^5$ and $R^6$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
A is selected from the group consisting of aryl, heteroaryl and heterocyclyl; and
B is selected from the group consisting of aryl, heteroaryl and heterocyclyl.

In some embodiments, $R^3$ is alkyl (e.g., methyl). In some embodiments, $R^4$ is hydrogen. In some embodiments, A is phenyl. In some embodiments, B is phenyl.

A compound may have the following formula (III):

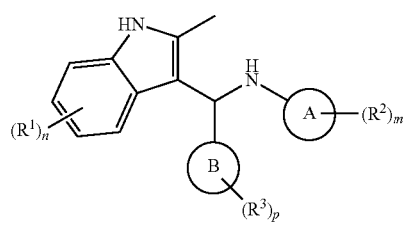

wherein:
m is 0, 1, 2, 3, 4 or 5;
n is 0, 1, 2, 3, or 4;
p is 0, 1, 2, 3, 4 or 5;
each $R^1$, $R^2$ and $R^3$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
A is selected from the group consisting of aryl, heteroaryl and heterocyclyl; and
B is selected from the group consisting of aryl, heteroaryl and heterocyclyl; wherein A is not pyridyl
wherein when B is pyridyl, A is not isoxazolyl or thiazolyl.

In some embodiments, n is 0. In some embodiments, A is phenyl. In some embodiments, m is 0. In some embodiments, m is 1. In some embodiments, $R^2$ is selected from the group consisting of alkyl (e.g., $C_1$-$C_4$ alkyl, such as methyl, ethyl or isopropyl), alkoxy (e.g., $C_1$-$C_4$ alkoxy, such as methoxy, or a substituted $C_1$-$C_4$ alkoxy, such as 3-hydroxypropoxy), amino (e.g., —$NH_2$, alkylamino or dialkylamino, such as dimethylamino), halo (e.g., fluoro, chloro or bromo), haloalkyl (e.g., $C_1$-$C_4$ haloalkyl, such as trifluoromethyl) and nitro. In some embodiments, B is phenyl. In some embodiments, p is 0. In some embodiments, p is 1. In some embodiments, $R^3$ is selected from the group consisting of alkyl (e.g., $C_1$-$C_4$ alkyl, such as methyl, ethyl or isopropyl), alkoxy (e.g., $C_1$-$C_4$ alkoxy, such as methoxy, or a substituted $C_1$-$C_4$ alkoxy, such as 3-hydroxypropoxy), amino (e.g., —$NH_2$, alkylamino or dialkylamino, such as dimethylamino), halo (e.g., fluoro, chloro or bromo), haloalkyl (e.g., $C_1$-$C_4$ haloalkyl, such as trifluoromethyl) and nitro.

A compound may have the following formula (IV):

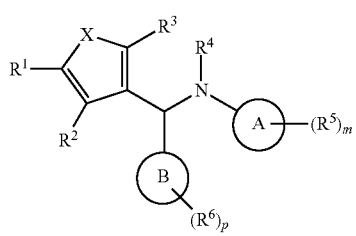

(IV)

wherein:
m is 0, 1, 2, 3, 4 or 5;
p is 0, 1, 2, 3, 4 or 5;
X is O, S, SO, $SO_2$ or NH;
$R^1$ and $R^2$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido, or $R^1$ and $R^2$ are taken together with the atoms to which they are attached to form an optionally substituted ring;
$R^3$ and $R^4$ are independently selected from the group consisting of hydrogen, alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
each $R^5$ and $R^6$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido;
A is selected from the group consisting of aryl, heteroaryl and heterocyclyl; and
B is selected from the group consisting of aryl, heteroaryl and heterocyclyl.

A compound of formula (IV) may have the following formula (V):

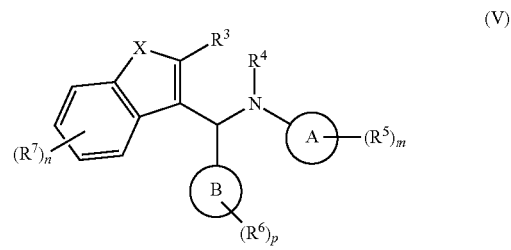

(V)

wherein:
n is 0, 1, 2, 3, or 4; and
each $R^7$ is independently selected from the group consisting of alkyl, alkenyl, alkynyl, aryl, heteroaryl, cycloalkyl, heterocyclyl, acyl, acylamido, acyloxy, alkoxy, amido, amino, carboxy, cyano, ester, halo, haloalkyl, hydroxy, imino, nitro, phosphonate, sulfinyl, sulfonyl, sulfonate, sulfonamino, sulfonamido, thioamido, thiol, and ureido.

In some embodiments, $R^3$ is methyl. In some embodiments, $R^4$ is hydrogen. In some embodiments, n is 0. In some embodiments, A is phenyl. In some embodiments, m is 0. In some embodiments, m is 1. In some embodiments, $R^5$ is selected from the group consisting of alkyl (e.g., $C_1$-$C_4$ alkyl, such as methyl, ethyl or isopropyl), alkoxy (e.g., $C_1$-$C_4$ alkoxy, such as methoxy, or a substituted $C_1$-$C_4$ alkoxy, such as 3-hydroxypropoxy), amino (e.g., —$NH_2$, alkylamino or dialkylamino, such as dimethylamino), halo (e.g., fluoro, chloro or bromo), haloalkyl (e.g., $C_1$-$C_4$ haloalkyl, such as trifluoromethyl) and nitro. In some embodiments, A is pyridyl. In some embodiments, B is phenyl. In some embodiments, p is 0. In some embodiments, p is 1. In some embodiments, $R^6$ is selected from the group consisting of alkyl (e.g., $C_1$-$C_4$ alkyl, such as methyl, ethyl or isopropyl), alkoxy (e.g., $C_1$-$C_4$ alkoxy, such as methoxy, or a substituted $C_1$-$C_4$ alkoxy, such as 3-hydroxypropoxy), amino (e.g., —$NH_2$, alkylamino or dialkylamino, such as dimethylamino), halo (e.g., fluoro, chloro or bromo), haloalkyl (e.g., $C_1$-$C_4$ haloalkyl, such as trifluoromethyl) and nitro.

In some embodiments, X is NH.

In some embodiments, a compound is selected from the group consisting of:
N-((2-methyl-1H-indol-3-yl)(phenyl)methyl)aniline;
N-((4-chlorophenyl)(2-methyl-1H-indol-3-yl)methyl)aniline;
N-((4-methoxyphenyl)(2-methyl-1H-indol-3-yl)methyl)aniline;
N-((2-methyl-1H-indol-3-yl)(p-tolyl)methyl)aniline;

N,N-dimethyl-4-((2-methyl-1H-indol-3-yl)(phenylamino) methyl)aniline N-((2-methyl-1H-indol-3-yl)(4-nitrophenyl)methyl)aniline;

N-(1-(2-methyl-1H-indol-3-yl)ethyl)aniline;

N-((2-methyl-1H-indol-3-yl)(naphthalen-2-yl)methyl)aniline;

3-(4-((2-methyl-1H-indol-3-yl)(phenylamino)methyl)phenoxy)propan-1-ol;

N-((2-chlorophenyl)(2-methyl-1H-indol-3-yl)methyl)aniline;

4-chloro-N-((2-chlorophenyl)(2-methyl-1H-indol-3-yl) methyl)aniline;

N-((2-chlorophenyl)(2-methyl-1H-indol-3-yl)methyl)-4-methoxyaniline;

N-((2-chlorophenyl)(2-methyl-1H-indol-3-yl)methyl)-4-methylaniline $N^1$-((2chlorophenyl)(2-methyl-1H-indol-3-yl)methyl)-$N^4$,$N^4$-dimethylbenzene-1,4-diamine;

N-((2-chlorophenyl)(2-methyl-1H-indol-3-yl)methyl)-4-nitro aniline;

N-((2-chlorophenyl)(2-methyl-1H-indol-3-yl)(phenyl) methyl)-4-(trifluoromethyl)aniline;

N-((2-chlorophenyl)(2-methyl-1H-indol-3-yl)methyl)-2-methoxyaniline; and

N-((2-chlorophenyl)(1H-indol-3-yl)methyl)aniline.

a. Preparation of Compounds

Compounds described herein may be prepared according to a variety of methods. A representative synthesis of exemplary compounds of formula (I) is illustrated in Scheme 1.

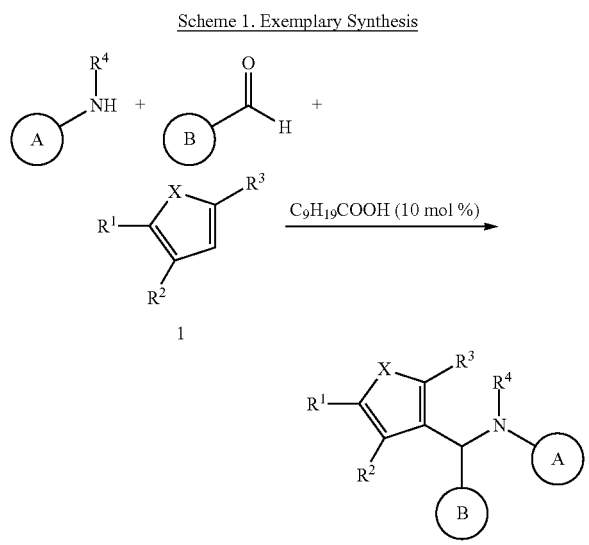

Scheme 1. Exemplary Synthesis

The reaction illustrated in Scheme 1 is known as an aza-Friedel-Crafts reaction. In an exemplary synthesis, the aniline A-NH—$R^4$ may be first stirred with the compound B—CHO in a 1:1 ratio in a solvent. The solvent may be any suitable solvent, including but not limited to water, dimethylformamide, dimethyl sulfoxide, acetonitrile, tetrahydrofuran, 1,4-dioxane, dichloromethane, chloroform and toluene. In some embodiments, the solvent may be toluene. (Groups A and B may correspond to the groups as defined in the claims, and may include optional substituents.) Compound 1 may then be added along with a suitable acid (e.g., decanoic acid) in an amount of, e.g., 5-30 mol %, in a solvent such as, e.g., toluene. The progress of the reaction can be monitored using any suitable method, such as thin-layer chromatography (TLC). Following completion, the reaction may be quenched using a base (e.g., sodium bicarbonate) and the product may be extracted using an organic solvent. Washing and drying of the organic phase can be followed by removal of the solvent and purification using a variety of methods such as recrystallization or chromatography.

As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P.G.M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents or Organic Synthesis, John Wiley and Sons (1995), and subsequent editions thereof.

b. Isomers

Certain compounds may exist in one or more particular geometric, optical, enantiomeric, diastereomeric, epimeric, atropic, stereoisomer, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and half chair-forms; and combinations thereof, hereinafter collectively referred to as "isomers" (or "isomeric forms").

In one embodiment, a compound described herein may be an enantiomerically enriched isomer of a stereoisomer described herein. For example, the compound may have an enantiomeric excess of at least about 10%, 15%, 20%, 25%, 30%, 35%, 40%, 45%, 50%, 55%, 60%, 65%, 70%, 75%, 80%, 85%, 90%, 95%, 96%, 97%, 98%, or 99%. Enantiomer, when used herein, refers to either of a pair of chemical compounds whose molecular structures have a mirror-image relationship to each other.

In one embodiment, a preparation of a compound disclosed herein is enriched for an isomer of the compound having a selected stereochemistry, e.g., R or S, corresponding to a selected stereocenter. For example, the compound has a purity corresponding to a compound having a selected stereochemistry of a selected stereocenter of at least about 60%, 65%, 70%, 75%, 80%, 85%, 90%, 95%, 96%, 97%, 98%, or 99%.

In one embodiment, a composition described herein includes a preparation of a compound disclosed herein that is enriched for a structure or structures having a selected stereochemistry, e.g., R or S, at a selected stereocenter. Exemplary R/S configurations can be those provided in an example described herein.

An "enriched preparation," as used herein, is enriched for a selected stereoconfiguration of one, two, three or more selected stereocenters within the subject compound. Exemplary selected stereocenters and exemplary stereoconfigurations thereof can be selected from those provided herein, e.g., in an example described herein. By enriched is meant at least 60%, e.g., of the molecules of compound in the preparation have a selected stereochemistry of a selected stereocenter. In an embodiment it is at least 65%, 70%, 75%, 80%, 85%, 90%, 95%, 96%, 97%, 98%, or 99%. Enriched refers to the level of a subject molecule(s) and does not connote a process limitation unless specified.

Compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

Except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_3$-alkyl or propyl includes n-propyl and iso-propyl; $C_4$-alkyl or butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hydroxyazo, and nitro/aci-nitro.

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

c. Salt Forms

A compound described herein can be in the form of a salt, e.g., a pharmaceutically acceptable salt. The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds or separately by reacting a compound with a suitable acid or base, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts." *J. Pharm. Sci.* Vol. 66, pp. 1-19.

Representative acid addition salts can be prepared using various suitable acids for example, including, but are not limited to, acetic, adipic, alginic, citric, aspartic, benzoic, benzenesulfonic, butyric, camphoric, camphorsulfonic, carbonic, digluconic, glycerophosphoric, heptanoic, hexanoic, fumaric, hydrochloric, hydrobromic, hydroiodic, 2-hydroxyethansulfonic (isethionic), lactic, maleic, methanesulfonic, nicotinic, 2-naphthalenesulfonic, oxalic, pamoic, pectinic, persulfuric, 3-phenylpropionic, picric, pivalic, propionic, succinic, sulfuric, tartaric, thiocyanic, phosphoric, glutamatic, p-toluenesulfonic, and undecanoic acids.

Particular examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, tartaric acid, and citric acid.

Basic addition salts can be prepared in situ during the final isolation and purification of compounds by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

Also, the basic nitrogen-containing groups can be quatemized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Unless otherwise specified, a reference to a particular compound also includes salt forms thereof.

d. Chemically Protected Forms

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective*

Groups in Organic Synthesis (T. Green and P. Wuts; 3rd Edition; John Wiley and Sons, 1999). Unless otherwise specified, a reference to a particular compound also includes chemically protected forms thereof.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(O)CH$_3$, —OAc).

An aldehyde or ketone group may be protected as an acetal (RCH(OR)$_2$) or ketal (R$_2$C(OR)$_2$), respectively, in which the carbonyl group (R$_2$C=O) is converted to a diether (R$_2$C(OR)$_2$), by reaction with, for example, a primary alcohol. The aldehyde or ketone group is readily regenerated by hydrolysis using an excess of water in the presence of acid.

An amine group may be protected, for example, as an amide (—NRC(O)R) or a urethane (—NRC(O)OR), for example, as: a methyl amide (—NHC(O)CH$_3$); a benzyloxy amide (—NHC(O)OCH$_2$C$_6$H$_5$, —NH-Cbz); as a t-butoxy amide (—NHC(O)OC(CH$_3$)$_3$, —NH-Boc); a 2-biphenyl-2-propoxy amide (—NHCO(O)C(CH$_3$)$_2$C$_6$H$_4$C$_6$H$_5$, —NH-Bpoc), as a 9-fluorenylmethoxy amide (—NH—Fmoc), as a 6-nitroveratryloxy amide (—NH—Nvoc), as a 2-trimethylsilylethyloxy amide (—NH—Teoc), as a 2,2,2-trichloroethyloxy amide (—NH-Troc), as an allyloxy amide (—NH-Alloc), as a 2-(phenylsulfonyl)ethyloxy amide (—NH—Psec); or, in suitable cases (e.g., cyclic amines), as a nitroxide radical.

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; or an acetamidomethyl ether (—S—CH$_2$NHC(O)CH$_3$).

e. Prodrugs and Other Modifications

In addition to salt forms, the present disclosure may also provide compounds that are in a prodrug form. Prodrugs of the compounds described herein are those compounds that readily undergo chemical changes under physiological conditions to provide the compounds described herein. The term "pharmaceutically acceptable prodrug" or "prodrug," as used herein, represents those prodrugs of the compounds which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the disclosure can be rapidly transformed in vivo to a parent compound, for example, by hydrolysis. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include but are not limited to esterification with polyethylene glycols, derivatization with pivolates or fatty acid substituents, conversion to carbamates, hydroxylation of aromatic rings, and heteroatom substitution in aromatic rings.

f. Evaluation of Compounds

Following synthesis, compounds can be evaluated using a number of techniques. Following structural characterization using, for example, nuclear magnetic resonance (NMR) spectroscopy and mass spectrometry (MS), compounds can be evaluated for properties such as solubility and cell permeability. Solubility may be determined in buffered solutions at different pH values, such as pH values normally found in various parts of the body (e.g., pH 2.0 (stomach), 6.0 (small intestine), and 7.2 (blood)). The amount of the parent compound and identity of any new compounds formed can be determined by liquid chromatography-mass spectrometry (LCMS) for different time ranges.

Compound stabilities can also be evaluated. For example, the stabilities of compounds can be determined in blood plasma, liver microsomes, and/or hepatocytes (e.g., mouse plasma, microsomes or hepatocytes). The amount of the parent compound and identity of any new compounds formed can be determined by liquid chromatography-mass spectrometry (LCMS) for different time ranges.

To identify whether compounds act as VDR-coactivator inhibitors that regulate VDR-mediated transcription, a fluorescence resonance energy transfer (FRET) transcription assay can be performed. Kits for performing such assays may be commercially available, such as the GeneBLAzer® assay (Invitrogen). For example, cells can be engineered to express a fusion protein of VDR-LBD and the GAL4-DBD, which would be activated by 1,25-(OH)$_2$D$_3$ to induce transcription of a β-lactamase reporter gene. Quantification of β-lactamase can accomplished by detecting the decrease in FRET caused by enzymatic cleavage of a β-lactam-containing substrate, which was added after an incubation time of 24 hours. If a compound inhibits a VDR-coactivator interaction, transcription of β-lactamase should decrease.

Expression of target genes of interest may be evaluated, for example, using semi-quantitative real time polymerase chain reaction (PCR). For example cells can be incubated with a compound of interest in the presence or absence of 20 nM calcitriol for 18 h. Total RNA can be isolated from cells, for example using an RNAeasy kit (QIAGEN®). Genomic DNA can be removed and cDNA was generated using equal amounts of RNA (e.g., using a QuantiTect® Reverse Transcription Kit, QIAGEN®). The cDNA reaction can be diluted, and a kit such as a QuantiFast® SYBR Green PCR Kit (QIAGEN®) can be used for the real time PCR.

The ability of a compound to disrupt binding of VDR and its coactivators may be determined using fluorescence polarization assays. Fluorescence polarization (or fluorescence anisotropy) is the phenomenon where the light emitted by a fluorophore has unequal intensities along different axes of polarization. Fluorescence polarization (FP) can be used to measure the binding constants and kinetics of reactions that cause a change in the rotational time of the molecules. If the fluorophore is bound to a small molecule, the rate at which it tumbles can decrease significantly when it is bound tightly to a larger molecule such as a peptide or protein. The degree of binding can be calculated by using the difference in anisotropy of the partially bound, free and fully bound (large excess of binding partner) states measured by titrating the two binding partners.

It has been established that the third nuclear interaction domain (NID) of steroid receptor coactivator 2 (SRC2), called SRC2-3, has the strongest interaction with VDR among other coregulator peptides tested (Teichert et al. *Biochemistry* 2009, 48, 1454-1461). It has also been established that binding affinities of SRC2 peptides were similar in the presence of either 1,25-$(OH)_2D_3$ or synthetic agonist LG190178 (Teichert et al.; Boehm et al. *Chem Biol* 1999, 6, 265-275). Accordingly, a suitable FP assay to assess whether a compound described herein disrupts the binding of VDR and its coactivator may be as follows. VDR-LBD, LG190178, and Alexa Fluor 647 labeled SRC2-3 may be incubated together along with a compound of interest. FP can measured after incubation for a period of time (e.g., about 3 hours). If the compound of interest does not disrupt the binding of VDR-LBD and the labeled SRC2-3, no change in FP would be expected. By contrast, if a compound does disrupt the binding, a change in FP should be observed due to the increase in the rate of tumbling of the released, labeled SRC2-3 peptide. If a compound does inhibit the VDR-LBD/SRC2-3 interaction, the interaction can subsequently be quantified.

Compounds showing promising characteristics can be further evaluated for their cytotoxicities toward various cancer cell lines, and for their activity in various in vivo cancer models (e.g., mouse models). Certain such experiments are described further in the Examples section below.

3. Pharmaceutical Compositions

The disclosure also provides pharmaceutical compositions comprising a compound of formula (I), (II), (III), (IV) or (V), and a pharmaceutically acceptable carrier. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions can be administered to subjects (e.g., humans and other mammals) orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrastemal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions can also contain adjuvants such as preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. It also can be desirable to include isotonic agents, for example, sugars, sodium chloride and the like. Prolonged absorption of the injectable pharmaceutical form can be brought about by the use of agents delaying absorption, for example, aluminum monostearate and gelatin.

In some cases, in order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions can be formulated according to the known art using suitable dispersing or wetting agents and suspending agents. The sterile injectable preparation also can be a sterile injectable solution, suspension or emulsion in a nontoxic, parenterally acceptable diluent or solvent such as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well-known in the pharmaceutical formulating art. They can optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Dosage forms for topical or transdermal administration of a compound include ointments, pastes, creams, lotions, gels, powders, solutions, sprays, inhalants or patches. A desired compound is admixed under sterile conditions with a pharmaceutically acceptable carrier and any needed preservatives or buffers as may be required. Ophthalmic formulation, eardrops, eye ointments, powders and solutions are also contemplated as being within the scope of this disclosure.

The ointments, pastes, creams and gels may contain, in addition to an active compound, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds, lactose, talc, silicic acid, aluminum hydroxide, calcium silicates and polyamide powder, or mixtures of these substances. Sprays can additionally contain customary propellants such as chlorofluorohydrocarbons.

Compounds also can be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds, stabilizers, preservatives, and the like. The preferred lipids are the natural and synthetic phospholipids and phosphatidylcholines (lecithins) used separately or together. Methods to form liposomes are known in the art. See, for example, Prescott, Ed., Methods in Cell Biology, Volume XIV, Academic Press, New York, N.Y., (1976), p 33 et seq.

Dosage forms for topical administration of a compound described herein include powders, sprays, ointments and inhalants. The active compound is mixed under sterile conditions with a pharmaceutically acceptable carrier and any needed preservatives, buffers or propellants. Ophthalmic formulations, eye ointments, powders and solutions are also contemplated as being within the scope of this disclosure. Aqueous liquid compositions may also be useful.

3. Methods of Use

Compounds of formulae (I), (II), (III), (IV) and (V) may be used in a variety of methods, such as in a method of inhibiting the expression of a vitamin D receptor target gene in a sample, a method of inhibiting an interaction between the vitamin D receptor and at least one vitamin D receptor coactivator in a sample, a method treating cancer in a subject, or a method of inhibiting angiogenesis in a subject.

a. Methods of Inhibiting Expression of VDR Target Genes

In some embodiments, compounds described herein can be used in methods of inhibiting the expression of a VDR target gene in a sample. The compounds may inhibit the interaction of VDR with its coactivators, which may thereby inhibit transcription of the target gene.

The methods include the step of contacting the sample with an effective amount of a compound (e.g., a compound of formula (I), (II), (III), (IV) or (V)) to inhibit the expression of the target gene. Expression levels can be evaluated using methods described herein, such as semi-quantitative real-time PCR. Expression levels may also be evaluated indirectly such as, for example, by testing for an activity of the target gene.

In some embodiments, the methods described herein may inhibit expression of a VDR target gene. Such genes include but are not limited to 15-PGDH, 216518_at, AADAC, ABC1, ADRA2A, ALOX5, ALPL, AMACR, ANGPT1, ANK2, APOE, APX1, B15, B4, B4GALT1, BARD1, BAT2D1, BMP4, BMP7, c/EBPδ, CALD1, CASP4, CCNA1, CCNG2, CD14, CD24, CD33, CDK5, CES1, CFTR, C1orf29, CLU, CNGB1, COL13A1, COL15A1, connexin 43, CP, CPN2, CRABP2, CRIP1, CSDT1, CSPG6, CST6, CTDSPL, CYP19A1, CYP24A1, CYP2B6, CYP3A7, DTNA, EDNRB, ENPP1, ERBB3, FBLN2, FK506, FKBP3, FKBP5, FLJ11800, FLJ14054, FN1, FOS, FOXA1, GOS2, GATA3, GHRHR, HDAC9, HSD17B2, ID1, ID3, IGF1, IGFBP1, IGFBP2, IGFBP3, IGFBP4, IGFBP5, IGFBP7, IL1, IL1B, IL1F15, IL1RL1, IL1RN, IL24, IL6, IL8, INHBA, IκBα, KLK6, LALB, LAMB3, LOC16911, MAP1, MAP4, MAPK13, MCAM, MFI2, MRP, MRPL33, MYB, NAT1, NCOA3, NDRG1, NR4A2, NRCAM, NRG1, OGN, OMD, OSF-2, OXTR, P8, PLAB, PLN, PMP70, POV1, PPAP2B, PPARG, PTGDR, PTGES2, PTGS1, PTGS2, PTPRF, RARRES1, SEMA3B, SERINB1, SERPINE1, SOCS2, SOD3, SON, SPAG11, SPIB, SPP1, SUMO1, TCF8, TFAP2C, TGFB3, TGFBR2, TGIF, THBD, THBS1, TIMP3, TNFRSF11B, TNXB, TREM1, TRP, TRPV6, UGT2, VCL, VEGF, VTN, W11, XPC and YY1. In some embodiments, the target gene is TRPV6.

Expression of a target gene in a sample may be inhibited/reduced by at least or up to about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98% or 99%, or any range therebetween. The $IC_{50}$ for transcription inhibition of a target gene may be about 1 nM to about 100 μM, e.g., up to about 1 nM, about 0.1 μM, about 0.2 μM, about 0.3 μM, about 0.4 μM, about 0.5 μM, about 0.6 μM, about 0.7 μM, about 0.8 μM, about 0.8 μM, about 1 μM, about 2 μM, about 3 μM, about 4 μM, about 5 μM, about 6 μM, about 7 μM, about 8 μM, about 9 μM, about 10 μM, about 11 μM, about 12 μM, about 13 μM, about 14 μM, about 15 μM, about 16 μM, about 17 μM, about 18 μM, about 19 μM, about 20 μM, about 21 μM, about 22 μM, about 23 μM, about 24 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM or about 100 μM.

b. Methods of Inhibiting Interactions Between VDR and Coactivators

In some embodiments, compounds described herein can be used in methods of inhibiting an interaction between VDR and at least one VDR coactivator in a sample. The methods include the step of contacting the sample with an effective amount of a compound (e.g., a compound of formula (I), (II), (III), (IV) or (V)) to inhibit the interaction between VDR and the at least one VDR coactivator. Interactions between VDR and coactivators may be determined, for example, using a fluorescence polarization assay.

In some embodiments, the VDR coactivator is selected from the group consisting of Akt, ARA55, ARA70, β-catenin, BRCA1, BRCA2, BRG1, Calreticulin, CARM1, CAV1, CBP, CDC-25B, CDK7, CFL1, CITED1, CoAA, Cyclin A1, Cyclin A2, Cyclin 1, Cyclin D3, Cyclin E1, DAP3, Daxx, DJ-1, DNAJB1, DRIP130, E6-AP, ELL, FKHR, Fli-1, FLNa, Gelsolin, HDAC3, HDAC4, HMG-1, HMG-2, JAB1, Ku80, LATS2/KPM, MGMT, MLL2, MN1, MTA1, MTA2, MUC1, N—CoR, NSD1, p-TEFb, p53, p54nrb, p57, p68, p300, PAD4, PARP-1, PCAF, PDEF, PDK1, PGC-1a, PGC-1β, PELP1, PIAS1, PIAS3, PIAS4, PIN1, PPM1D, PRAME, PUS1, RACK1, RAF1, RANBP2, Rb, REA, REG, SAF-A, SAP30, SENP1, Six3, SNURF, SRA, SRC-1, SRC-2, SRC-3, SRY, STAT3, SUMO-1, SYT, TBL1, TBP, TDG, TGIF, TLS, TRAP100, TRAP220, TRRAP, TSG101, UBC9, VAV3, and WSTF.

Interactions between VDR and coactivators may be determined using full-length proteins or portions thereof. For example, for evaluating inhibition of an interaction between VDR and SRC-2, an assay may use VDR-LBD and a peptide such as SRC2-3.

The $IC_{50}$ for inhibition of an interaction between VDR and a coactivator may be about 1 nM to about 100 μM, e.g., up to about 1 nM, about 0.1 μM, about 0.2 μM, about 0.3 μM, about 0.4 μM, about 0.5 μM, about 0.6 μM, about 0.7 μM, about 0.8 μM, about 0.8 μM, about 1 μM, about 2 μM, about 3 μM, about 4 μM, about 5 μM, about 6 μM, about 7 μM, about 8 μM, about 9 μM, about 10 μM, about 11 μM, about 12 μM, about 13 μM, about 14 μM, about 15 μM, about 16 μM, about 17 μM, about 18 μM, about 19 μM, about 20 μM, about 21 μM, about 22 μM, about 23 μM, about 24 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM or about 100 μM.

The dissociation constant of VDR from a coactivator may be about 1 nM to about 100 μM, e.g., up to about 1 nM, about 0.1 μM, about 0.2 μM, about 0.3 μM, about 0.4 μM, about 0.5 μM, about 0.6 μM, about 0.7 μM, about 0.8 μM, about 0.8 μM, about 1 μM, about 2 μM, about 3 μM, about 4 μM, about 5 μM, about 6 μM, about 7 μM, about 8 μM, about 9 μM, about 10 μM, about 11 μM, about 12 μM, about 13 μM, about 14 μM, about 15 μM, about 16 μM, about 17 μM, about 18 μM, about 19 μM, about 20 μM, about 21 μM, about 22 μM, about 23 μM, about 24 μM, about 25 μM, about 30 μM, about 35 μM, about 40 μM, about 45 μM, about 50 μM, about 55 μM, about 60 μM, about 65 μM, about 70 μM, about 75 μM, about 80 μM, about 85 μM, about 90 μM, about 95 μM or about 100 μM.

c. Methods of Treating Cancer

In some embodiments, a compound described herein can be used in a method of treating a proliferative disorder such as cancer in a subject in need of treatment. The method comprises administering to the subject a therapeutically effective amount of a compound described herein, such as a compound of formula (I), (II), (III), (IV) or (V), or a pharmaceutical composition comprising a compound of formula (I), (II), (III), (IV) or (V).

With respect to proliferative disorders defined as cancers, the cancer may be any type of cancer, such as a cancer recognized by the National Cancer Institute. In some embodiments, the cancer may be a type of cancer associated with increased expression of a VDR target gene, such as TRPV6. Exemplary types of cancers include ovarian cancer (e.g., epithelial ovarian cancer), prostate cancer, endometrial cancer, breast cancer and colorectal cancer. The cancer may be a metastatic cancer, a chemoresistant phenotype, or a recurrent phenotype of a cancer.

In some embodiments, a compound described herein can be used in a method of inhibiting angiogenesis in a subject in need thereof. The method comprises administering to the subject a therapeutically effective amount of a compound described herein, such as a compound of formula (I), (II), (III), (IV) or (V), or a pharmaceutical composition comprising a compound of formula (I), (II), (III), (IV) or (V).

In the methods of treating cancer and inhibiting angiogenesis, a compound, or a pharmaceutical composition comprising the compound, may be administered to the subject by any convenient route of administration, whether systemically/peripherally or at the site of desired action, including but not limited to, oral (e.g. by ingestion); topical (including e.g. transdermal, intranasal, ocular, buccal, and sublingual); pulmonary (e.g. by inhalation or insufflation therapy using, e.g. an aerosol, e.g. through mouth or nose); rectal; vaginal; parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Additional modes of administration may include adding the compound and/or a composition comprising the compound to a food or beverage, including a water supply for an animal, to supply the compound as part of the animal's diet.

It will be appreciated that appropriate dosages of the compounds, and compositions comprising the compounds, can vary from patient to patient. Determining the optimal dosage will generally involve the balancing of the level of therapeutic benefit against any risk or deleterious side effects of the treatments of the present invention. The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

Administration in vivo can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the treating physician. In general, a suitable dose of the compound is in the range of about 100µg to about 250 mg per kilogram body weight of the subject per day.

The compound or composition may be administered once, on a continuous basis (e.g. by an intravenous drip), or on a periodic/intermittent basis, including about once per hour, about once per two hours, about once per four hours, about once per eight hours, about once per twelve hours, about once per day, about once per two days, about once per three days, about twice per week, about once per week, and about once per month. The composition may be administered until a desired reduction of symptoms is achieved.

The present compounds, compositions, and methods may be administered as part of a therapeutic regimen along with other treatments appropriate for the particular disease being treated.

i. Cancer Combination Therapy

A compound described herein may be used in combination with other known therapies. Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound described herein and the at least one additional therapeutic agent can be administered simultaneously, in the same or in separate compositions, or sequentially. For sequential administration, the compound described herein can be administered first, and the additional agent can be administered subsequently, or the order of administration can be reversed.

In some embodiments, a compound described herein is administered in combination with other therapeutic treatment modalities, including surgery, radiation, cryosurgery, and/or thermotherapy. Such combination therapies may advantageously utilize lower dosages of the administered agent and/or other chemotherapeutic agent, thus avoiding possible toxicities or complications associated with the various therapies. The phrase "radiation" includes, but is not limited to, external-beam therapy which involves three dimensional, conformal radiation therapy where the field of radiation is designed to conform to the volume of tissue treated; interstitial-radiation therapy where seeds of radioactive compounds are implanted using ultrasound guidance; and a combination of external-beam therapy and interstitial-radiation therapy.

In some embodiments, the compound described herein is administered with at least one additional therapeutic agent, such as a chemotherapeutic agent. In certain embodiments, the compound described herein is administered in combination with one or more additional chemotherapeutic agents. Examples of categories of chemotherapeutic agents that may be used as an additional active ingredient include but are not limited to DNA damaging agents such as topoisomerase inhibitors (e.g., etoposide, camptothecin, topotecan, irrinotecan, teniposide, mitoxantrone), anti-microtubule agents (e.g., vincristine, vinblastine), antimetabolites (e.g., cytarabine, methotrexate, hydroxyurea, 5-fluorouracil, flouridine, 6-thioguanine, 6-mercaptompurine, fludarabine, pentostatin, cholorodeoxyadenosine), DNA alkylating agents (e.g., cisplatin, mecholorethamine, cyclophosphamide, ifosphamide, melphalan, chlorumbucil, busulfan, thiotepa, carmustine, lomustine, carboplatin, dacarbazine, procarbazine) and DNA strand break inducing agents (e.g., bleomycin, doxarubicine, daunorubicine, idarubicine, mitomycin C).

Chemotherapeutic agents include synthetic, semisynthetic and naturally derived agents. Important chemotherapeutic agents include, but are not limited to: 2,2',2"-trichlorotriethylamine; 20-epi-1,25 dihydroxyvitamin D3; 2-ethylhydrazide; 5-ethynyluracil; 6-azauridine; 6-diazo-5-oxo-1-norleucine; 6-mercaptopurine; abiraterone; aceglatone; acivicin; aclacinomycins; aclarubicin; acodazole hydrochloride; acronine; actinomycin; acylfulvene; adecypenol; adozelesin; aldesleukin; aldophosphamide glycoside; all-trans retinoic acid; ALL-TK antagonists; altretamine; ambamustine; ambomycin; ametantrone acetate; amidox; amifostine; aminoglutethimide; aminolevulinic acid; amrubicin; amsacrine; anagrelide; anastrozole; ancitabine; andrographolide; angiogenesis inhibitors; antagonist D; antagonist G; antarelix; anthramycin; antiandrogen, prostatic carcinoma; antidorsalizing morphogenetic protein-1; antiestrogen; antineoplaston; antisense oligonucleotides; aphidicolin glycinate; apoptosis gene modulators; apoptosis regulators; apurinic acid; ara-CDP-DL-PTBA; arginine deaminase; asparaginase; asperlin; asulacrine; atamestane; atrimustine; axinastatin 1; axinastatin 2; axinastatin 3; azacitidine; azaserine; azasetron; azathiopurine; azatoxin; azatyrosine; azetepa; azotomycin; baccatin III derivatives; balanol; batimastat; BCR/ABL antagonists; benzochlorins; benzodepa; benzoylstaurosporine; bestrabucil; beta lactam derivatives; betaalethine; betaclamycin B; betulinic acid; bFGF inhibitor; bicalutamide; bisantrene; bisantrene hydrochloride; bisaziridinylspermine; bisnafide; bisnafide dimesylate; bistratene A; bizelesin; bleomycin; bleomycin sulfate; bortezomib; breflate; brequinar sodium; bropirimine; budotitane; busulfan; buthionine sulfoximine; cactinomycin; calcipotriol; calphostin C; calusterone; camptothecin derivatives; canarypox IL-2; capecitabine; caracemide; carbetimer; carboplatin; carboquone; carboxamide-amino-triazole; carboxyamidotriazole; CaRest M3; carmofur; carmustine; CARN 700; cartilage derived inhibitor; carubicin; carubicin hydrochloride; carzelesin; carzinophilin; casein kinase inhibitors (ICOS); castanospermine; cecropin B; cedefingol; cetrorelix; chlorambucil; chlomaphazine; chloroquinoxaline sulfonamide; chlorozotocin; chromomycin; cicaprost; cirolemycin; cisplatin; cisporphyrin; cladribine; clomifene analogues; clotrimazole; collismycin A; collismycin B; combretastatin A4; combretastatin analogue; conagenin; crambescidin 816; crisnatol; crisnatol mesylate; cryptophycin 8; cryptophycin A derivatives; curacin A; cyclopentanthraquinones; cyclophosphamide; cycloplatam; cypemycin; cytarabine; cytarabine ocfosfate; cytolytic factor; cytostatin; dacarbazine; dacliximab; dactinomycin; daunomycin; daunorubicin; daunorubicin hydrochloride; decitabine; defofamide; dehydrodidemnin B; demecolcine; denopterin; deslorelin; dexamethasone; dexifosfamide; dexormaplatin; dexrazoxane; dexverapamil; dezaguanine; dezaguanine mesylate; diaziquone; didemnin B; dideoxyuridine; didox; diethylnorspermine; dihydro-5-azacytidine; dihydrotaxol, 9-; dioxamycin; diphenyl spiromustine; docetaxel; docosanol; dolasetron; doxifluridine; doxorubicin; doxorubicin hydrochloride; droloxifene; droloxifene citrate; dromostanolone propionate; dronabinol; duazomycin; duocarmycin SA; ebselen; ecomustine; edatrexate; edelfosine; edrecolomab; eflomithine; eflomithine hydrochloride; elemene; elfomithine; elliptinium acetate; elsamitrucin; emitefur; enloplatin; enocitabine; enpromate; epipropidine; epirubicin; epirubicin hydrochloride; epothilone; epristeride; erbulozole; esorubicin hydrochloride; estermustine; estramustine analogue; estramustine phosphate sodium; estrogen agonists; estrogen antagonists; etanidazole; etoglucid; etoposide; etoposide phosphate; etoprine; exemestane; fadrozole; fadrozole hydrochloride; fazarabine; fenretinide; filgrastim; finasteride; flavopiridol; flezelastine; floxuridine; fluasterone; fludarabine; fludarabine phosphate; fluorodaunorunicin hydrochloride; fluorouracil; flurocitabine; flutamide; forfenimex; formestane; fosquidone; fostriecin; fostriecin sodium; fotemustine; gadolinium texaphyrin; gallium nitrate; galocitabine; ganirelix; gelatinase inhibitors; gemcitabine; gemcitabine hydrochloride; gemzar; glutathione inhibitors; hepsulfam; heregulin; hexamethylene bisacetamide; hydroxyurea; hypericin; ibandronic acid; idarubicin; idarubicin hydrochloride; idoxifene; idramantone; ifosfamide; ilmofosine; ilomastat; imatinib; imidazoacridones; imiquimod; immunostimulant peptides; improsulfan; insulin-like growth factor-1 receptor inhibitor; interferon agonists; interferon alfa-2a; interferon alfa-2b; interferon alfa-n3; interferon alfa-nl; interferon beta-I a; interferon gamma-I b; interferons; interleukin II (including recombinant interleukin II, or rIL2); interleukins; iobenguane; iododoxorubicin; ipomeanol, 4-; iproplatin; irinotecan hydrochloride; iroplact; irsogladine; isobengazole; isohomohalicondrin B; itasetron; jasplakinolide; kahalalide F; lamellarin-N triacetate; lanreotide; lanreotide acetate; leinamycin; lenograstim; lentinan; lentinan sulfate; leptolstatin; letrozole; leukemia inhibiting factor; leukocyte alpha interferon; leuprolide acetate; leuprolide+estrogen+progesterone; leuprorelin; levamisole; liarozole; liarozole hydrochloride; linear polyamine analogue; lipophilic disaccharide peptide; lipophilic platinum compounds; lissoclinamide 7; lobaplatin; lombricine; lometrexol; lometrexol sodium; lomustine; lonidamine; losoxantrone; losoxantrone hydrochloride; lovastatin; loxoribine; lurtotecan; lutetium texaphyrin; lysofylline; lytic peptides; maitansine; mannomustine; mannostatin A; marimastat; masoprocol; maspin; matrilysin inhibitors; matrix metalloproteinase inhibitors; maytansine; mechlorethamine; mechlorethamine oxide hydrochloride; megestrol acetate; melengestrol acetate; melphalan; menogaril; merbarone; mercaptopurine; meterelin; methioninase; methotrexate; methotrexate sodium; metoclopramide; metoprine; meturedepa; MIF inhibitor; mifepristone; miltefosine; mirimostim; mismatched double stranded RNA; mitindomide; mitobronitol; mitocarcin; mitocromin; mitogillin; mitoguazone; mitolactol; mitomalcin; mitomycin; mitomycin analogues; mitonafide; mitosper; mitotane; mitotoxin fibroblast growth factor-saporin; mitoxantrone; mitoxantrone hydrochloride; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; mycophenolic acid; myriaporone; N-acetyldinaline; nafarelin; nagrestip; naloxone+pentazocine; napavin; naphterpin; nartograstim; nedaplatin; nemorubicin; neridronic acid; neutral endopeptidase; nilutamide; nimustine; nisamycin; nitric oxide modulators; nitroxide antioxidant; nitrullyn; nocodazole; nogalamycin; novembichin; N-substituted benzamides; O6-benzylguanine; octreotide; okicenone; oligonucleotides; olivomycin; onapristone; ondansetron; oracin; oral cytokine inducer; ormaplatin; osaterone; oxaliplatin; oxaunomycin; oxisuran; paclitaxel; palauamine; palmitoylrhizoxin; pamidronic acid; panaxytriol; panomifene; parabactin; pazelliptine; pegaspargase; peldesine; peliomycin; pemetrexed; pentamustine; pentosan polysulfate sodium; pentostatin; pentrozole; peplomycin sulfate; perflubron; perfosfamide; perillyl alcohol; phenamet; phenazinomycin; phenesterine; phenylacetate; phosphatase inhibitors; picibanil; pilocarpine hydrochloride; pipobroman; piposulfan; pirarubicin; piritrexim; piroxantrone hydrochloride; placetin A; placetin B; plasminogen activator inhibitor; platinum complex; platinum compounds; platinum-triamine complex; plicamycin; plomestane; podophyllinic acid; porfimer sodium; porfiromycin; prednimustine; prednisone; procarbazine hydrochloride; propyl bis-acridone; prostaglandin J2; proteasome inhibitors; protein A-based immune modulator; protein kinase C inhibitor; protein kinase C inhibitors, microalgal; protein tyrosine phosphatase inhibitors; pteropterin; pulmozyme; purine nucleoside phosphorylase inhibitors; puromycin; puromycin hydrochloride; purpurins; pyrazofurin; pyrazoloacridine; pyridoxylated hemoglobin polyoxyethylene conjugate; raf antagonists; raltitrexed; ramosetron; ranimustine; ras farnesyl protein transferase inhibitors; ras inhibitors; ras-GAP inhibitor; razoxane; retelliptine demethylated; rethamine hydrochloride; rhenium Re 186 etidronate; rhizoxin; riboprine; ribozymes; RII retinamide; rogletimide; rohitukine; romurtide; roquinimex; rubiginone B1; ruboxyl; safingol; safingol hydrochloride; saintopin; SarCNU; sarcophytol A; sargramostim; Sdi 1 mimetics; semustine; senescence derived inhibitor 1; sense oligonucleotides; signal transduction inhibitors; signal transduction modulators; simtrazene; single chain antigen binding protein; sizofiran; sobuzoxane; sodium borocaptate; sodium phenylacetate; solverol; somatomedin binding protein; sonermin; sparfosate sodium; sparfosic acid; sparsomycin; spicamycin D; spirogermanium; spirogermanium hydrochloride; spiromustine; spiroplatin; splenopentin; spongistatin 1; squalamine; stem cell inhibitor; stem-cell division inhibitors; stipiamide; streptonigrin; streptozocin; stromelysin inhibitors; sulfinosine; sulofenur; superactive vasoactive intestinal peptide antagonist; suradista; suramin; swainsonine; synthetic glycosaminoglycans; talisomycin; tallimustine; tamoxifen; tamoxifen methiodide; tauromustine; taxel; taxel analogues; taxel derivatives; taxotere; tazarotene; tecogalan sodium; tegafur; tellurapyrylium; telomerase inhibitors; teloxantrone hydrochloride; temoporfin; temozolomide; teniposide; tenuazonic acid; teroxirone; testolactone; tetrachlorodecaoxide; tetrazomine; thaliblastine; thiamiprine; thiocoraline; thioguanine; thiotepa; thrombopoietin; thrombopoietin mimetic; thymalfasin; thymopoietin receptor agonist; thymotrinan; thyroid stimulating hormone; tiazofurin; tin ethyl etiopurpurin; tioguanine; tirapazamine; titanocene bichloride; topsentin; toremifene; toremifene citrate; totipotent stem cell factor; translation inhibitors; trestolone acetate; tretinoin; triacetyluridine; triaziquone; triciribine; triciribine phosphate; triethylenemelamine; triethylenephosphoramide; triethylenethiophosphoramide; trimethylolomelamine; trimetrexate; trimetrexate glucuronate; triptorelin; trofosfamide; tropisetron; tubercidin; tubulozole hydrochloride; turosteride; tyrosine kinase inhibitors; tyrphostins; UBC inhibitors; ubenimex; uracil mustard; uredepa; urethan; urogenital sinus-derived growth inhibitory factor; urokinase receptor antagonists; valrubicin; vapreotide; variolin B; vector system, erythrocyte gene therapy; velaresol; veramine; verdins; verteporfin; vinblastine; vinblastine sulfate; vincristine; vincristine sulfate; vindesine; vindesine and related agents; vindesine sulfate; vinepidine sulfate; vinglycinate sulfate; vinleurosine sulfate; vinorelbine; vinorelbine tartrate; vinrosidine sulfate; vinxaltine; vinzolidine sulfate; vitaxin; vorozole; zanoterone; zeniplatin; zilascorb; zinostatin; zinostatin stimalamer; zorubicin; and zorubicin hydrochloride. For example, suitable chemotherapeutic agents include, but are not limited to, actinomycin, all-trans retinoic acid, azacitidine, azathiopurine, bleomycin, bortezomib, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tioguanine, valrubicin, vinblastine, vincristine, vindesine, and vinorelbine.

e. Methods of Inhibiting Angiogenesis

In some embodiments, a compound described herein can be used in a method of inhibiting angiogenesis in a subject in need thereof. The method comprises administering to the subject a therapeutically effective amount of a compound described herein, such as a compound of formula (I), (II), (III), (IV) or (V), or a pharmaceutical composition comprising a compound of formula (I), (II), (III), (IV) or (V).

Methods of inhibiting angiogenesis may reduce the formation or outgrowth of blood or lymph vessels, or destroy such vessels during sprouting or outgrowth. The angiogenic or antiangiogenic effects of compounds described herein can determined using in vitro, ex-vivo and in vivo methods. For example, in vitro analysis of angiogenic or anti-angiogenic effects may be evaluated in cells, such as human umbilical vein endothelial (HUVEC) cells grown in culture. Kits available for evaluation of such effects are commercially available (e.g., from Trevigen®, MD, USA. Cat No-3470-096-K). Tube formation output can be analyzed by microscopy after staining with, e.g., Calcien AM. A suitable ex vivo model may be a rat aorta model, and a suitable in vivo model may involve VEGFR and PECAM-1 staining of xenografts of cancer cell lines in nude animals (e.g., mice).

4. Kits

In another aspect, the disclosure provides a kit, which may be used for inhibiting the expression of a vitamin D receptor target gene in a sample, inhibiting an interaction between the vitamin D receptor and at least one vitamin D receptor coactivator in a sample, or treating cancer in a subject.

A kit will include a compound of formula (I), (II), (III), (IV) and/or (V) as described herein. A kit may also include instructions for use of the compound. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD, DVD), and the like. As used herein, the term "instructions" can include the address of an internet site that provides the instructions.

In one embodiment, the disclosure provides a kit for inhibiting the expression of a vitamin D receptor target gene in a sample, inhibiting an interaction between the vitamin D receptor and at least one vitamin D receptor coactivator in a sample. The kit comprises at least one compound of formula (I), (II), (III), (IV) and/or (V), and instructions for assaying the test sample for VDR target gene inhibition or VDR-coactivator interaction inhibition. For example, the kit can comprise instructions for assaying the test sample using, e.g., a fluorescence polarization assay. The kit may further comprise a calibrator or control, which may be purified and optionally lyophilized, and/or at least one container (e.g., tube, microtiter plates or strips) for conducting the assay, and/or a buffer, such as an assay buffer or a wash buffer, either one of which can be provided as a concentrated solution. Preferably, the kit comprises all components, i.e., reagents, standards, buffers, diluents, etc., which are necessary to perform the assay. The instructions also can include instructions for generating a standard curve or a reference standard for purposes of quantifying inhibition.

The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a blood sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

It will be readily apparent to those skilled in the art that other suitable modifications and adaptations of the compounds, pharmaceutical compositions and methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples which are merely intended only to illustrate some aspects and embodiments of the disclosure, and should not be viewed as limiting to the scope of the disclosure. The disclosures of all journal references, U.S. patents and publications referred to herein are hereby incorporated by reference in their entireties.

EXAMPLES

General Experimental and Analytical Details

All materials were obtained from commercial suppliers and used without further purification. All solvents used were dried using an aluminum oxide column. Thin-layer chromatography was performed on precoated silica gel 60 F254 plates. Purification of compounds was carried out by normal phase column chromatography (SP1 [Biotage], Silica gel 230-400 mesh) followed by evaporation. Purity determination were performed by element analysis (EA1110, Carlo-Erba) or using a LC-MS (Surveyor&MSQ) with a C18 column. The total flow rate was 1.0 mL/min and gradient program started at 90% A (0.1% formic acid in H2O), changed to 95% B (0.1% formic acid in methanol), and then to 90% A. The mass spectrometer was operated in positive-ion mode with electrospray ionization. All compounds presented were confirmed at 95% purity or better using either method. NMR spectra are recorded on a Bruker 400 MHz and referenced internally to the residual resonance in $CDCl_3$ ($\delta$) 7.26 ppm) for hydrogen and ($\delta$) 77 ppm) for carbon atoms.

$1,25\text{-}(OH)_2D_3$ (calcitriol) was purchased from Endotherm, Germany. LG190178 was synthesized using a published procedure (Boehm et al. *Chem Biol* 1999, 6, 265-275).

Labeled Coregulator Peptides. Peptides, such as SRC2-3 (CLQEKHRILHKLLQNGNSPA) (Teichert et al. *Biochemistry* 2009, 48, 1454-1461) were purchased and labeled with cysteine-reactive fluorophores, such as Texas-Red maleimides and Alexa Fluor 647 maleimides, in DMF/PBS 50:50. After purification by HPLC, the corresponding labeled peptides were dissolved in DMSO and stored at −20° C.

Protein Expression and Purification. The VDR-LBDmt DNA was kindly provided by D. Moras (Rochel et al. *Mol Cell* 2000, 5, 173-179) and cloned into pMAL-c2X vector (New England Biolabs). For a detailed expression and purification protocol, see Teichert et al. *Biochemistry* 2009, 48, 1454-1461. For detailed expression and purification of protocols of PPARγ-LBD, TRα-LBD, TRβ-LBD, and AR-LBD, see Hwang et al. *J Biol Chem* 2011, 286, 11895-11908.

High Throughput FP Assay. The HTS was carried out at St. Jude Children's Research Hospital. The small molecule collection consisted of 275,000 unique compounds from commercial sources (ChemDiv, ChemBridge, and Life Chemicals). The FP assay was conducted in 384 well black polystyrene microplates (Corning, #3573). The assay solution contained buffer (25 mM PIPES (pH 6.75) 50 mM NaCl, 0.01% NP-40, 2% DMSO, VDR-LBD protein (1 µM), LG190178 (5 µM), and Alexa Fluor 647-labeled SRC2-3 (7.5 nM). Small molecule transfer into 20 µl assay solution was accomplished using a 50H hydrophobic coated pin tool (V&P Scientific), delivering 60 nl of a 10 mM compound solution, which resulted in a final concentration of 30 µM. Inhibition of binding was detected using FP performed on an EnVision multi-label plate reader (GE) with a 620 nm excitation filter, a 688 nm S polarized emission filter, a 688 nm R polarized emission filter, and a Cy5 FP dichroic mirror. Automation was realized using a system developed by high resolution engineering, which uses a Stäubli T60 robot arm to transfer plates from instrument to instrument. The assay solution was dispensed in bulk into empty plates using Matrix Wellmates (Matrix Technologies), followed by compound addition, centrifugation using a Vspin plate centrifuge (Velocity1 1), and incubation for 3 hours at room temperature. The positive control (3-dibutylamino-1-(4-hexyl-phenyl)-propan-1-one, Arnold et al. *J Biol Chem* 2005, 280, 43048-43055) and negative control (DMSO) were measured within each plate to determine the assay plate quality and to enable data normalization.

Fluorescence Resonance Energy Transfer (FRET) Transcription Assay. A GeneBLAzer® (Invitrogen) assay was used to identify VDR-coactivator inhibitors that regulate VDR-mediated transcription. The provided HEK293 cells of this assay expressed a fusion protein of VDR-LBD and the GAL4-DBD, which was activated by $1,25\text{-}(OH)_2D_3$, and induced transcription of a β-lactamase reporter gene. Quantification of β-lactamase was accomplished by detecting the decrease in FRET caused by the enzymatic cleavage of the β-lactam-containing substrate, which was added after an incubation time of 24 hours. The cleaved substrate concentration was quantified by measuring the fluorescence emission at 447 nm. Controls for this assay were 1,25-$(OH)_2D_3$ and LG190178 (positives) and DMSO (negative). Toxicity was determined by luminescence using Cell-Titer Glo (Promega), which was added to the plates after recording the FRET signal. Controls for cell viability were 3-dibutylamino-1-(4-hexyl-phenyl)-propan-1-one (100 μM in DMSO) (positive) and DMSO (negative). Two independent experiments were conducted in triplicate.

VDR Ligand Competition Assay. Ligand antagonism was determined by using a FP assay (PolarScreen, Invitrogen), which employs a fluorescently labeled 1,25-$(OH)_2D_3$ analog. Two independent experiments were conducted in quadruplicate and data was analyzed using nonlinear regression with variable slope (GraphPrism)

CYP24A1 Promoter Transcription Assay. This assay was used to determine the regulation of transcription of the VDR-target gene, CYP24A1, in the presence of small molecules. Briefly, HEK 293T cells (ATTC) were cultured in 75 $cm^2$ flasks using MEM/EBSS (Hyclone) with L-glutamine (2 mM), glucose (1 mM), non-essential amino acids, sodium pyruvate (1 mM), penicillin and streptomycin, and 10 percent heat inactivated FBS (Hyclone). At 50-70 percent confluency, cell media was changed to phenol red free MEM/EBSS with L-glutamine (2 mM), glucose (1 mM), non-essential amino acids, sodium pyruvate (1 mM), penicillin and streptomycin, and 10 percent dialyzed and heat inactivated FBS (Invitrogen), followed by the addition of 2 ml of untreated MEM/EBSS containing 1.56 μg of a VDR-pRc/CMV plasmid, 16 μg of a luciferase reporter gene plasmid containing a rat 24-hydroxylase gene promoter (−1399 to +76), 17.4 g of a *Renilla* luciferase control vector (Promega), Lipofectamine™ LTX (75 μl), and PLUS™ reagent (25 μl). After 16 hours, the cells were harvested and plated in sterile cell culture treated black 384 well plates with optical bottom (Nunc 142761) at a concentration of 15,000 cells per well. After 2 hours, plated cells were treated with small molecules in vehicle DMSO, followed by a 16 hours incubation time. Transcription was determined using a Dual-Luciferase® Reporter Assay (Promega). Cell viability was determined using the *Renilla* luciferase signal. $IC_{50}$ values and standard errors were calculated based on two independent experiments performed in quadruplicate. Controls for this assay were 1,25-$(OH)_2D_3$ and LG190178 (positives) and DMSO (negative). Controls for cell viability were 3-dibutylamino-1-(4-hexyl-phenyl)-propan-1-one (100 μM in DMSO) (positive) and DMSO (negative). Two independent experiments were conducted in quadruplets.

Solubility Assay. In a 384 UV plate (Corning #3675), 16 compounds were serial diluted in quadruplicate starting from a 10 mM compound stock solution in DMSO. Therefore, buffer (90 mM ethanolamine, 90 mM $KH_2PO_4$, 90 mM potassium acetate, and 30 mM KCl (pH 7.4)) containing 20 percent acetonitrile was used. The plate was sealed (Corning #6570), sonicated for 1 minute, and agitated for an additional 5 minutes before scanning from 230-800 nm at 5 minutes increments. A calibration plot was prepared for each compound for the maximal absorbance using background-subtracted values. A 384 well filter plate (Pall #5037) was pre-wetted with 20 percent acetonitrile/buffer, and filled with buffer (47.5 μl) and 10 mM of compound in DMSO (2.5 μl). The final DMSO concentration was 5 percent. After sonication (1 minute) and agitation (12 hours), the mixtures were filtered and 30 μl of each well was transferred into a 384 well UV plate, together with the addition of 20 μl of acetonitrile. The plate was agitated for 5 minutes and scanned from 230-800 nm at 5 minutes increments. The solubility was determined using background-subtracted values and the following equation: sol=absorbance at $\lambda_{max}$/slope*(5/3). Each plate had the following solubility standards: 4,5-diphenylimidazole (67.3±3.7 μM), β-estradiol (43.0±2.3 μM), diethylstilbestrol (108.3±5.4 μM), ketoconazole (134.5±2.4 μM), and 3-phenylazo-2,6-diaminopyridine (357.7±7.0 μM). All experiments were conducted in quadruplicate.

Permeability Assay. This assay was carried out using Millipore's Multiscreen™ protocol, AN1725EN00. Each plate had the following standards with the following permeability values (log $P_e$): Ranitidine (−8.02±0.074 cm/s) represents low permeability, carbamazepine (−6.81±0.0011 cm/s) represents medium permeability, and verapamil (−5.93±0.015 cm/s) represents high permeability. All experiments were conducted in triplicate.

NR-Coactivator Binding Studies in the Presence of 3-Indolyl-Methamines.

These assays were conducted in 384 well black polystyrene microplates (Corning) using a buffer (20 mM TRIS (pH 7.50), 100 mM NaCl, 0.01% NP-40, 2% DMSO) and analyzed with a M1000 reader (Tecan) to detect FP at an excitation/emission wavelength of 595/615 nm. For the androgen receptor, AR-LBD (5 μM): Texas Red-labeled SRC2-3 (7 nM) and dihydrotestosterone (5 μM) were incubated in buffer with small molecule for 3 hours; for the thyroid receptor α, TRα-LBD (2 μM): Texas Red-labeled SRC2-2 (7 nM) and triiodothyronine (1 μM) were incubated with small molecule for 3 hours; for the thyroid receptor β, TRβ-LBD (0.8 μM): Texas Red-labeled SRC2-2 (7 nM) and triiodothyronine (1 μM) were incubated with small molecule for 3 hours; for the peroxisome proliferator-activated receptor γ, PPARγ-LBD (5 μM): Texas Red-labeled DRIP2 (7 nM) and rosiglitazone (5 μM) were incubated with small molecule for 3 hours; for the VDR, VDR-LBD (1 μM): Texas Red-labeled SRC2-3 (7 nM) and LG190178 (5 μM) were incubated with small molecule for 3 hours. Two independent experiments were carried out in quadruplicate and data was analyzed using nonlinear regression with variable slope (GraphPrism).

VDR-Coactivator Binding Studies in the Presence of 3-Indolyl-Methamine 31b.

These assays were conducted in 384 well black polystyrene microplates (Corning) using a buffer (25 mM PIPES (pH 6.75) 50 mM NaCl, 0.01% NP-40, 2% DMSO) and analyzed with a M1000 reader (Tecan) to detect FP at an excitation/emission wavelength of 595/615 nm. VDR-LBD protein (1 μM), LG190178 (5 μM), and 7.5 nM of Texas-Red labeled SRC1-3 [CESKDHQLLRYLLDKDEKDL], Texas-Red labeled SRC2-3 [CLQEKHRILHKLLQNGNSPA], Texas-Red labeled SRC3-3 [CKKENNALLRYLLDRDDPSD], or Texas-Red labeled DRIP2 [CNTKNHPMLMNLLKDNPAQD] were incubated with different concentration of 31b. Two independent experiments were carried out in quadruplicate and data was analyzed using nonlinear regression with variable slope (GraphPrism).

Semi-quantitative real time PCR. DU145 cells were incubated at 37° C. with 31b (20 μM) in the presence or absence of 20 nM calcitriol for 18 h. Total RNA was isolated from cells using an RNAeasy kit (QIAGEN®). Genomic DNA was removed and cDNA was generated using equal amounts of RNA (QuantiTect® Reverse Transcription Kit, QIAGEN®). The cDNA reaction was then diluted 5-fold, and the QuantiFast® SYBR Green PCR Kit (QIAGEN®) was used for the real time PCR following manufacturer's recommendations. Primers used in these studies are as follows: GAPDH Forward Primer 5'-ACCACAGTCCATGCCATCAC-3' (SEQ ID NO: 1), Reverse Primer 5'-TCCACCAC- CCTGTTGCTGTA-3' (SEQ ID NO: 2); TRPV6 Forward Primer 5'- ACTGTCATTGGGGCTATCATC-3' (SEQ ID NO: 3), Reverse Primer 5'-CAGCAGAATCGCATCAG-GTC-3' (SEQ ID NO: 4); Real-time rt-PCR was carried out on a Mastercycler (Eppendorf). The ΔΔCt method was used to measure the fold change in gene expression of target genes. Standard deviations were calculated from 3 biological independent experiments performed in triplicate.

Example 1

Initial Compound Screening

Two hundred and seventy-five thousand compounds were tested in the primary high throughput screening campaign at a single dosage of 30 µM. Based on the FP signal, 589 compounds exhibited more than 40 percent inhibition of the VDR-SRC2-3 interaction at that concentration and were less likely to bear structure elements of promiscuous aggregating molecules[14] or electrophilic compounds.[15] HTS evaluation of the frozen stock solutions of these compounds confirmed that 140 compounds exhibited a dose-dependent response with $IC_{50}$ values of less than 40 µM.

The stock solutions for the 140 compounds exhibiting a dose-dependent response with IC50 values of less than 40 µM were performed in HEK293 cells, which express a fusion protein of VDR-LBD and GAL4-DBD, using the FRET transcription assay. The quantity of uncleaved substrate, which was determined by measuring the fluorescence emission at 447 nm, revealed that 48 of the 140 active compounds were able to regulate the VDR-mediated transcription of β-lactamase.

The abilities of the 48 compounds that were able to regulate the VDR-mediated transcription of β-lactamase were further evaluated in the VDR Ligand Competition assay, to exclude allosteric VDR-coactivator binding disruption through VDR ligand antagonism. The application of a VDR PolarScreen (Invitrogen) confirmed that none of the active compounds was able to replace labeled 1,25-$(OH)_2D_3$.

The 48 compounds were then purchased as solids, dissolved in DMSO as a 10 mM solution, and analyzed by liquid chromatography-mass spectroscopy (LC-MS) to determine purity and identity (Table 1). A subsequent dose-response analysis using the described FP assay determined that 29 of the 48 purchased compounds exhibited $IC_{50}$ values of less than 40 µM. These compounds fell into 6 groups, based on their scaffold similarity. Of these six groups, nine compounds (11-19) were 3-indoyl-methanamines as illustrated below.

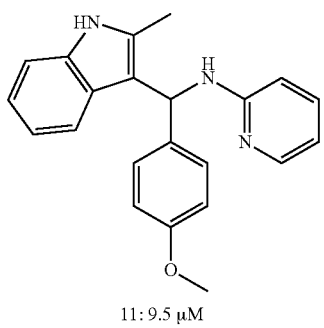

11: 9.5 µM

-continued

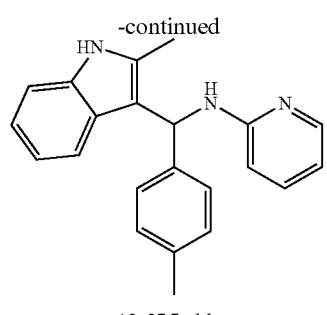

12: 27.7 µM

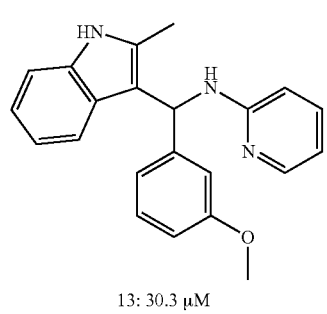

13: 30.3 µM

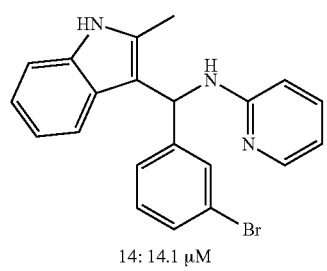

14: 14.1 µM

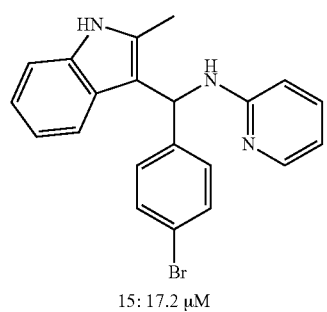

15: 17.2 µM

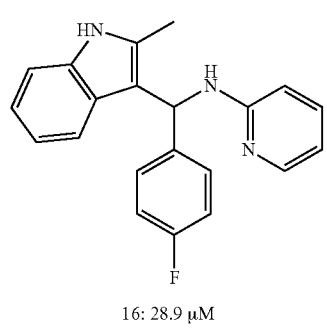

16: 28.9 µM

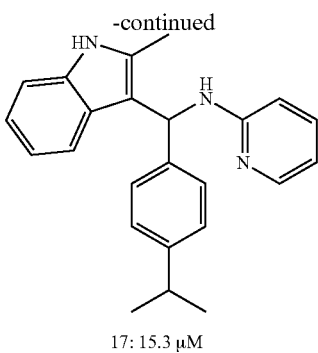

17: 15.3 μM

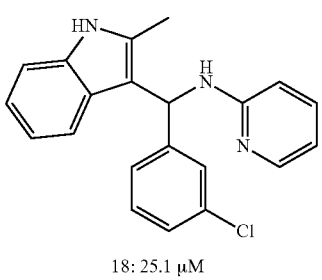

18: 25.1 μM

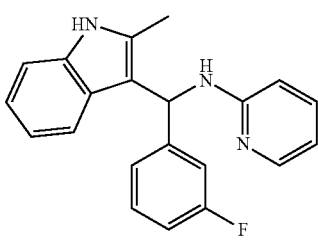

19: 22.1 μM

Further characterizations were carried out, which include the determination of small molecule aqueous solubility, permeability using PAMPA (Parallel Artificial Membrane Permeability), toxicity in HEK293T cells, and their ability to inhibit VDR-mediated transcription using the described FRET GeneBLAzer assay. The results are summarized in Table 1.

The 3-indolyl-methanamines showed promising characteristics, which included good to excellent solubility, high permeability, inhibition of VDR-SRC2-3 interaction at low micromolar concentrations, and the ability to inhibit VDR-mediated transcription in the range of 62.5-20.8 μM.

Example 2

Synthesis and Characterization of Compounds

General Procedure for the Aza-Friedel-Crafts Reaction. In a dry flask, the appropriate aniline (2 mmol) and aldehyde (2 mmol) were dissolved in toluene (2 ml) and stirred for 1 h. Then the appropriate indole (2 mmol) and decanoic acid (0.2 mmol, 10 mol %) were added slowly as a solution in toluene (2 ml). The reaction mixture was stirred at room temperature and monitored by TLC. After the reaction was completed, saturated $NaHCO_3$ (6 ml) was added. The mixture was extracted with dichloromethane (3×10 ml). The organic layer was combined, washed with brine (10 mL), and dried over anhydrous $Na_2SO_4$. The solvents were removed under reduced pressure and the residue was purified by recrystallization or chromatography through Biotage SP1 flash system. Compounds and the numbering scheme used herein are illustrated in Scheme 2.

Scheme 2.

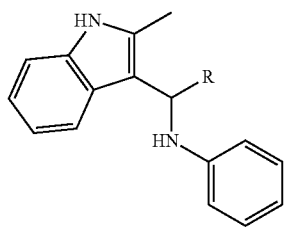

30a: R = $(C_6H_5)$
30b: R = $4\text{-Cl}(C_6H_4)$
30c: R = $4\text{-MeO}(C_6H_4)$
30d: R = $4\text{-Me}(C_6H_4)$
30e: R = $4\text{-Me}_2N(C_6H_4)$
30f: R = $4\text{-NO}_2(C_6H_4)$
30g: R = $CH_3$
30h: R = 2-naphthalenyl
30i: R = $4\text{-(3-propan-1-ol)}(C_6H_4)$

TABLE 1

Biophysical and biochemical properties of validated VDR-SRC2-3 inhibitors.

| Cpd | % Purity[a] | Solubility (μM) | Log($P_e$) (cm/s) | VDR-SRC2-3 Inhibition $IC_{50}$ (μM) | Inhibition of Transcription (%) | | Toxicity (%) | |
|---|---|---|---|---|---|---|---|---|
| | | | | | Conc. 62.5 μM | Conc. 20.8 μM | Conc. 62.5 μM | Conc. 20.8 μM |
| 11 | 42.8 | 342.0 | −6.25 | 9.6 | 100 | 90 | 100 | 30 |
| 12 | 58.0 | 422.6 | −6.10 | 27.7 | 100 | 10 | 90 | 0 |
| 13 | 65.6 | 403.3 | −6.12 | 30.3 | 100 | 0 | 60 | 0 |
| 14 | 64.9 | 132.5 | −6.11 | 14.1 | 100 | 10 | 100 | 10 |
| 15 | 84.1 | 84.6 | −6.01 | 17.3 | 100 | 90 | 100 | 40 |
| 16 | 78.5 | 468.7 | −6.05 | 28.9 | 100 | 10 | 100 | 0 |
| 17 | 42.4 | 201.4 | −6.12 | 15.4 | 9.1[b] | | 18.0[b] | |
| 18 | 81.6 | 277.7 | −6.01 | 25.1 | 100 | 0 | 100 | 0 |
| 19 | 79.1 | 427.8 | −5.99 | 22.2 | 80 | 0 | 60 | 0 |

[a]Purities were determined by high pressure liquid chromatography using a photodiode array and identity was confirmed by mass spectrometry;
[b]$IC_{50}/LD_{50}$ values (μM) are given instead of percentages for highly active compounds using the following non-linear regression equation: Y = Bottom + (Top − Bottom)/(1 + 10^((LogIC50 − X) * HillSlope)) using three independent experiments in quadruplicate.

-continued

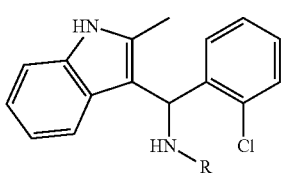

31

31a: R = (C₆H₅)
31b: R = 4-Cl(C₆H₄)
31c: R = 4-MeO(C₆H₄)
31d: R = 4-Me(C₆H₄)
31e: R = 4-Me₂N(C₆H₄)
31f: R = 4-NO₂(C₆H₄)
31g: R = 4-CF₃
31h: R = 2-MeO(C₆H₄)

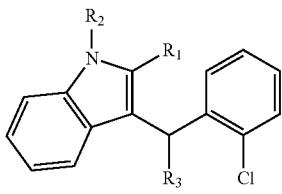

32

32a: $R_1$ = H, $R_2$ = Me
$R_3$ = NH(C₆H₅)
32b: $R_1$ = H, $R_2$ = H
$R_3$ = NH(C₆H₅)
32c: $R_1$ = Me, $R_2$ = H
$R_3$ = S(C₆H₅)

N-((2-methyl-1H-indol-3-yl)(phenyl)methyl)aniline (30a). $R_f$=0.3 (EtOAc/hexanes=1/4). 230 mg white solid, 37% yield. $^1$H NMR (300 MHz, CDCl₃, TMS): δ 2.34 (s, 3H), 4.34 (s, 1H), 5.76 (s, 1H), 6.59 (dd, J=1.8, 4.8 Hz, 2H), 6.69-6.73 (m, 1H), 6.69-7.05 (m, 1H), 7.08-7.18 (m, 4H), 7.26-7.29 (m, 3H), 7.38 (d, J=7.5 Hz, 2H), 7.49 (d, J=7.8 Hz, 1H), 7.82 (s, 1H). $^{13}$C NMR (300 MHz, CDCl₃, TMS): 12.35, 54.40, 110.8, 112.45, 113.28, 116.12, 118.76, 119.10, 120.43, 126.79, 128.58, 143.9, 144.1, 148.88, 148.96; Anal. Calcd. for C₂₂H₂₀N₂: C, 84.58, H, 6.45, N, 8.97, found C, 84.2027, H, 6.72, N, 8.66.

N-((4-chlorophenyl)(2-methyl-1H-indol-3-yl)methyl)aniline (30b). $R_f$=0.3 (EtOAc/hexanes=1/4). 260 mg white solid, 36% yield. $^1$H NMR (300 MHz, CDCl₃, TMS): δ 2.41 (s, 3H), 4.35 (s, 1H), 5.73 (d, J=2.4 Hz, 1H), 6.57 (dd, J=1.5, 7.8 Hz, 2H), 6.74-6.78 (m, 2H), 6.99-7.05 (m, 1H), 7.11-7.19 (m, 3H), 7.26-7.31 (m, 3H), 7.43 (dd, J=6.9, 7.5 Hz, 2H), 7.87 (s, 1H). $^{13}$C NMR (300 MHz, CDCl₃, TMS): 12.13, 53.75, 111.01, 112.12, 113.23, 114.33, 116.22, 118.99, 120.87, 126.71, 129.43, 132.72, 142.90, 148.72; Anal. Calcd. for C₂₂H₁₉ClN₂: C, 76.18, H, 5.52, N, 8.08 found C, 76.0612, H, 5.82, N, 7.87.

N-((4-methoxyphenyl)(2-methyl-1H-indol-3-yl)methyl)aniline (30c). $R_f$=0.3 (EtOAc/hexanes=1/4). 266 mg white solid, 38% yield. $^1$H NMR (300 MHz, CDCl₃, TMS): δ 2.34 (s, 3H), 3.76 (s, 3H), 4.32 (s, 1H), 5.72 (s, 1H), 6.56 (d, J=9.0 Hz, 2H), 6.68 (dd, J=6.3, 7.2 Hz, 1H), 6.67-6.87 (m, 1H), 6.96-7.02 (m, 3H), 7.05-7.15 (m, 2H), 7.22-7.25 (m, 1H), 7.37 (d, J=8.7 Hz, 2H), 7.43 (d, J=7.8 Hz, 1H), 7.76 (s, 1H); $^{13}$C NMR (300 MHz, CDCl₃, TMS): 12.17, 54.02, 55.11, 110.67, 112.53, 113.10, 113.62, 116.29, 119.14, 120.38, 127.28, 128.45, 129.15, 135.64, 148.74, 158.45; Anal. Calcd. for C₂₂H₁₉ClN₂: C, 80.67, H, 6.48, N, 8.18, found C, 78.99, H, 6.59, N, 7.71.

N-((2-methyl-1H-indol-3-yl)(p-tolyl)methyl)aniline (30d). $R_f$=0.3 (EtOAc/hexanes=1/4). 460 mg light yellow oil, 69% yield. $^1$H NMR (300 MHz, CDCl₃, TMS): δ 2.30 (s, 3H), 2.39 (s, 3H), 4.32 (s, 1H), 5.73 (s, 1H), 6.57 (dd, J=0.6, 8.7 Hz, 2H), 6.69 (dd, J=0.9, 7.2 Hz, 1H), 6.69-7.02 (m, 2H), 7.06-7.16 (m, 3H), 7.24-7.27 (m, 2H), 7.36 (d, J=7.8 Hz, 2H), 7.46 (d, J=8.1 Hz, 1H), 7.79 (s, 1H). $^{13}$C NMR (300 MHz, CDCl₃, TMS): 12.46, 21.28, 55.36, 110.70, 112.38, 113.23, 115.95, 118.67, 120.35, 127.22, 129.17, 135.51, 141.28, 148.73.

N,N-dimethyl-4-((2-methyl-1H-indol-3-yl)(phenylamino)methyl)aniline (30e). $R_f$=0.2 (EtOAc/hexanes=1/4). 368 mg light yellow oil, 52% yield. $^1$H NMR (300 MHz, CDCl₃, TMS): δ 2.10 (s, 3H), 2.93 (s, 6H), 5.94 (s, 1H), 6.68 (d, J=9.0 Hz, 2H), 6.87 (ddd, J=1.2, 7.5, 7.5 Hz, 2H), 7.04 (dd, J=7.2, 7.5 Hz, 4H), 7.14 (d, J=8.4 Hz, 2H), 7.24 (dd, J=0.6, 0.9 Hz, 1H), 7.26 (d, J=1.2 Hz, 1H), 7.28-7.32 (m, 1H), 7.71 (s, 1H). $^{13}$C NMR (300 MHz, CDCl₃, TMS): 12.14, 52.89, 55.94, 110.18, 111.01, 113.74, 115.11, 118.68, 120.35, 126.98, 128.58, 135.84, 140.44, 142.14, 151.45; Anal. Calcd. for C₂₄H₂₅N₃: C, 81.09, H, 7.09, N, 11.82, found C, 82.11, H, 7.02, N, 10.45.

N-((2-methyl-1H-indol-3-yl)(4-nitrophenyl)methyl)aniline (30f). $R_f$=0.2 (EtOAc/hexanes=1/4). 700 mg light yellow oil, 90% yield. $^1$H NMR (300 MHz, CDCl₃, TMS): δ 2.43 (s, 3H), 4.40 (s, 1H), 5.78 (d, J=2.4 Hz, 1H), 6.52 (dd, J=0.9, 8.1 Hz, 2H), 6.76 (dd, J=7.2, 7.5 Hz, 1H), 7.01 (dd, J=1.2, 8.1 Hz, 1H), 7.10-7.19 (m, 3H), 7.28 (ddd, J=0.6, 0.6, 7.8 Hz, 1H), 7.35 (d, J=8.1 Hz, 1H), 7.66 (d, J=8.4 Hz, 2H), 7.95 (s, 1H), 8.15 (d, J=9.0 Hz, 2H). $^{13}$C NMR (300 MHz, CDCl₃, TMS): 12.40, 55.36, 111.08, 111.75, 113.38, 114.22, 116.12, 116.4, 118.65, 120.72, 123.90, 126.88, 128.80, 133.75, 135.68, 146.74, 148.10, 151.75.

N-(1-(2-methyl-1H-indol-3-yl)ethyl)aniline (30g). $R_f$=0.3 (EtOAc/hexanes=1/4). 448 mg yellow solid, 90% yield. $^1$H NMR (300 MHz, CDCl₃, TMS): δ 1.93 (d, J=7.8 Hz, 3H), 2.30 (s, 3H), 4.69 (q, J=4.8 Hz, 1H), 6.96 (ddd, J=0.9, 1.2, 8.1 Hz, 2H), 7.05 (ddd, J=0.9, 1.2, 7.8 Hz, 2H), 7.22 (s, 1H), 7.24 (s, 1H), 7.56 (d, J=8.1 Hz, 2H), 7.64 (s, 1H). $^{13}$C NMR (300 MHz, CDCl₃, TMS): 12.84, 21.81, 28.75, 110.85, 114.79, 118.47, 119.84, 128.29, 130.63, 135.25; Anal. Calcd. for C₁₇H₁₈N₂: C 81.56, H, 7.25, N, 11.19, found C, 81.6702, H, 7.2919, N, 9.1870.

N-((2-methyl-1H-indol-3-yl)(naphthalen-2-yl)methyl)aniline (30h). $R_f$=0.3 (EtOAc/hexanes=1/4). 546 mg orange oil, 75% yield. $^1$H NMR (300 MHz, CDCl₃, TMS): δ 2.38 (d, J=3.3 Hz, 3H), 3.89 (t, J=6.0 Hz, 2H), 5.90 (s, 1H), 6.59-6.62 (m, 2H), 6.94-6.99 (m, 1H), 7.05-7.15 (m, 3H), 7.18-7.27 (m, 1H), 7.41-7.53 (m, 4H), 7.74-7.83 (m, 3H), 8.01 (s, 1H). $^{13}$C NMR (300 MHz, CDCl₃, TMS): 12.24, 54.41, 110.87, 112.19, 113.19, 114.12, 116.45, 118.84, 119.79, 124.99, 126.31, 135.59, 141.56, 148.76.

3-(4-((2-methyl-1H-indol-3-yl)(phenylamino)methyl)phenoxy)propan-1-ol (30i). $R_f$=0.3 (EtOAc/hexanes=1/4). 431 mg red oil, 56% yield. $^1$H NMR (300 MHz, CDCl₃, TMS): δ 2.05-2.10 (m, 5H), 3.89 (t, J=6.0 Hz, 2H), 4.20 (t, J=6.3 Hz, 2H), 5.94 (s, 1H), 6.83 (dd, J=9.0, 13.5 Hz, 2H), 6.99 (d, J=8.4 Hz, 2H), 7.15-7.26 (m, 3H), 7.36-7.41 (m, 2H), 7.74 (s, 1H), 7.84 (d, J=8.7 Hz, 2H), 8.38 (s, 1H).

N-((2-chlorophenyl)(2-methyl-1H-indol-3-yl)methyl)aniline (31a). $R_f$=0.3 (EtOAc/hexanes=1/4). 520 mg white solid, 75% yield. $^1$H NMR (300 MHz, CDCl₃, TMS): δ 2.33 (s, 3H), 4.30 (s, 1H), 5.93 (s, 1H), 6.48 (d, J=7.8 Hz, 2H), 6.69 (dd, J=7.2, 7.5 Hz, 1H), 6.97 (ddd, J=1.2, 6.6, 8.4 Hz, 1H), 7.05-7.34 (m, 7H), 7.41 (d, J=8.1 Hz, 1H), 7.75 (s, 1H), 7.92 (dd, J=1.5, 7.8 Hz, 1H). $^{13}$C NMR (300 MHz, CDCl₃, TMS): 12.55, 51.76, 109.53, 110.54, 112.79, 116.13, 118.77, 120.99, 127.31, 129.64, 139.19, 147.42. Anal. Calcd. for C$_{22}$H$_{19}$ClN$_2$: C, 76.18, H, 5.52, N, 8.08, found C, 75.6379, H, 5.4467, N, 7.96.

4-chloro-N-((2-chlorophenyl)(2-methyl-1H-indol-3-yl)methyl)aniline (31b). R$_f$=0.3 (EtOAc/hexanes=1/4). 560 mg light pink solid, 74% yield. $^1$H NMR (300 MHz, CDCl$_3$, TMS): δ 2.39 (s, 3H), 4.34 (d, J=3.0 Hz, 1H), 5.92 (d, J=3.3 Hz, 1H), 6.42 (dd, J=2.1, 8.7 Hz, 1H), 6.97-7.14 (m, 4H), 7.22-7.43 (m, 6H), 7.87 (dd, J=2.1, 7.8 Hz, 2H). $^{13}$C NMR (300 MHz, CDCl$_3$, TMS): 12.55, 51.76, 109.22, 110.85, 111.16, 114.11, 119.08, 127.30, 132.90, 135.23, 146.80. Anal. Calcd. for C$_{22}$H$_{18}$Cl$_2$N$_2$: C, 69.30, H, 4.76, N, 7.35, found C, 69.602, H, 4.85, N, 7.24.

N-((2-chlorophenyl)(2-methyl-1H-indol-3-yl)methyl)-4-methoxyaniline (31c). R$_f$=0.3 (EtOAc/hexanes=1/4). 266 mg white solid, 38% yield. $^1$H NMR (300 MHz, CDCl$_3$, TMS): δ 2.32 (s, 3H), 3.70 (s, 3H), 4.08 (s, 1H), 5.86 (s, 1H), 6.43 (dd, J=2.1, 6.6 Hz, 2H), 6.72 (dd, J=2.4, 7.2 Hz, 2H), 6.82-6.99 (m, 1H), 7.03-7.08 (m, 1H), 7.16-7.33 (m, 4H), 7.44 (d, J=7.8 Hz, 1H), 7.78 (s, 1H), 7.93 (dd, J=1.8, 7.2 Hz, 1H). $^{13}$C NMR (300 MHz, CDCl$_3$, TMS): 11.63, 55.93, 109.8, 111.13, 115.25, 118.7, 120.1, 127.2, 133.6, 140.6, 142.5, 151.2. Anal. Calcd. for C$_{23}$H$_{21}$ClN$_2$O: C, 73.30, H, 5.62, N, 7.43, found C, 73.24, H, 5.75, N, 7.2355.

N-((2-chlorophenyl)(2-methyl-1H-indol-3-yl)methyl)-4-methylaniline (31d). R$_f$=0.3 (EtOAc/hexanes=1/4). 420 mg light pink solid, 58% yield. $^1$H NMR (300 MHz, CDCl$_3$, TMS): δ 2.39 (s, 3H), 2.44 (s, 3H), 4.24 (s, 1H), 5.93 (s, 1H), 6.43 (dd, J=2.1, 6.6 Hz, 2H), 6.95-7.02 (m, 3H), 7.11 (dd, J=1.2, 7.8 Hz, 1H), 7.20-7.23 (m, 1H), 7.27-7.34 (m, 2H), 7.35 (dd, J=1.5, 7.8 Hz, 1H), 7.45 (d, J=7.5 Hz, 1H), 7.85 (s, 1H), 7.96 (dd, J=1.8, 7.8 Hz, 1H). $^{13}$C NMR (300 MHz, CDCl$_3$, TMS): 12.15, 20.17, 52.37, 110.18, 111.28, 112.90, 118.98, 124.76, 127.99, 129.66, 140.18, 146.21. Anal. Calcd. for C$_{23}$H$_{21}$ClN$_2$: C, 76.55, H, 5.87, N, 7.76, found C, 76.55, H, 5.98, N, 7.5355.

N$^1$-((2-chlorophenyl)(2-methyl-1H-indol-3-yl)methyl)-N$^4$,N$^4$-dimethylbenzene-1,4-diamine (31e). R$_f$=0.2 (EtOAc/hexanes=1/2). 160 mg yellow solid, 21% yield. $^1$H NMR (300 MHz, CDCl$_3$, TMS): δ 2.25 (s, 3H), 2.80 (s, 6H), 5.27 (s, 1H), 5.95 (s, 1H), 6.51-6.55 (m, 2H), 6.77 (d, J=5.7 Hz, 2H), 6.97-7.17 (m, 4H), 7.22-7.28 (m, 1H), 7.31-7.34 (m, 1H), 7.51 (d, J=7.8 Hz, 1H), 8.02 (d, J=7.8 Hz, 1H), 8.31 (s, 1H). $^{13}$C NMR (300 MHz, CDCl$_3$, TMS): 11.61, 37.22, 111.02, 118.15, 119.77, 126.96, 128.31, 129.69, 131.11, 135.20, 142.13. Anal. Calcd. for C$_{24}$H$_{24}$ClN$_3$: C, 73.93, H, 6.20, N, 10.78, found C, 77.40, H, 5.54, N, 7.11.

N-((2-chlorophenyl)(2-methyl-1H-indol-3-yl)methyl)-4-nitroaniline (31f). R$_f$=0.2 (EtOAc/hexanes=1/4). 433 mg yellow solid, 55% yield. $^1$H NMR (300 MHz, CDCl$_3$, TMS): δ 2.38 (s, 3H), 5.06 (s, 1H), 6.08 (d, J=4.5 Hz, 1H), 6.45 (dd, J=2.1, 7.2 Hz, 2H), 6.97-7.02 (m, 1H), 7.09-7.15 (m, 1H), 7.24-7.41 (m, 5H), 7.71 (dd, J=2.1, 6.9 Hz, 1H), 7.96 (s, 1H), 8.04 (dd, J=2.1, 7.2 Hz, 2H). $^{13}$C NMR (300 MHz, CDCl$_3$, TMS): 12.24, 51.76, 108.21, 111.15, 117.77, 118.77, 120.70, 128.94, 130.27, 133.29, 134.22, 134.92, 135.93, 138.87, 153.10. Anal. Calcd. for C$_{22}$H$_{18}$ClN$_3$O$_2$: C, 67.43, H, 4.63, N, 10.72, found 67.4615, H, 4.7347, N, 10.4091.

N-((2-chlorophenyl)(2-methyl-1H-indol-3-yl)(phenyl)methyl)-4-(trifluoromethyl)aniline (31g). R$_f$=0.3 (EtOAc/hexanes=1/4). 320 mg red solid, 55% yield. $^1$H NMR (300 MHz, CDCl$_3$, TMS): δ 2.17 (s, 3H), 4.84 (s, 1H), 5.94 (s, 1H), 6.69 (d, J=7.8 Hz, 2H), 6.99 (d, J=7.8 Hz, 2H), 7.04-7.09 (m, 2H), 7.13-7.33 (m, 3H), 7.30-7.40 (m, 4H), 7.41 (d, J=8.4 Hz, 1H), 7.42-7.58 (m, 1H), 7.84 (s, 1H), 7.88 (dd, J=2.1, 7.8 Hz, 1H). $^{13}$C NMR (300 MHz, CDCl$_3$, TMS): 11.0, 61.07, 110.4, 112.6, 116.9, 119.4, 122.1, 126.1, 127.2, 128.2, 132.9, 136.8, 141.4.

N-((2-chlorophenyl)(2-methyl-1H-indol-3-yl)methyl)-2-methoxyaniline(31h). R$_f$=0.3 (EtOAc/hexanes=1/4). 486 mg white solid, 65% yield. $^1$H NMR (300 MHz, CDCl$_3$, TMS): δ 2.33 (s, 3H), 3.78 (s, 3H), 4.89 (s, 1H), 5.94 (s, 1H), 6.29 (dd, J=1.5, 7.8 Hz, 1H), 6.62-6.79 (m, 4H), 6.93-6.98 (m, 1H), 7.04-7.09 (m, 1H), 7.13-7.33 (m, 3H), 7.41 (d, J=8.4 Hz, 1H), 7.84 (s, 1H), 7.88 (dd, J=2.1, 7.8 Hz, 1H). $^{13}$C NMR (300 MHz, CDCl$_3$, TMS): 12.24, 52.71, 55.41, 109.54, 110.16, 111.17, 117.15, 121.44, 121.44, 127.0, 127.32, 129.0, 130.30, 132.61, 136.58, 146.56. Anal. Calcd. for C$_{23}$H$_{21}$ClN$_2$O: C, 73.30, H, 5.62, N, 7.43. found C, 73.0355, H, 5.707, N, 7.45.

N-((2-chlorophenyl)(1-methyl-1H-indol-3-yl)methyl)aniline (32a). R$_f$=0.3 (EtOAc/hexanes=1/4). 266 mg white solid, 38% yield. $^1$H NMR (300 MHz, CDCl$_3$, TMS): δ 3.70 (s, 3H), 4.38 (d, J=2.4 Hz, 1H), 6.19 (d, J=3.0 Hz, 1H), 6.51-6.55 (m, 3H), 6.69 (dd, J=7.2, 7.5 Hz, 1H), 7.09-7.16 (m, 3H), 7.20-7.33 (m, 4H), 7.39-7.42 (m, 1H), 7.66 (s, 1H), 7.68-7.72 (m, 1H). $^{13}$C NMR (300 MHz, CDCl$_3$, TMS): 32.98, 50.83, 110.17, 113.18, 114.81, 115.86, 119.06, 121.69, 126.95, 128.91, 137.59, 140.22, 147.42. Anal. Calcd. for C$_{22}$H$_{19}$ClN-2: C, 76.18, H, 5.52, N, 8.08, found C, 76.1473, H, 5.6148, N, 7.7124.

N-((2-chlorophenyl)(1H-indol-3-yl)methyl)aniline (32b). R$_f$=0.3 (EtOAc/hexanes=1/4). 146 mg light yellow oil, 22% yield. $^1$H NMR (300 MHz, CDCl$_3$, TMS): δ 6.21 (s, 1H), 6.55 (d, J=7.8 Hz, 2H), 6.68-6.73 (m, 2H), 7.10-7.16 (m, 4H), 7.21-7.28 (m, 4H), 7.37-7.42 (m, 2H), 7.66-7.71 (m, 2H). $^{13}$C NMR (300 MHz, CDCl$_3$, TMS): 51.14, 112.18, 114.12, 115.14, 119.9, 121.12, 123.68, 126.69, 127.6, 129.0, 132.56, 136.57, 140.53, 148.44.

Synthesis of Compound 32c.

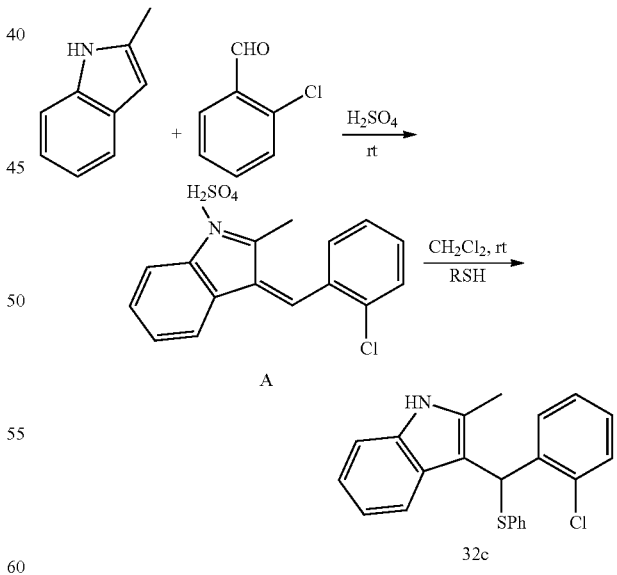

Concentrated sulfuric acid was added slowly on a stirring rod to 0.5 g of 2-methylindole dissolved in a 3 ml 2-chlorobenzaldehyde, until the entire mass was almost solid. The reaction product was washed thoroughly with toluene and ether. It formed orange-colored solid complex A, 1.3 g, yield 97%.

To a solution of complex A (48 mg, 0.14 mmol) in acetone (1 mL) was added benzenethiol (0.28 mmol) dropwise at room temperature. After stirring for 30 minutes, the orange precipitate disappeared, and a homogenous solution was formed. The reaction mixture was washed with NaHCO$_3$ and brine, dried over Na$_2$SO$_4$, concentrated and purified by SP1 system to obtain pure product.

3-((2-chlorophenyl)(phenylthio)methyl)-2-methyl-1H-indole (32c). $R_f$=0.3 (EtOAc/hexanes=1/4). 41 mg white solid, 75% yield. $^1$H NMR (300 MHz, CDCl$_3$, TMS): 35 2.29 (s, 3H), 6.15 (s, 1H), 7.02-7.33 (m, 11H), 7.79 (d, J=7.8 Hz, 2H), 8.11 (dd, J=2.1, 8.1 Hz, 1H). $^{13}$C NMR (300 MHz, CDCl$_3$, TMS): 12.46, 46.18, 107.43, 111.13, 118.97, 120.59, 126.85, 127.07, 127.28, 129.14, 130.28, 130.77, 133.32, 133.98, 135.60, 135.8, 137.95. Anal. Calcd. for C$_{22}$H$_{18}$ClNS: C, 72.61, H, 4.99, N, 3.85, found C, 73.1803, H, 5.48, N, 3.724.

Example 3

Biophysical and Biochemical Characterization

Compounds prepared as described in Example 3 were characterized using biophysical and biochemical assays described above, where transcription inhibition was determined using the CYP24A1 promoter transcription assay. Results are summarized in Table 2.

carbon-nitrogen bonds and forming the corresponding azafulvenium salts (Xie et al. *Synlett* 1999, 498-500.).

To discriminate which of the binding partners (VDR or SRC2-3) is alkylated by 3-indolyl-methanamines, Alexa Fluor-labeled SRC2-3 peptide (7 nM) was incubated for 3 hours with different concentration of 31b followed by the addition of VDR-LBD (1 μM) and LG190178 (5 μM). Fluorescence polarization was detected after 5 minutes, and the binding isotherm is illustrated in black circles in FIG. 1. VDR-LBD (1 μM) and LG190178 (5 μM) was incubated for 3 hours with different concentration of 31b followed by the addition of Alexa Fluor-labeled SRC2-3 peptide (7 nM). Fluorescence polarization was detected after 5 minutes, and the binding isotherm is illustrated in black squares in FIG. 1. The binding isotherm of each condition was different. Pre-incubation of 31b with SRC2-3 followed by the addition of VDR did not result in an alkylation reaction because the FP signal did not change with higher concentration of 31b. In contrast, pre-incubation of VDR with different 31b concentrations followed by the addition of SRC2-3 did result in a change of FP signal. The corresponding isotherm was similar to the inhibition observed for combining all reagents at the same time and measuring FP after 3 hours.

TABLE 2

Biophysical and biochemical properties of compounds.

| Cpd | Solubility (μM)[a] | Permeability Log($P_e$) (cm/s) | VDR-SRC2-3 Inhibition IC$_{50}$ (μM) | Rate constant k for the dissociation of SRC2-3 from VDR ($10^{-5}$)[b] | Transcription Inhibition IC$_{50}$ (μM) | Toxicity LC$_{50}$ (μM) |
|---|---|---|---|---|---|---|
| 30a | 252.9 | −6.00 | 30.2 ± 4.8 | 45.1 ± 1.6 | 10.9 ± 2.8 | 15.3 ± 2.9 |
| 30b | 93.9 | −6.03 | 31.7 ± 4.3 | 34.2 ± 1.0 | 8.1 ± 1.7 | 14.6 ± 3.4 |
| 30c | 237.5 | −6.10 | 31.2 ± 3.2 | 88.0 ± 4.7 | 12.1 ± 1.8 | 17.2 ± 2.5 |
| 30d | 175.1 | −6.34 | 43.6 ± 7.8 | 35.7 ± 1.4 | 14.6 ± 2.5 | 21.7 ± 4.2 |
| 30e | 157.7 | −6.88 | n.s. | 2.0 ± 0.16 | 13.5 ± 1.3 | 25.8 ± 6.3 |
| 30f | 117.6 | −6.08 | 28.5 ± 4.5 | 6.7 ± 0.12 | 12.2 ± 2.4 | 16.2 ± 2.5 |
| 30g | 189.0 | −6.40 | 104.8 ± 15.2 | 1.8 ± 0.15 | 20.1 ± 5.2 | 37.4 ± 7.7 |
| 30h | 67.3 | −6.30 | 29.6 ± 3.1 | 14.2 ± 0.28 | 15.0 ± 2.4 | 20.8 ± 3.5 |
| 30i | 503.4 | −6.83 | 58.6 ± 8.1 | 2.3 ± 0.21 | 13.1 ± 2.5 | 31.4 ± 8.2 |
| 31a | 31.6 | −6.41 | 29.8 ± 4.5 | 38.6 ± 0.89 | 8.5 ± 1.8 | 12.6 ± 2.2 |
| 31b | 68.0 | −6.24 | 36.7 ± 5.1 | 4.5 ± 0.59 | 4.2 ± 1.9 | 11.6 ± 1.7 |
| 31c | 84.2 | −6.30 | 26.5 ± 3.4 | 39.1 ± 1.3 | 5.8 ± 2.1 | 12.1 ± 2.2 |
| 31d | 35.9 | −6.45 | 17.7 ± 3.2 | 23.7 ± 0.35 | 8.2 ± 1.5 | 12.7 ± 3.0 |
| 31e | 21.0 | −7.28 | n.s. | 0.87 ± 0.13 | 8.7 ± 1.5 | 19.4 ± 3.8 |
| 31f | 4.9 | −7.60 | n.s. | 1.2 ± 0.16 | 4.4 ± 1.1 | 11.0 ± 2.1 |
| 31g | n.d. | n.d. | n.s. | 2.5 ± 0.07 | 24.0 ± 5.7 | 43.1 ± 9.1 |
| 31 h | 59.7 | −6.22 | 24.3 ± 4.4 | 25.2 ± 0.36 | 8.6 ± 1.1 | 12.1 ± 2.7 |
| 32a | 15.3 | −6.58 | n.o. | n.o. | >70 | >70 |
| 32b | 52.3 | −6.51 | 20.3 ± 4.5 (partial) | 1.4 ± 0.12 | 21.6 ± 3.3 | >70 |
| 32c | 11.8 | −6.89 | n.o. | n.o. | >70 | >70 |

[a]Solubilities were determined in phosphate-buffered saline at pH 7.4;
[b]The fluorescence polarization assay was monitored over time. Dissociation rate constants were obtained by linear fitting of ln(mP) (fluorescence polarization) against time (first order kinetics).
n.d. = not determined; n.s. = no saturation of signal at higher small molecule concentration (no reliable non-linear fitting possible); n.o. = not observed.

Example 4

Identification of Reaction Partner

The different reaction rates of the 3-indolyl-methanamines and similar IC$_{50}$ values indicate that these compounds are likely to react with VDR or SRC2-3 in an irreversible fashion. It was reported that, especially under acidic conditions or elevated temperature, 3-indolyl-methanamines underwent elimination reactions by breaking the Example 5

Linear Free Energy Relationships

Figure 2:
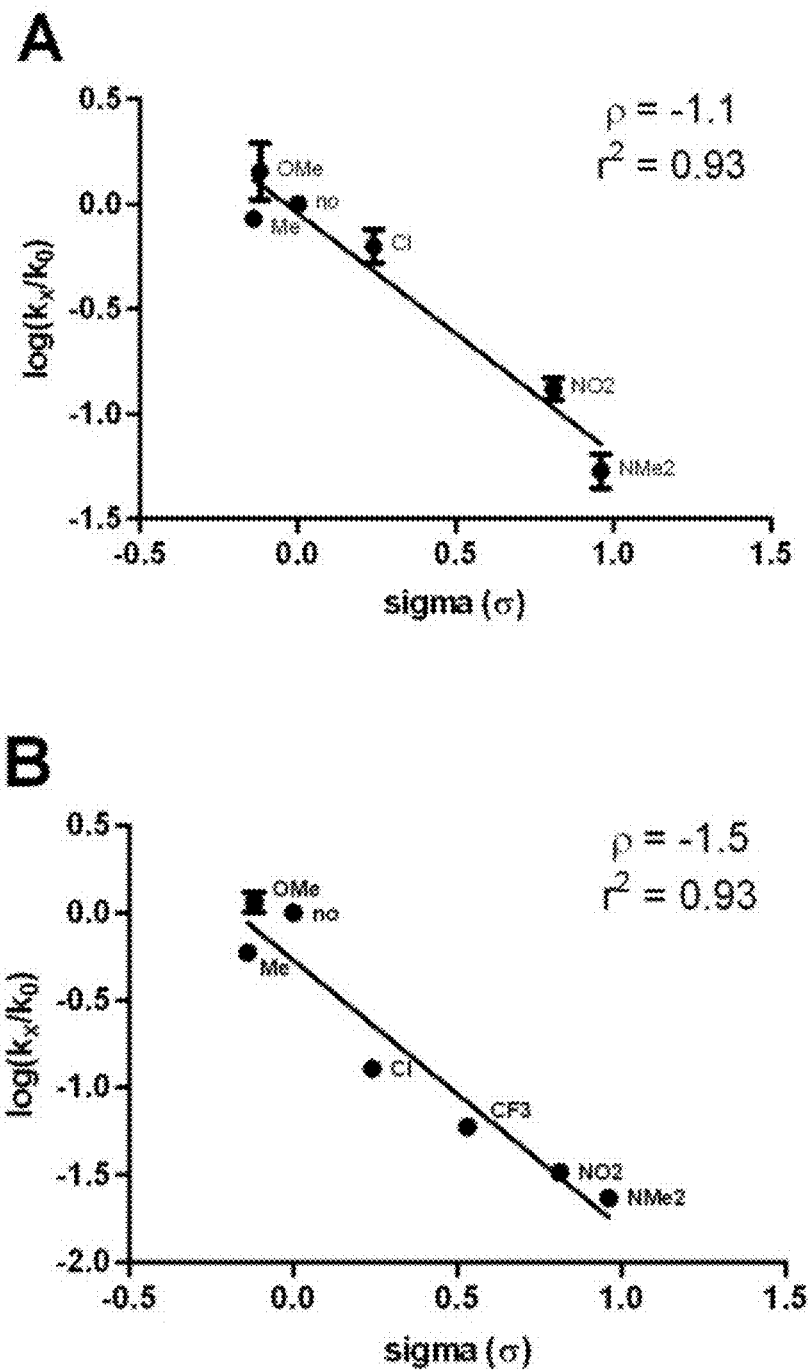
FIG. 2 shows linear free energy relationships between VDS-SRC2-3 inhibition and the electronic nature of compound substituents for: A) Compounds 30a-30f; and B) Compounds 31a-31f.

The azafulvenium salts are reactive electrophiles that can undergo reactions with natural occurring nucleophiles such as cysteine residues of proteins. The wide range of reaction rates of the differently substituted 3-indolyl-methanamines and the fact that these compounds are likely to react with VDR irreversibly, the possibility of a linear free energy relationship between the alkylation of VDR measured by disruption of VDR-SRC2-3 binding and the electronic nature of different aromatic 3-indolyl-methanamine substituents was investigated. Log($k_x/k_0$) was plotted against Hammett G-values for the compounds of series 30 and 31 (FIGS. 2A and 2B respectively). log($k_x/k_0$) values were calculated using rate constants given in Table 2. $K_0$ being the non-substituted compounds 30a and 31a. σ-values were obtained from Ritchie et al. (*Prog. Phys. Org. Chem.* 1964, 2.) ρ-values represent the slopes of the linear regressions with the corresponding $r^2$ values.

A strong correlation was found for both series ($r^2$ values are 0.93) with significant negative ρ-values, supporting the proposed mechanism that during the rate determining step, a positive charge is building up. Additionally, this reaction is less sensitive to substituents of compound series 30 (ρ=−1.1), than to substituents of compound series 31 (ρ=−1.5). This supports the fact that substituents of series 30 have a majorly inductive stabilizing effect, resulting in a smaller absolute ρ-value than substituents of compound series 31, which can stabilize the positive charge via resonance.

Example 6

Selectivities Toward Nucleophiles

Figure 3:
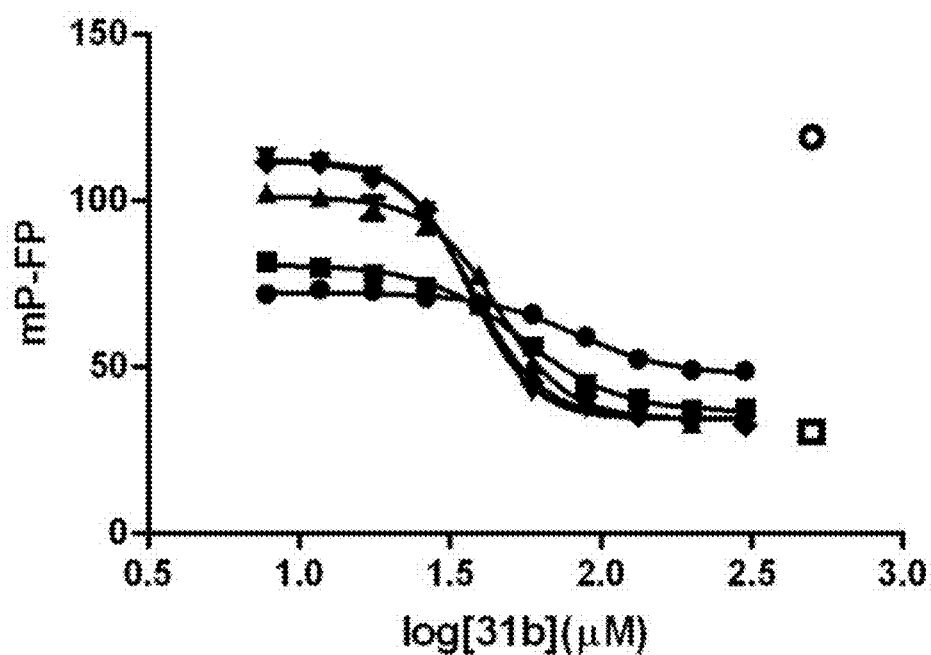
FIG. 3 shows fluorescence polarization binding isotherms following incubation of VDR-LBD, LG190178, and Alexa Fluor-labeled SRC2-3 peptide in the presence of different concentrations of compound 31b and in the absence and presence of different concentrations of 2-mercaptoethanol. ○ DMSO (negative control), □ 3-dibutylamino-1-(4-hexylphenyl)-propan-1-one (positive control), 2-mercaptoethanol concentrations (31b IC$_{50}$ values): ●100 mM (82.2±7.3 μM), ■ 10 mM (54.5±3.1 μM), ▲ 1 mM (45.4±2.0 μM), ▼ 0.1 mM (37.5±1.1 μM), ♦ 0.01 mM (36.8±0.5 μM).

In water at a neutral pH, 3-indolyl-methanamines were stable for 24 hours, but reaction occurred when high concentrations of 2-mercaptoethanol (5 mM) were added. To determine the selectivity of 3-indolyl-methanamine (31b) towards different nucleophiles, an FP assay of different concentrations 2-mercaptoethanol was carried out. VDR-LBD (1 μM), LG190178 (5 μM), and Alexa Fluor-labeled SRC2-3 peptide (7 nM) were incubated in the presence of different concentrations of 31b and in the absence and presence of different concentrations of 2-mercaptoethanol. Interactions between VDR and SRC2-3 were determined by fluorescence polarization. Results are shown in FIG. 3, where: ○ DMSO (negative control), □ 3-dibutylamino-1-(4-hexyl-phenyl)-propan-1-one (positive control), 2-mercaptoethanol concentrations (31b $IC_{50}$ values): ● 100 mM (82.2±7.3 μM), ■ 10 mM (54.5±3.1 μM), ▲ 1 mM (45.4±2.0 μM), ▼ 0.1 mM (37.5±1.1 μM), ◆ 0.01 mM (36.8±0.5 μM).

Two effects were observed. First, the $IC_{50}$ values for 31b under identical conditions increased with the amount of 2-mercaptoethanol from 36.8 μM (0.01 mM 2-mercaptoethanol) to 82.2 μM (100 mM 2-mercaptoethanol). Second, the efficacy of each isotherm decreased with increasing amount of 2-mercaptoethanol. These results show that VDR-SRC2-3 binding inhibition by 31 b was only changed in the presence of more than a 1000-fold excess of an alternative nucleophile, such as 2-mercaptoethanol.

Example 7

Nuclear Receptor Selectivities

To determine the Nuclear Receptor (NR) selectivity of the compounds, five additional (NR)-coactivator interactions were investigated: androgen receptor (AR)—SRC2-3, thyroid receptor (TRα)—SRC2-2 and (TRβ)—SRC2-2, estrogen receptor β (ERβ)—SRC2-2, and peroxisome proliferator-activated receptor γ (PPARγ)-DRIP2 (VDR-interacting protein 205). The quantification of these NR-coactivator interactions has been reported previously (Estebanez-Perpina et al. *J Biol Chem* 2005, 280, 8060-8068; Moore et al. *J Biol Chem* 2004, 279, 27584-27590). Binding was evaluated using fluorescence polarization (FP). FP was detected at an excitation/emission wavelength of 595/615 nm. The conditions for different NRs are as follows: AR: androgen receptor LBD (5 μM), Texas Red-labeled SRC2-3 (7 nM), and dihydrotestosterone (5 μM) were incubated with small molecule for 3 h; TRa: thyroid receptor α LBD (2 μM), Texas Red-labeled SRC2-2 (7 nM), and triiodothyronine (1 μM) were incubated with small molecule for 3 h; TRβ: thyroid receptor β LBD (0.8 μM), Texas Red-labeled SRC2-2 (7 nM), and triiodothyronine (1 μM) were incubated with small molecule for 3 h; ERβ: estrogen receptor β (3 μM), Texas Red-labeled SRC2-2 (5 nM), and estradiol (0.1 μM) were incubated with small molecule for 3 h; PPARγ: peroxisome proliferator-activated receptor γ (5 μM), Texas Red-labeled DRIP2 (7 nM), and rosiglitazone (5 μM) were incubated with small molecule for 3 h; VDR: vitamin D receptor LBD (1 μM), Texas Red-labeled SRC2-3 (7 nM), and LG190178 (5 μM) were incubated with small molecule for 3 h.

Figure 4:
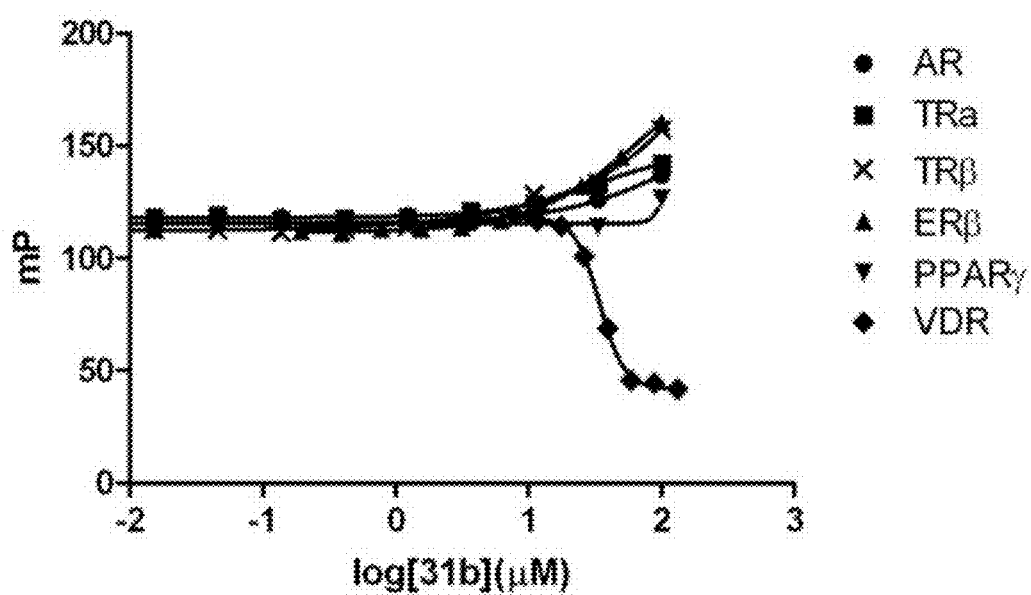
FIG. 4 shows fluorescence polarization binding isotherms following incubation of different concentrations of compound 31b with: AR: androgen receptor LBD, Texas Red-labeled SRC2-3, and dihydrotestosterone were incubated with small molecule for 3 h; TRα: thyroid receptor α LBD, Texas Red-labeled SRC2-2, and triiodothyronine were incubated with small molecule for 3 h; TRβ: thyroid receptor β LBD, Texas Red-labeled SRC2-2, and triiodothyronine; ERβ: estrogen receptor β, Texas Red-labeled SRC2-2, and estradiol; PPARγ: peroxisome proliferator-activated receptor γ, Texas Red-labeled DRIP2, and rosiglitazone; VDR: vitamin D receptor LBD, Texas Red-labeled SRC2-3, and LG190178.

Compounds 30a-30h, 31a-31h, and 32a-32c all exclusively disrupted the VDR-SRC2-3 interaction, as depicted for compound 31b in FIG. 4.

Example 8

VDR-Coregulator Interactions

The abilities of compounds to inhibit different VDR-coregulator interactions were also determined. The quantification of interactions between VDR and coregulator peptides was reported recently (Teichert et al. *Biochemistry* 2009, 48, 1454-1461). Herein, three different coregulators were tested, which include SRC2 (Masuyama et al. *Mol Endocrinol* 1997, 11, 1507-1517; Hong et al. *Mol Cell Biol* 1997, 17, 2735-2744; Li et al. *Proc Natl Acad Sci USA* 1997, 94, 8479-8484); DRIP205 (Rachez et al. *Genes Dev* 1998, 12, 1787-1800), and Hairless [Hr](Hsieh et al. *J Biol Chem* 2003, 278, 38665-38674). A VDR-LBD (1 μM), LG190178 (5 μM), and different Texas Red-labeled coregulator peptides (7 nM) were incubated for 3 h in the presence of different concentrations of compound 31b. Binding was evaluated using fluorescence polarization.

Figure 5:
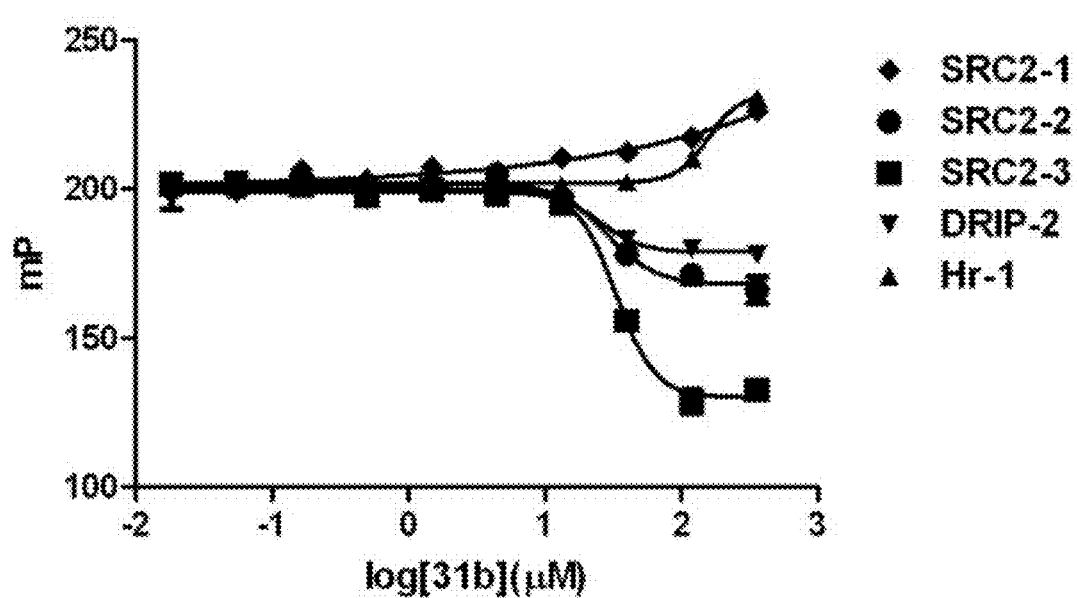
FIG. 5 shows fluorescence polarization binding isotherms following incubation of different concentrations of compound 31b with VDR-LBD, LG190178, and different Texas Red-labeled coregulator peptides.

The results employing compound 31b are summarized in FIG. 5. Inhibition of binding was observed in the presence of 31b for VDR-SRC2-2, VDR-SRC2-3, and VDR-DRIP2. The efficacy of these isotherms is dissimilar because of the different binding constants between VDR and SRC2-2 ($K_d$=1.7±0.2 μM), VDR and SRC2-3 ($K_d$=0.93±0.17 μM), and VDR and DRIP-2 ($K_d$=1.6±0.2 μM). In comparison, the binding constant between VDR and SRC2-1 and VDR and Hr1 is greater than 5 μM and no inhibition by compound 3 b was observed under these conditions. Interestingly, the $IC_{50}$-values of 31b and for the VDR-SRC2-2, VDR-SRC2-3, and VDR-DRIP-2 interactions are very similar ($IC_{50}$=25.4±6.5 μM, $IC_{50}$=28.5±6.9 μM, and $IC_{50}$=33.1±3.4 μM, respectively).

Example 9

Pull Down Assay

The ability of 31b to partially inhibit the interaction between VDR and SRC2, containing all three SRC2 NIDs was tested using a pull down assay. GST fusion to the SRC2 bearing all three NIDs were expressed in *Escherichia coli* BL21. Cultures were grown to $OD_{600}$=0.5-0.6 at 22° C. and induced with 0.5 mM isopropyl-D-thiogalactoside for 12 h.

The cultures were centrifuged (1000×g), and bacterial pellets were resuspended in 20 mM TRIS, pH 7.4, 200 mM NaCl, 1 mM NaN3, 0.5M EDTA, 1 mM DTT, protein inhibitors cocktail (Roche) and sonicated. Debris was pelleted by centrifugation (100,000×g). The supernatant was incubated with glutathione-Sepharose 4B beads (Amersham Biosciences) and washed. Protein on bead was stored with 10% glycerol at −20° C. Each pull-down reaction was carried out in 100 µl buffer (25 mM PIPES (pH 6.75) 50 mM NaCl, 0.01% NP-40, 2% DMSO) using 100 nM calcitriol, 10 µM VDR-LBD-MPB, and 31b. After 2 hours at rt, 15 µl of SRC2-beads was added to each reaction followed by 30 minutes incubation. The reaction was filtered, washed with buffer (100 µl) and eluted from the bead using a buffer and 10 mM reduced glutathione. Separation was carried out using SDS-PAGE followed by Western blotting using standard procedures with anti-MBP (E8032S, New England BioLabs) and anti-mouse IgG-Tr (sc-2781, Santa Cruz).

FIG. 6a shows a Western Blot following the above assay. Lanes 1-3 show results using different concentrations of 31b in the presence of VDR, SRC2 and 1,25(OH)$_2$D$_3$; lane 4 VDR, SRC2 and 1,25(OH)$_2$D$_3$; lane 5 no ligand (1,25 (OH)$_2$D$_3$); lane 6 no coregulator (SRC2).

Control experiments indicate that SRC2 bound to VDR in the presence of VDR ligand 1,25(OH)$_2$D$_3$(FIG. 6a, lane 4) but not in the absence of 1,25(OH)$_2$D$_3$(FIG. 6a, lane 5). The VDR-SRC2 interaction was blocked in a dose dependent manner by 31b (FIG. 6a, lane 1-3). Although significant inhibition of the VDR-SRC2 interaction was observed at a concentration of 50 µM and 100 µM of 31b, a residual interaction between VDR and SRC2 could still be detected. Thus, the inhibition of the interaction between VDR and full length SRC2 by 31b exhibit dose response dependence, similar to the SRC2-2 peptide binding study described above.

The interaction between VDR and SRC2 in the presence of compound or vehicle was also investigated prior to the pull-down assay, to discriminate between 31b-VDR and 31b-SRC2 binding, respectively. FIG. 6b shows a Western Blot of in vitro binding reactions between SRC2 bearing all three NIDs and two different compounds. Lane 1: preincubation SRC2 with 31b; Lane 2 pre-incubation with 32a; and lane 3 pre-incubation with vehicle only. After incubation, beads were washed, treated with VDR and VDR-SRC2 interactions were determined by Western blot. VDR-SRC2 interactions could be verified for all reaction conditions, although 31b, in contrast to 32a, was able to inhibit the interaction between VDR and SRC2 (Table 2 and FIG. 6b). Thus, pre-incubation of 31b with SRC2, in contrast to pre-incubation of 31b with VDR (FIG. 6b), did not result in an alkylation reaction and therefore VDR-SRC2 binding was observed.

Example 10

Expression Levels of TRPV6 and CYP24A1

To examine the influence of VDR-coactivator inhibition by 31b in respect to VDR-mediated transcription, expression levels of the transient receptor potential vanilloid type 6 gene (TRPV6) were investigated. The gene product of TRPV6 (ECaC2 or CaT1) is a membrane Ca$^{2+}$ ion channel, which is highly expressed in advanced prostate cancer (Wissenbach et al. *Biochem Biophys Res Commun* 2004, 322, 1359-1363; Nijenhuis et al. *J Am Soc Nephrol* 2003, 14, 2731-2740) and was reported to be directly regulated by VDR in the presence of 1,25-(OH)$_2$D$_3$(Meyer et al. *Mol Endocrinol* 2006, 20, 1447-1461). DU145 cells were cultured in six-well plates and treated with 1,25-(OH)$_2$D$_3$ (20 nM) and/or small molecule 31b. TRPV6 expression levels were determined by semi-quantitative RT-PCR (as described above) and normalized to GAPDH transcript level and to DMSO control condition. The ΔΔCt method was used to measure the fold change in expression of genes. Standard deviations were calculated from three biological independent experiments performed in triplicate.

Figure 7:
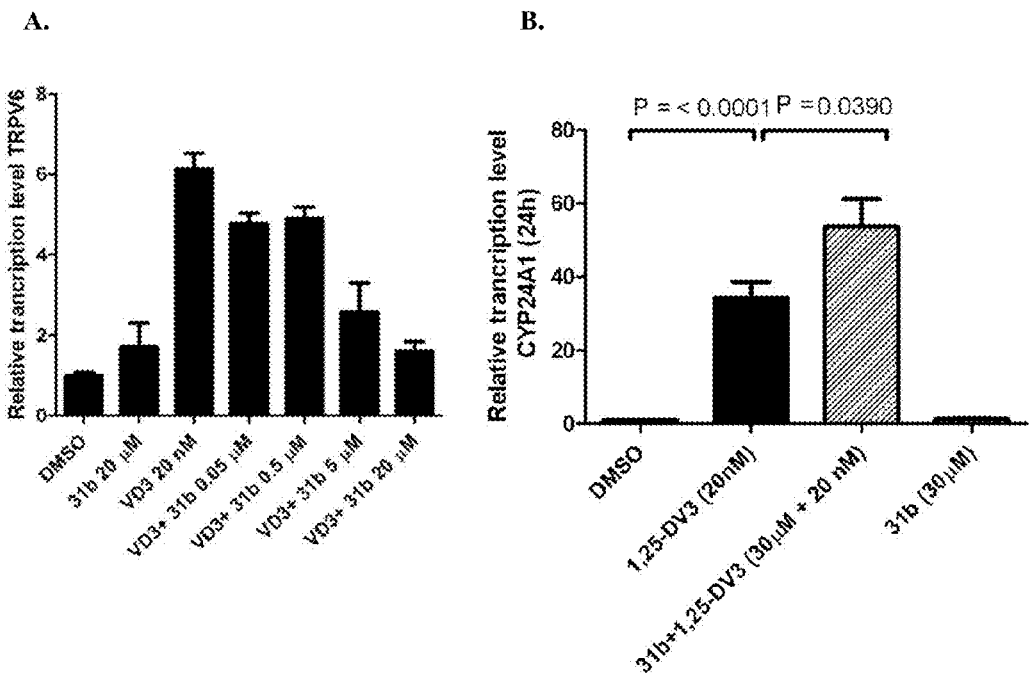
FIG. 7 shows: (A) relative transcription levels of the transient receptor potential vanilloid type 6 gene (TRPV6) in the presence and absence of 1,25-(OH)$_2$D$_3$ and increasing concentrations of compound 31b; and (B) relative transcription levels of the CYP24A1 gene in the presence and absence of 1,25-(OH)$_2$D$_3$ and compound 1.

The expression levels of TRPV6 in the prostate cancer cell line DU145 in the presence and absence of 1,25-(OH)$_2$D$_3$ and compound 31b are depicted in FIG. 7a. In the presence of 1,25-(OH)$_2$D$_3$, TRPV6 was up-regulated in DU145 cells. The single treatment of cells with 3-indolyl-methanamine 31b at 20 µM showed no regulation of TRPV6. For 31b concentrations higher than 20 µM an increased cytotoxicity was observed (see supplemental material). To the contrary, in the presence of 20 nM 1,25-(OH)$_2$D$_3$ and different concentrations of 31b, TRPV6 transcription was reduced in a dose dependent manner confirming that 31b is modulating TRPV6 expression by interacting with VDR.

In an analogous manner, expression levels of CYP24A1 were also evaluated, as shown in FIG. 7b. In the presence of compound 1 (N-((1H-indol-3-yl)(phenyl)methyl)aniline), no modulation of CYP24A1 was noticed, but in the presence of compound 31b and calcitriol, a significant increase in CYP24A1 induction was observed in comparison to calcitriol treatment.

Example 11

VDR Expression in SKOV3 Cells

Figure 8:
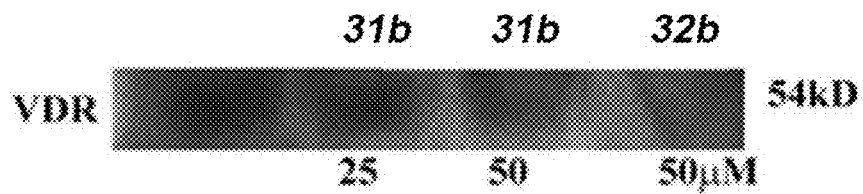
FIG. 8 shows Western blots of whole cell lysates of SKOV-3 cells following incubation with compounds, using a monoclonal antibody against VDR.

VDR expression platinum resistant ovarian cancer (SKOV-3 cells) treated with compound 31b or compound 32b. Cells were treated with vehicle (DMSO), 31b (25 and 50 uM) or compound 32b (50 uM) for 24 hours. Expression of VDR was analyzed by western blotting of whole cell lysate using monoclonal antibody against VDR (Neomarker, Calif. cat no-RT-200PO). Treatment with both compounds resulted in downregulation of VDR in SKOV-3 cells, as illustrated in FIG. 8.

Example 12

Cytotoxicity Studies

Figure 9:
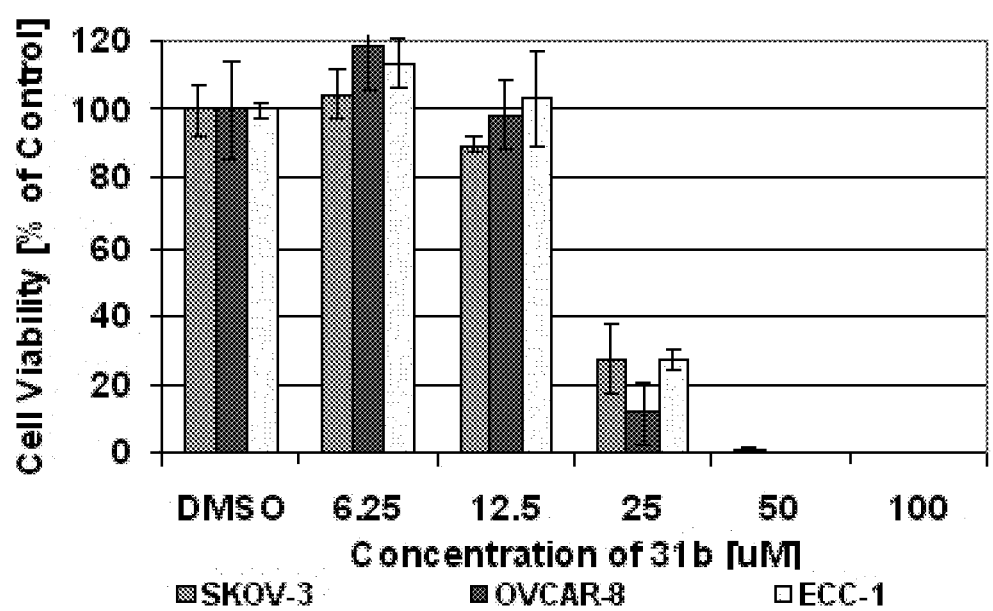
FIG. 9. shows cell viabilities of SKOV-3, OVCAR-8 and EEC-1 cells following treatment with varying concentrations of 31b.

The cytotoxic potential of compound 31b and other two structurally similar compounds were determined in a panel of platinum resistant ovarian cancer cell (SKOV-3 and OVCAR-8) lines and in a hormone responsive endometrial cancer cell-line (ECC-1) in vitro. These cell lines were treated with varying concentrations of 31b and the cell viability was determined by MTS assay. As shown in FIG. 9, compound 31b showed potent cytotoxicity against both ovarian (SKOV-3, OVCAR-8) cell lines and endometrial cancer cell-lines within 48 hours of the treatment. Other close structural analogs 32b and 32c did not show any cytotoxicity against these cell-lines (data not shown).

Example 13

Evaluation of Apoptotic Pathways in SKOV-3 Cells

Figure 10:
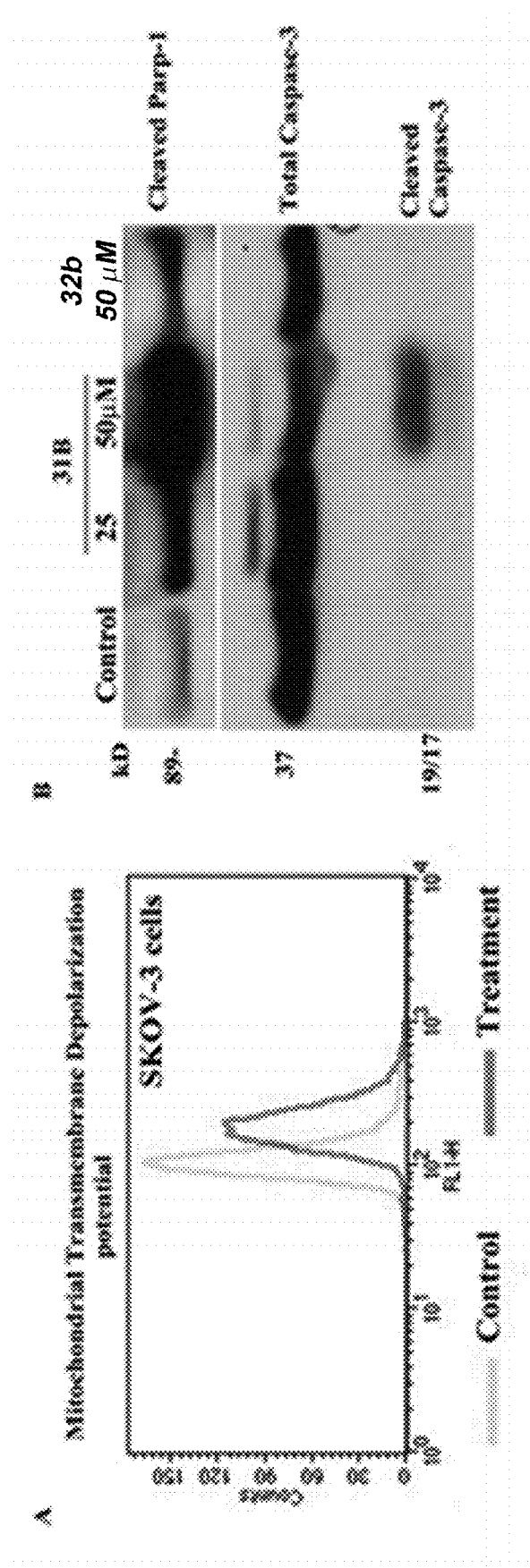
FIG. 10 shows: (A) mitochondrial transmembrane depolarization potentials in control cells and compound 31b-treated SKOV-3 cells; and (B) Western blots of whole cell lysates of SKOV-3 cells probed for cleaved PARP-1 and cleaved caspase-3 following treatment with control, varying concentrations of compound 31b or compound 32b.

FIG. 10 demonstrates that compound 31b induces apoptosis in ovarian cancer cells via non-mitochondrial pathways: (A): 31b treatment induced activation of mitochondrial transmembrane depolarization potential (ΔΨm). (B): 31b treatment caused significant cleavage of PARP-1 and activation of caspase-3, the executioner caspase in ovarian cancer cells. The whole cell lysates of SKOV-3 cells treated with vehicle, 31b or compound 32b were probed for cleaved PARP-1 and cleaved caspase-3.

Mitochondrial defects and the dysfunctions of oxidative phosphorylation and energy production in ovarian cancer cells were directly related to their resistance to platinum drugs and contribute to epithelial ovarian cancer oncogenesis (Dai et al. *Proteomics* 2010, 10(21), 3789-99). Compound 31b has shown unique potential to cause apoptosis without disrupting mitochondrial transmembrane depolarization potential. Further, experiments show that targeting VDR via compound 31b resulted in strong PARP-1 cleavage followed by activation of caspse-3 in platinum resistant ovarian cancer cells within 24 hours of treatment. PARP-1 maintains cellular integrity of cancer when exposed to cytotoxics or radiations. Targeting PARP-1 by small molecular PARP-1 inhibitors is a current therapeutic approach in the treatment of ovarian cancer and Rucaparib is currently in phase-II clinical trials to treat metastatic ovarian cancer (clinicaltrials. gov; NCT00664781).

Example 14

Activation of MAPkinase Pathways and ROS in SKOV-3 Cells

Figure 11:
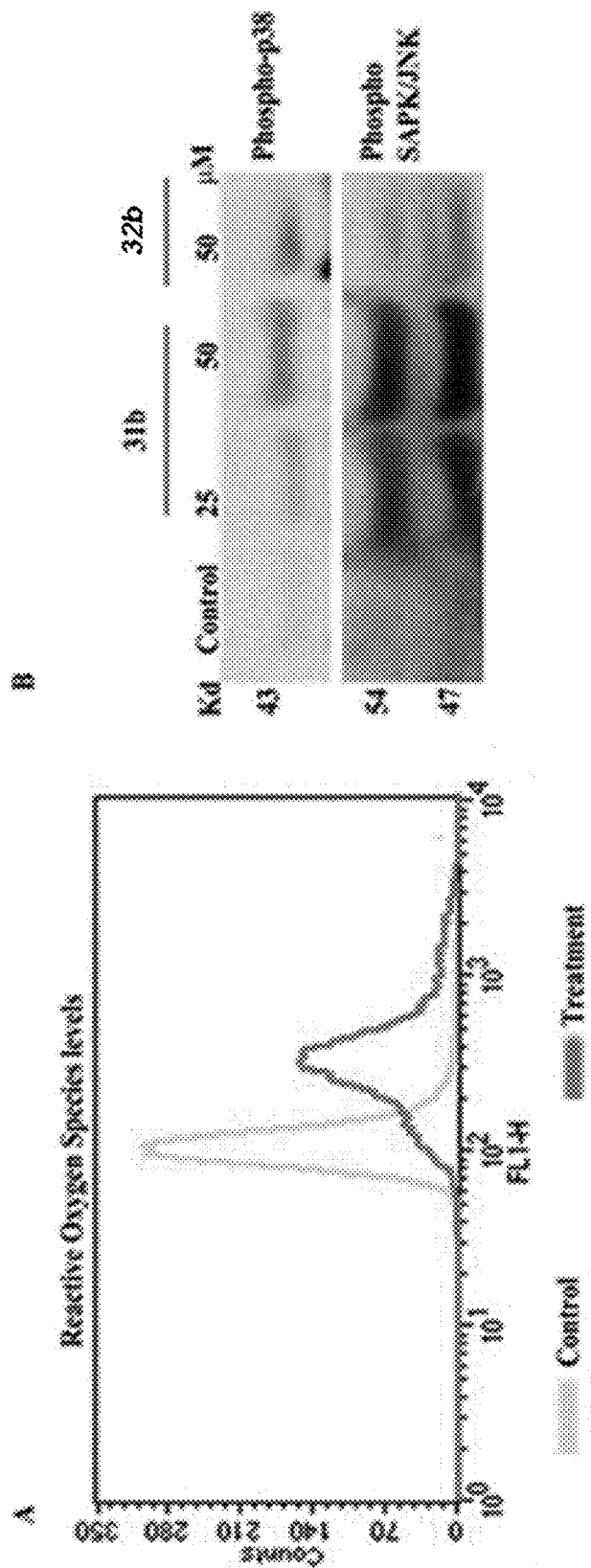
FIG. 11 shows: (A) levels of reactive oxygen species in control cells and compound 31-b treated SKOV-3 cells; and (B) Western blots of whole cell lysates of SKOV-3 cells probed for phospho-p38 MAPkinase (upper panel), and phospho SAPK/JNK (lower panel), following treatment with control, varying concentrations of compound 31b or compound 32b.

Vitamin-d/VDR signaling protects the cancer cells from reactive oxygen species (ROS) induced cellular damages. Therefore inhibiting VDR to achieve lethal levels of ROS can be considered an approach to selectively kill ovarian cancer cells possessing higher cellular rate of metabolism than normal ovarian cancer cells. FIG. 11 demonstrates that compound 31b induces strong ROS production and MAPK/SAPK activation ovarian cancer cells. (A): SKOV-3 cells upon treatment with 31b (pink) showed elevated level of reactive production compared to vehicle (green) within 24 hours of treatment. (B) Compound 31b showed activation of p38 MAPkinase (upper panel) and strong/sustained activation of SAPK/JNK at 25 uM dose within 24 hours. As a positive control, another structural analog 32b treatment did not cause the similar activation of p38 or SAPK/JNK in ovarian cancer (SKOV-3) cells.

Example 15

Cell Cycle Analysis of SKOV-3 Cells

Figure 12:
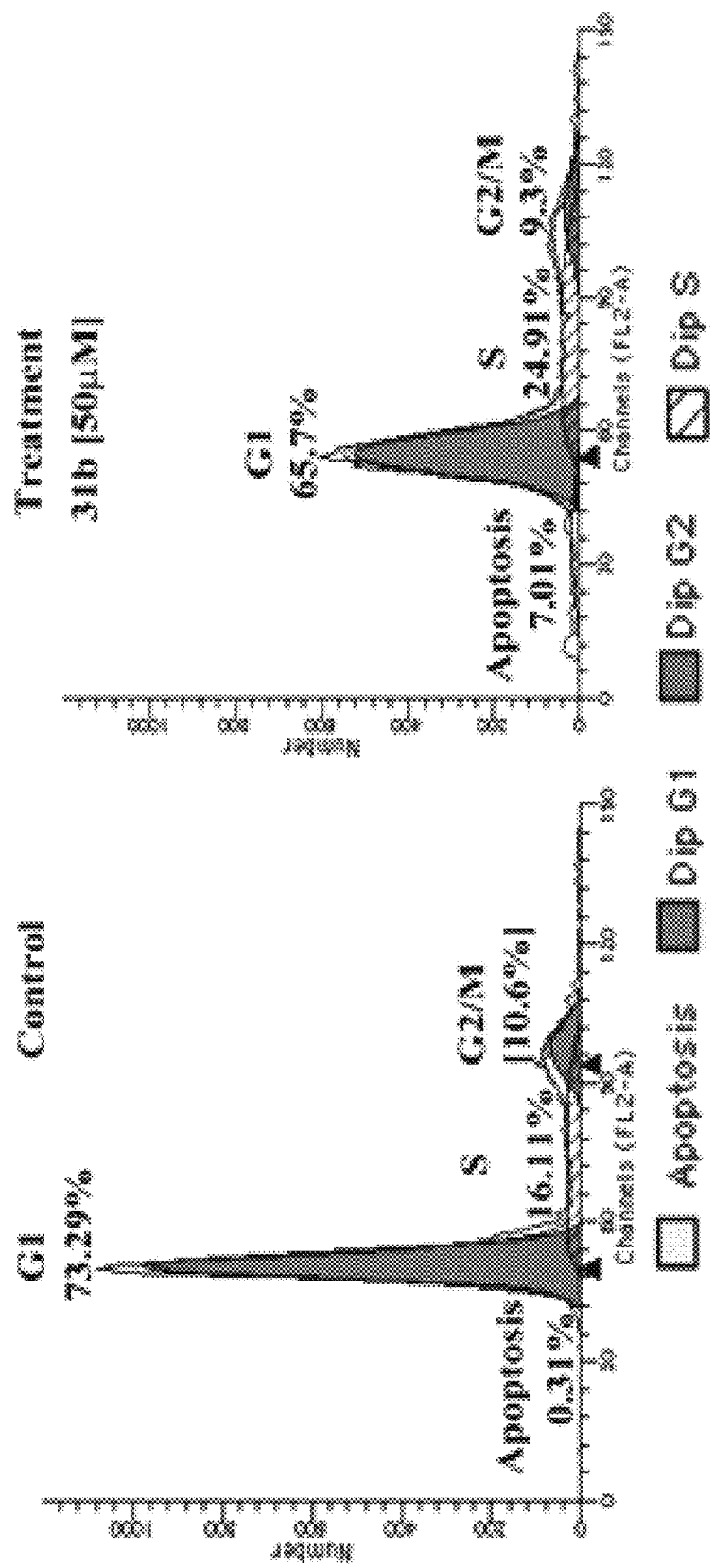
FIG. 12 shows FACS analysis to determine cell cycle distribution of SKOV-3 cells treated with vehicle for 24 hours (left panel), and FACS analysis of SKOV-3 cells treated with compound 31b for 24 hours (right panel.

Cancer cells characteristically do not regulate cell cycle progression and therefore grow unabated. Inducing cell cycle arrest or targeting cell-cycle regulators by small molecule modulators has shown promising outcomes in animal models. Therefore, 31b induced S-phase arrest in progressing ovarian cancer (SKOV-3) cells was evaluated. FIG. 12 shows the results of FACS analysis of cell cycle distributions following treatment of SKOV-3 cells with vehicle for 24 hours (left panel) and compound 31b for 24 hours (right panel).

As shown in FIG. 12, treatment with compound 31b restricted the progression of cycling cells in S-phase significantly within 24 hours of treatment. Further S-phase arrest caused increase in apoptotic (subgl/GO) population. Similarly, the population in Gi and G2/M phase were also reduced Indicating that compound 31b can specifically target S-phase accumulation of cycling ovarian cancer cells.

Example 16

Additional Compound Syntheses

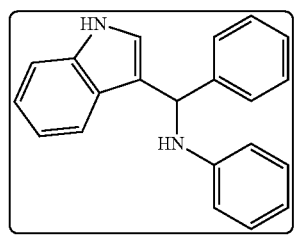

1

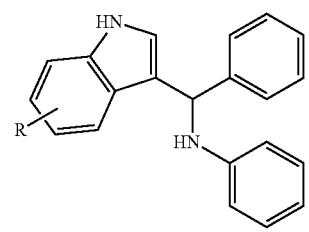

2

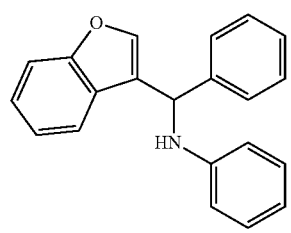

3

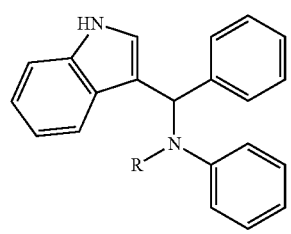

4

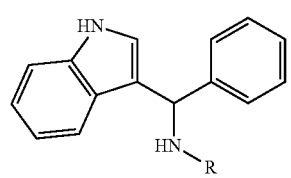

5

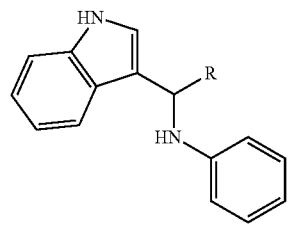

6

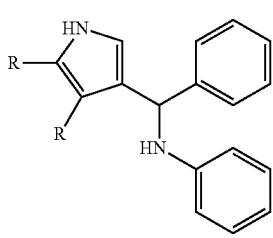

The general description of the aza-Friedel-Crafts reaction regarding the synthesis of 3-indoyl-methanamines will be applied to other compounds, such as compounds 2-7. The application of substituted indoles will result in the analogs 2. Nitrogen/oxygen substitution of compound 1, represented by compound 3, will be generated by employing benzofuran, instead of indole. Analogs 4 will be synthesized starting with N-substituted anilines. Compounds 5 and 6 will be generated by using different amines and aldehydes. These analogs will have aromatic and heterocyclic substituents. The synthesis of analogs 7 will be realized by using substituted pyrroles, instead of indoles Example 17

Further Solubility Assays

To verify the chemical stability of compounds in buffered solutions at different pH, compounds will be dissolved within the solubility range at three different concentrations in four buffer systems with different pH (2.0 (stomach), 6.0 (small intestine), and 7.2 (blood). The amount of the parent compound and identity of new compounds formed will be determined by liquid chromatography-mass spectrometry (LCMS) for different time ranges. The stability of compounds in mouse blood plasma will be determined in 50% plasma/PBS, at 37° C. for up to 3 hours using LCMS. Propoxycaine will be used as a positive control for plasma activity. Compound mouse liver microsome stability will be determined using a similar assay. Instead of 50% plasma/PBS a mouse microsome solution (0.7 mg/ml protein) can be used in the presence of NADPH. As a positive control diphenhydramine will be used. Finally, compounds will be incubated with mouse hepatocytes at a cell concentration of 0.5 M cell/ml at 37° C. for up to three hours followed by the analysis of the media using LCMS. 7-Hydroxcoumarin will be used as a positive control. For all assays described, half life times ($t_{1/2}$=0.693/k) will be determined. Once the compound stability is determined, different formulations will be investigated in order to ip administer the compound. Two cosolvents will be investigated: ethanol and polyethylene glycol. The established solubility assay based on absorption will be used for quantification.

Example 18

Evaluation in Additional Cell Lines

Three cancer cell lines (MCF-7, LNCaP, and Caco-2) will be treated with VDR-coregulator inhibitors and/or calcitriol in order to determine antiproliferation and tissue selectivity. Treatments that will cause significant inhibition of cell growth will be further investigated by determining the cell phase distributions in order to identify apoptosis. The underlying mechanism of cell growth inhibition will be further analyzed with the quantification of VDR target gene mRNA levels.

Specifically, cell growth inhibition of MCF-7, LNCaP, and Caco-2 cells in the presence of 3-indolyl-methanamine and/or calcitriol will be determined using a Cell Titer-Glo assay (Promega) over a period of 7-10 days. Treatments causing significant cell growth inhibition will be further investigated by fluorescence-activated cell sorting (FACS) in order to determine the cell phase distribution. This method has previously been used for the detection of apoptotic properties of colchicine (Arnold et al. Bioorg Med Chem Lett, 18, 5867-5870). The regulated genes affiliated with growth inhibition in MCF-7, LNCaP, and Caco-2 cells in the presence of calcitriol were identified by microarray experiments and confirmed by qRT-PCR, and include the following genes: IGFBP-3, NDRG1, 15-PGDH, PLAB, ABC1, POV1, XPC, Claudin 4, UGT2 B15, C/EBPδ, IκBα, MRP for LNCaP cells (Krishnan et al. (2004) Prostate, 59, 243-251); CYP24A1, TGFB2, IGFBP-3, EGFR, MAPK4, PAK-1, and BRCA-2 for MCF-7 cells (Towsend et al. (2006) Oncology, 71, 111-123); and CYP24A1, JUNB, GEM, TRPV6, and RARRES1 (Wood et al. (2004) Physiol Genomics, 17, 122-129) for Caco-2 cells. The mRNA levels of these genes will be quantified after 6, 12, and 24 hours for treatments causing cell growth inhibition. Chromatin immunoprecipitation experiments will be used to verify the small molecule inhibition of VDR-coregulator complexes bound to VDR target genes. This method has been reported for the characterization of TR-coactivator inhibitors (Sadana et al. (2011) ACS Chem. Biol. 6(10):1096-1106).

Example 19

Evaluation in Ovarian Cancer Animal Models

Xenograft ovarian cancer models are well suited to evaluate new chemotherapies, and will be used to evaluate the anti-cancer efficacies of compounds. The influence of compounds in an ovarian cancer mouse model will be determined in regard to tumor growth inhibition and regulation of genes responsible for tumor cell growth.

Immunodeficient nude mice will be injected with SKOV-3 cells subcutaneously in the flank. Mice with developing tumors after two weeks will be randomly assigned to experimental groups. In triplicate, groups of 9 animals will be treated intraperitoneally every other day with 31b, calcitriol or vehicle. The initial dosage will be 50 mg/kg (31b) for 35 days. Mice will be weighed and tumor size calculated using a caliper every 5 days. Survival curves will be estimated using the Kaplan-Meier method. Blood will be drawn on day 10, 20 and 30 (endpoint) and calcium levels will be quantified by using a calcium-sensitive fluorescence probe. Tumors will be harvested and flash-frozen, followed by RNA extraction and RT-PCR analysis for the following VDR target genes involved in proliferation: CYP24A1, TRPV6, IGFBP3, and Bcl-xL. Protein levels of VDR, coregulators SRC2 and DRIP, PARP-1, p38, JUN, and the gene product of CYP24A1, TRPV6, IGFBP3, and Bcl-xL will be quantified by Western blot. Proliferation activity of tissue sections will be determined by Ki-67 protein quantification, which is a cellular marker for proliferation. Apoptosis in tissue sections will be determined by terminal deoxynucleotide transferase-mediated dUTP nick end labeling (TUNEL). Additionally, immunohistochemistry staining will be used to determine the localization of proteins analyzed by Western blot.

Mice treated with a compound may show a reduction in tumor size without showing signs of hypercalcemia after 15 days in contrast to animals treated with calcitriol. Apoptosis is expected to cause tumor reduction verified by a change apoptotic gene expression and protein concentrations in tumor tissue. In case that treated animals would not show a reduction in tumor size and morbidity would not be observed, the concentration over compound would be increased (e.g., to 75 mg/kg) and the above study would be repeated.

Example 20

Evaluation in Antiangiogenic Effects

The angiogenic or antiangiogenic effects of compounds described herein will be determined by an in vitro, an ex-vivo and an in vivo method. For the in vitro analysis of angiogenic or antiangiogenic effects, human umbilical vein endothelial cells (HUVEC) (10000 cells/well) will be grown on BME-coated 24 well chambers and allowed to grow for 6-12 hours following an in vitro angiogenesis/tube formation kit (Trevigen, Md., USA. Cat No-3470-096-K). The tube formation output due to vehicle or the compounds will be analysed by microscopy after staining with Calcien AM (see Kim et al., *International Journal of Oncology*, 2012, 40:226-235). An ex vivo rat aorta model based assay will also be conducted to assess the angiogenic/antigiogenic effects of the compounds. In this assay, fresh harvested rat aortic rings pieces will be allowed to grow on matrigel precoated 12 well chambers in DMEM media for 7-8 days, when a strong capillary network would have formed. The media will be replaced with a fresh media containing various doses of the compound, and incubated for various time durations. The structural features of the capillary and the capillary junctions will be recorded via microscopy. The in vivo angiogenic or antiangiogenic effects of the compounds will be evaluated via VEGFR and PECAM-1 staining of the xenograft human cancer cell-lines in nude animals (see Moore et al., *PLoS ONE* 7(4): e34443).

The invention claimed is:

1. A compound of formula (I):

(I)

wherein:
m is 1;
p is 1;
each $R^2$ and $R^3$ is independently selected from the group consisting of alkoxy and haloalkyl.

2. The compound of claim 1, wherein $R^2$ is haloalkyl.
3. The compound of claim 2, wherein $R^2$ is $CF_3$.
4. The compound of claim 1, wherein $R^3$ is alkoxy.
5. The compound of claim 4, wherein $R^3$ is methoxy.
6. A compound of formula (I):

(I)

wherein:
$R^2$ is $CF_3$; and
$R^3$ is methoxy.

7. A pharmaceutical composition comprising a compound according to claim 1 and a pharmaceutically acceptable carrier.

8. The pharmaceutical composition of claim 7, wherein the compound is (I)

wherein:
$R^2$ is $CF_3$; and
$R^3$ is methoxy.

9. A method of inhibiting the expression of a vitamin D receptor target gene in a sample, comprising contacting the sample with an effective amount of a compound according to claim 1.

10. The method of claim 9, wherein the compound is (I)

wherein:
$R^2$ is $CF_3$; and
$R^3$ is methoxy.

11. A method of inhibiting an interaction between a vitamin D receptor and at least one vitamin D receptor coactivator in a sample, comprising contacting the sample with an effective amount of a compound according to claim 1.

12. The method of claim 11, wherein the compound is (I)

wherein:
$R^2$ is $CF_3$; and
$R^3$ is methoxy.

13. A method of inhibiting angiogenesis in a subject in need thereof, comprising administering to the subject a therapeutically effective amount of a compound according to claim 1.

14. The method of claim 13, wherein the compound is (I)

wherein:
$R^2$ is $CF_3$; and
$R^3$ is methoxy.

* * * * *